(12) United States Patent
Mills

(10) Patent No.: US 6,224,848 B1
(45) Date of Patent: May 1, 2001

(54) PHARMACEUTICALS PROVIDING DIAGNOSIS AND SELECTIVE TISSUE NECROSIS USING MOSSBAUER ABSORBER ATOM

(76) Inventor: Randell L. Mills, R.D. 2, Cochranville, PA (US) 19330

( * ) Notice: Subject to any disclaimer, the term of this patent is extended or adjusted under 35 U.S.C. 154(b) by 0 days.

(21) Appl. No.: 08/454,012

(22) Filed: May 30, 1995

Related U.S. Application Data

(63) Continuation of application No. 07/950,973, filed on Sep. 23, 1992, now abandoned, which is a continuation of application No. 07/055,591, filed on May 28, 1987, now abandoned, which is a continuation-in-part of application No. 06/849,046, filed on Apr. 7, 1986, now Pat. No. 4,815,448, which is a continuation-in-part of application No. 06/713,448, filed on Mar. 19, 1985, now Pat. No. 4,815,447.

(51) Int. Cl.$^7$ .............................. A61K 51/00; C07F 5/00; A61N 5/00

(52) U.S. Cl. ............................. 424/1.65; 534/10; 534/11; 534/15; 600/1; 600/2; 600/3

(58) Field of Search ................................ 424/9.32, 9.321, 424/9.322, 1.11, 1.65, 1.69, 1.41, 450; 530/322; 534/10, 11, 12, 13, 14, 15, 16; 600/1, 2, 3

(56) References Cited

U.S. PATENT DOCUMENTS

| | | | |
|---|---|---|---|
| 3,257,558 | | 6/1966 | Cook et al. .......................... 250/83.3 |
| 3,937,668 | * | 2/1976 | Zolle ................................. 424/1.1 X |
| 3,974,268 | * | 8/1976 | Subramanian et al. ................ 424/1.1 |
| 4,057,616 | * | 11/1977 | Wolfangel ............................ 424/1.1 |
| 4,059,769 | * | 11/1977 | Alexandrov et al. . |
| 4,290,019 | | 9/1981 | Hutchison et al. ................... 324/311 |
| 4,354,499 | | 10/1982 | Damadian ............................ 128/653 |
| 4,357,259 | * | 11/1982 | Senyei et al. ...................... 424/1.1 X |
| 4,391,795 | * | 7/1983 | Pearlman .............................. 424/1.1 |
| 4,500,507 | * | 2/1985 | Wong ..................................... 424/1.1 |
| 4,516,535 | | 5/1985 | Russell, Jr. et al. .................. 128/1.1 |
| 4,528,509 | | 7/1985 | Radda et al. ......................... 324/309 |
| 4,544,545 | * | 10/1985 | Ryan et al. ........................... 424/1.1 |
| 4,592,363 | | 6/1986 | Krause ................................ 128/653 |
| 4,617,516 | | 10/1986 | Schenck .............................. 324/318 |
| 4,617,936 | | 10/1986 | Malko .................................. 128/653 |
| 4,629,988 | | 12/1986 | Bottomley ........................... 324/309 |
| 4,671,954 | * | 6/1987 | Goldberg et al. .................... 424/450 |
| 4,671,958 | * | 6/1987 | Rodwell et al. ........................ 424/85 |
| 4,735,796 | * | 4/1988 | Gordon .................................... 424/9 |
| 4,767,611 | * | 8/1988 | Gordon .................................... 424/9 |
| 4,861,581 | * | 8/1989 | Epstein et al. ..................... 424/1.11 |
| 4,996,991 | * | 3/1991 | Gordon ................................ 128/653 |
| 5,043,101 | * | 8/1991 | Gordon ............................. 252/408.1 |
| 5,427,767 | * | 6/1995 | Kresse et al. ....................... 424/9.32 |
| 5,492,814 | * | 2/1996 | Weissleder ........................... 435/725 |

FOREIGN PATENT DOCUMENTS 0198257   10/1986  (EP) .

WO 85/01871   5/1985  (WO) .

OTHER PUBLICATIONS

McGraw–Hill Encyclopedia of Science & Technology, 6$^{th}$ Ed., vol. 11, pp. 405–408, 1987.*

McGraw–Hill Dictionary of Chemical Terms, 3$^{rd}$ Ed., pp. 98, 101, 1984.*

Sugiura et al., "Spectroscopic Studies on Bleomycin–Iron Complexes w/ Carbon Monoxide, Nitric Oxide . . . ," Biochemica et Biophysica Acta, 716(1982), 38–44.*

Marohant et al., "Study of an Oxygenated Heme Complex in Frozen Solution by Mossbauer Emission Spectroscopy," Proc. Nat Acad Sci USA, 69(9), Sep. 1972, 2396–2399.*

York et al., "Active Sites of HemcryThin. Iron Electronic States and the Binding of Oxygen," Biochemistry, 9(23), 1970, pp. 4549–4554.*

"Localization of Metabolites in Animals Using $^{31}$P Topical Magnetic Resonance", R.E. Gordon, et al, Nature vol. 287, Oct. 23, 1980, pp. 736–738.

"Basic Ultrasonic Imaging", Medical Imaging Systems, Albert Macovsik, (1983), pp. 173–223.

"Ultrasonic Imaging Using Arrays", Medical Imaging Systems, Albert Macovsik, (1983), pp. 173–223.

2389 Medical Physics, vol. 12, No. 4, Jul./Aug. 1985, pp. 532–536, New York, "Photon Activation Therapy", Fairchild et al.

Nuclear Instruments and Methods, vol. 155, No. 1/2, Sep. 1978, pp. 97–101, North Holland Publishing Co., "High Field Mossbauer Spectrometer Using Bitter Magnets".

8164 Instruments and Experimental Techniques, vol. 24, No. 5, part 1, Sep.–Oct. 1981, pp. 1151–1153, Plenum Publishing Corp., New York, U.S. S.M. Irkaev et al, "Isomer–Shift Compensation with Resonance Detectors in Mossbauer Spectroscopy".

2107B Nuclear Instruments & Methods, section B14, No. 3, Mar. 1986, pp. 323–340, Elsevier Science Publishers B.V., Holland, J.G. Mullen et al. "Cold Moving Mice: a Microfoil Internal Conversion Electron Detector for Low and Intermediate Energy Mossbauer Transitions".

* cited by examiner

Primary Examiner—Diana Dudash
Assistant Examiner—Michael G. Hartley
(74) Attorney, Agent, or Firm—Lahive & Cockfield, LLP; Giulio A. DeConti; Nicholas P. Triano, III

(57) ABSTRACT

Pharmaceuticals and Apparatus used in combination for diagnosis and tissue necrosis applicable to provide effective and selective therapy using the Mossbauer absorption phenomenon. Selected pharmaceutical compounds containing a radiation absorber isotope are administered to a tissue and excited by a radiation source which provides energy at the corresponding resonant Mossbauer absorption frequency of isotope containing pharmaceutical, where excitation effects nuclear transitions to cause highly selective energy absorption in the selected target tissue. For diagnostic purposes, de-excitation fluorescence of the isotope is monitored. For therapeutic purposes, the energy is converted to particle radiation by the isotope at the target tissue by internal conversion followed by an Auger electron cascade which results in radiolysis of DNA resulting in lethal double strand breaks in the DNA molecules of the target tissue.

9 Claims, 17 Drawing Sheets

7 Do = Limiting Dose; Recovery time of Normal Tissue = $\tau$

Log Constant Fraction Killed For $\alpha 1 = ^-2.3$; for $\alpha 2 = ^-1.3$
Log Constant Fraction Recover For $\alpha 1$ and $\alpha 2 = .9$ where
$\tau$ = 3 doubling times.

The Mechanism of Action 12 / 29 / W

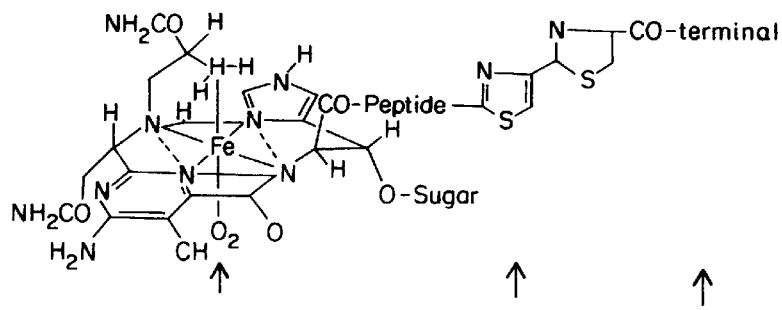

↑ Absorbs resonant Mossbauer radiation and emits Auger electrons

↑ Intercalation with DNA

↑ Electrostatic attraction with DNA

In the proposed mechanism the bithiazole rings of bleomycin intercalate between base pairs in which one chain contains a G – T or G – C sequence.

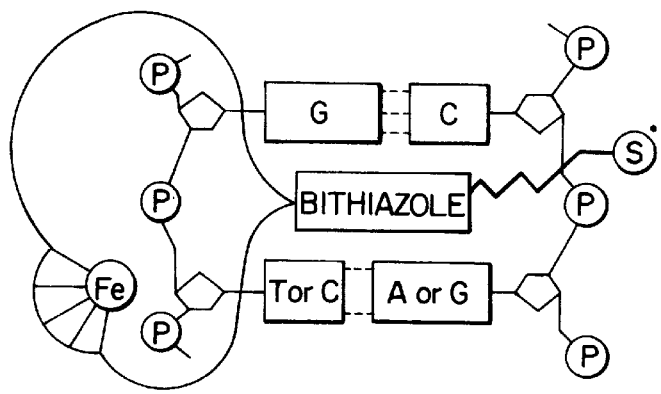

Model of Complex of 12 / 29 / W and DNA

Structure of bleomycin

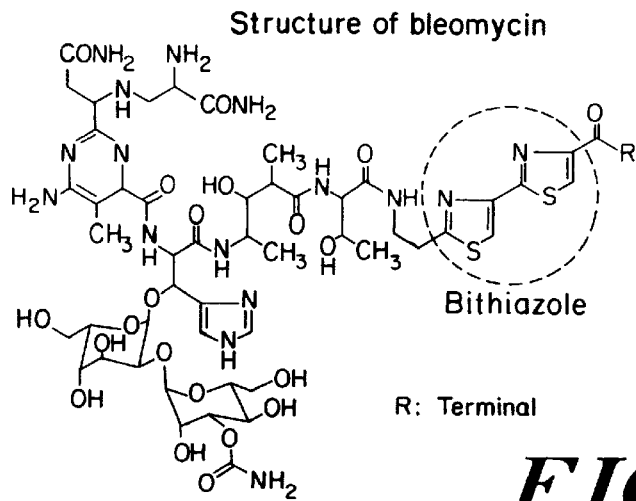

R: Terminal

*FIG. 10*

Decay Scheme of $^{57}Co$

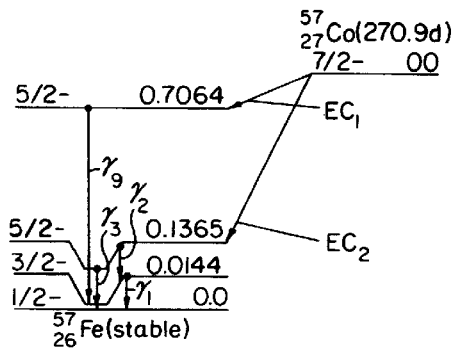

*FIG. 11*

27 – COBALT – 57

HALFLIFE = 270.9 DAYS  24 – MAY – 77
DECAY MODE(S): EC

| RADIATION | y(i) (Bq-s)$^{-1}$ | E(i) (MeV) | y(i) x E(i) |
|---|---|---|---|
| γ 1 | 9.19E-02 | 1.441E-02 | 1.32E-03 |
| ce – K, γ1 | 7.13E-01 | 7.301E-03 | 5.20E-03 |
| ce L$_1$, γ1 | 6.80E-02 | 1.357E-02 | 9.22E-04 |
| ce L$_2$, γ1 | 4.20E-03 | 1.369E-02 | 5.75E-05 |
| ce L$_3$, γ1 | 1.69E-03 | 1.370E-02 | 2.31E-05 |
| γ 2 | 8.56E-01 | 1.221E-01 | 1.04E-01 |
| ce K, γ2 | 1.84E-02 | 1.150E-01 | 2.12E-03 |
| ce L$_1$, γ2 | 1.73E-03 | 1.212E-01 | 2.10E-04 |
| γ 3 | 1.06E-01 | 1.365E-01 | 1.45E-02 |
| ce K, γ3 | 1.43E-02 | 1.294E-01 | 1.84E-03 |
| ce L$_1$, γ3 | 1.27E-03 | 1.356E-01 | 1.73E-04 |
| γ 9 | 1.60E-03 | 6.920E-01 | 1.11E-03 |
| Kα$_1$ X-ray | 3.34E-01 | 6.404E-03 | 2.14E-03 |
| Kα$_2$ X-ray | 1.69E-01 | 6.391E-03 | 1.08E-03 |
| Kβ$_1$ X-ray | 4.51E-02 | 7.058E-03 | 3.19E-04 |
| Kβ$_2$ X-ray | 2.29E-02 | 7.058E-03 | 1.61E-04 |
| Auger-KLL | 8.54E-01 | 5.574E-03* | 4.76E-03 |
| Auger-KLX | 2.04E-01 | 6.302E-03* | 1.29E-03 |
| Auger-KXY | 1.79E-02 | 7.000E-03* | 1.25E-04 |
| Auger-LMM | 2.43E-00 | 6.703E-04* | 1.63E-03 |
| Auger-LMX | 1.54E-01 | 7.067E-04* | 1.09E-04 |
| Auger-MXY | 5.33E-00 | 2.232E-05* | 1.19E-04 |

| | |
|---|---|
| LISTED X, γ AND γ + RADIATIONS | 1.25E-01 |
| OMITTED X, γ AND γ + RADIATIONS** | 1.57E-04 |
| LISTED β, ce AND Auger RADIATIONS | 1.86E-02 |
| OMITTED β, ce AND Auger RADIATIONS** | 4.08E-05 |
| LISTED RADIATIONS | 1.44E-01 |
| OMITTED RADIATIONS** | 1.98E-04 |

\* AVERAGE ENERGY (MeV)
\*\* EACH OMITTED TRANSITION CONTRIBUTES
   <0.100% TO Σy(i) x E(i) IN ITS CATEGORY.
IRON – 57 DAUGHTER IS STABLE.

FIG. 12

TOTAL ABSORBED DOSAGE:

From a source of A Ci, at a constant distance of r cm., of an isotope with mean life T, Where exposure occurs for durations u, starting at intervals of v and occuring n separate times on an organ of surface area S, density $\rho$ due to gamma rays emitted by the decays which have individual energies of E MeV and for which the organ's tissue have an energy absorption coefficient of $\mu_{en}$ cm / gram.

$$= A \text{ Ci} \times 3.7 \times 10^{10} \frac{\text{counts}}{\text{sec-Ci}} \times T \text{ sec} \times (1 - e^{-u/T}) \frac{(1 - e^{-nv/T})}{(1 - e^{-v/T})}$$

| original count rate at t = 0 |

| number of nuclei present at t = 0 | x | fraction of original nuclei that will decay during the n intervals of duration u, separation v. |

| total number of decays that occur during periods of exposure |

$$\times \frac{S}{4\pi r^2} \qquad \times (1 - e^{-\mu_{en} \rho \, dr}) \times E \text{ MeV} \times 1.6 \times 10^{-6} \frac{\text{erg}}{\text{MeV}} \times \frac{1}{\rho S \, dr} \times \frac{1}{100}$$

| fraction of rays emitted from source that will pass through surface area, S, of organ at distance r. | fraction of ray's energy absorbed in passing through a thickness, dr, of tissue | total energy of each ray [ ergs ] | | |
|---|---|---|---|---|
| ... total number of rays that pass through the surface, S. | energy [ erg ] absorbed in thickness dr of tissue per photon | . . . . . . . . . . . | grams of tissue in thickness dr behind surface, S. |
| | ... total energy absorbed in thickness dr from all photons | . . . . . | total ergs absorbed per gram |

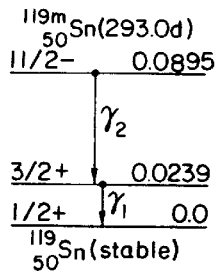

FIG. 13

Decay Scheme of $^{119m}$Sn

50 – TIN – 119M

HALFLIFE = 293 DAYS
DECAY MODE(S): IT

17 – MAR – 79

| RADIATION | y(i) (Bq-s)$^{-1}$ | E(i) (MeV) | y(i) x E(i) |
|---|---|---|---|
| $\gamma$ 1 | 1.63E-01 | 2.387E-02 | 3.89E-03 |
| ce - L$_1$, $\gamma$ 1 | 6.12E-01 | 1.941E-02 | 1.19E-02 |
| ce - L$_2$, $\gamma$ 1 | 5.06E-02 | 1.971E-02 | 9.98E-04 |
| ce - L$_3$, $\gamma$ 1 | 1.41E-02 | 1.994E-02 | 2.81E-04 |
| ce - M, $\gamma$ 1 | 1.32E-01 | 2.316E-02* | 3.06E-03 |
| ce - N$^+$, $\gamma$ 1 | 2.85E-02 | 2.387E-02* | 6.80E-04 |
| $\gamma$ 2 | 1.94E-04 | 6.566E-02 | 1.27E-05 |
| ce - K, $\gamma$ 2 | 3.22E-01 | 3.646E-02 | 1.17E-02 |
| ce - L$_1$, $\gamma$ 2 | 1.53E-01 | 6.120E-02 | 9.34E-03 |
| ce - L$_2$, $\gamma$ 2 | 3.35E-02 | 6.150E-02 | 2.06E-03 |
| ce - L$_3$, $\gamma$ 2 | 3.37E-01 | 6.173E-02 | 2.08E-02 |
| ce - M, $\gamma$ 2 | 1.24E-01 | 6.495E-02* | 8.04E-03 |
| ce - N$^+$, $\gamma$ 2 | 3.10E-02 | 6.566E-02* | 2.04E-03 |
| K$\alpha_1$ X-ray | 1.48E-01 | 2.527E-02 | 3.74E-03 |
| K$\alpha_2$ X-ray | 7.90E-02 | 2.504E-02 | 1.98E-03 |
| K$\beta_1$ X-ray | 2.74E-02 | 2.849E-02 | 7.80E-04 |
| K$\beta_2$ X-ray | 8.14E-03 | 2.911E-02 | 2.37E-04 |
| K$\beta_3$ X-ray | 1.41E-02 | 2.844E-02 | 4.02E-04 |
| L$\alpha$ X-ray | 5.51E-02 | 3.443E-03* | 1.90E-04 |
| L$\beta$ X-ray | 5.06E-02 | 3.737E-03* | 1.89E-04 |
| L$\gamma$ X-ray | 7.36E-03 | 4.309E-03* | 3.17E-05 |
| Auger-KLL | 3.03E-02 | 2.082E-02* | 6.31E-04 |
| Auger-KLX | 1.34E-02 | 2.429E-02* | 3.25E-04 |
| Auger-LMM | 8.97E-01 | 2.808E-03* | 2.52E-03 |
| Auger-LMX | 4.31E-01 | 3.488E-03* | 1.50E-03 |
| Auger-LXY | 5.68E-02 | 3.947E-03* | 2.24E-04 |
| Auger-MXY | 2.64E-00 | 5.938E-04* | 1.57E-03 |

| | |
|---|---|
| LISTED X, $\gamma$ AND $\gamma$ ± RADIATIONS | 1.15E-02 |
| OMITTED X, $\gamma$ AND $\gamma$ ± RADIATIONS** | 1.42E-05 |
| LISTED $\beta$, ce AND Auger RADIATIONS | 7.77E-02 |
| OMITTED $\beta$, ce AND Auger RADIATIONS** | 7.14E-05 |
| LISTED RADIATIONS | 8.91E-02 |
| OMITTED RADIATIONS** | 8.55E-05 |

\* AVERAGE ENERGY (MeV)
\*\* EACH OMITTED TRANSITION CONTRIBUTES
  <0.100% TO Σy(i) x E(i) IN ITS CATEGORY.
TIN - 199 DAUGHTER IS STABLE.

FIG. 14
Decay Scheme of $^{121m}$Sn

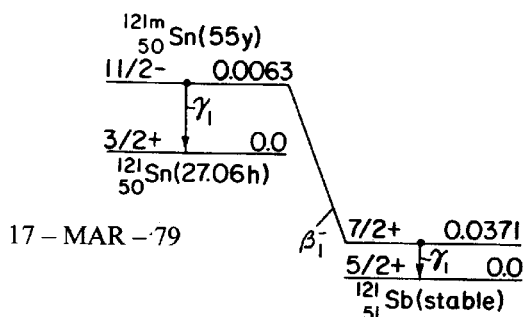

HALFLIFE = 55 YEARS
DECAY MODE(S): $\beta^-$, IT

17 – MAR –79

| RADIATION | y(i) (Bq-s)$^{-1}$ | E(i) (MeV) | y(i) × E(i) |
|---|---|---|---|
| $\beta^-$ 1 | 2.24E-01 | 1.207E-01* | 2.70E-02 |
| $\gamma$ 1 | 1.85E-02 | 3.715E-02 | 6.87E-04 |
| ce - K, $\gamma$1 | 1.76E-01 | 6.659E-03 | 1.17E-03 |
| ce - L$_1$, $\gamma$1 | 2.08E-02 | 3.245E-02 | 6.77E-04 |
| ce - L$_2$, $\gamma$1 | 1.64E-03 | 3.277E-02 | 5.38E-05 |
| ce - M, $\gamma$1 | 4.51E-03 | 3.638E-02* | 1.64E-04 |
| ce - N$^+$, $\gamma$1 | 1.06E-03 | 3.715E-02* | 3.92E-05 |
| K$\alpha_1$ X-ray | 8.15E-02 | 2.636E-02 | 2.15E-03 |
| K$\alpha_2$ X-ray | 4.36E-02 | 2.611E-02 | 1.14E-03 |
| K$\beta_1$ X-ray | 1.52E-02 | 2.973E-02 | 4.53E-04 |
| K$\beta_2$ X-ray | 4.60E-03 | 3.040E-02 | 1.40E-04 |
| K$\beta_3$ X-ray | 7.86E-03 | 2.968E-02 | 2.33E-04 |
| L$\alpha$ X-ray | 6.29E-03 | 3.604E-03* | 2.27E-05 |
| L$\beta$ X-ray | 5.77E-03 | 3.901E-03* | 2.25E-05 |
| Auger-KLL | 1.56E-02 | 2.167E-02* | 3.37E-04 |
| Auger-KLX | 6.98E-03 | 2.531E-02* | 1.77E-04 |
| Auger-LMM | 1.11E-01 | 2.960E-03* | 3.28E-04 |
| Auger-LMX | 5.48E-02 | 3.685E-03* | 2.02E-04 |
| Auger-MXY | 3.25E-01 | 6.490E-04* | 2.11E-04 |
| ce - L$_3$, $\gamma$1 | 4.86E-01 | 2.361E-03* | 1.15E-03 |
| ce - M, $\gamma$1 | 2.26E-01 | 5.576E-03* | 1.26E-03 |
| ce - N$^+$, $\gamma$1 | 5.80E-02 | 6.290E-03* | 3.65E-04 |
| L$\alpha$ X-ray | 2.41E-02 | 3.443E-03* | 8.29E-05 |
| L$\beta$ X-ray | 3.85E-03 | 3.889E-03* | 1.50E-05 |
| Auger-LMM | 3.00E-01 | 2.736E-03* | 8.21E-04 |
| Auger-LMX | 1.44E-01 | 3.414E-03* | 4.91E-04 |
| Auger-LXY | 1.91E-02 | 3.875E-03* | 7.41E-05 |
| Auger-MXY | 9.95E-01 | 6.049E-04* | 6.02E-04 |

| | |
|---|---|
| LISTED X, $\gamma$ AND $\gamma$ ± RADIATIONS | 4.94E-03 |
| OMITTED X, $\gamma$ AND $\gamma$ ± RADIATIONS** | 1.09E-05 |
| LISTED $\beta$, ce AND Auger RADIATIONS | 3.52E-02 |
| OMITTED $\beta$, ce AND Auger RADIATIONS** | 9.52E-05 |
| LISTED RADIATIONS | 4.01E-02 |
| OMITTED RADIATIONS** | 1.06E-04 |

\* AVERAGE ENERGY (MeV)
\*\* EACH OMITTED TRANSITION CONTRIBUTES <0.100% TO $\Sigma$y(i) × E(i) IN ITS CATEGORY.
ANTIMONY-121 DAUGHTER, YEILD 2.24E-01, IS STABLE.
TIN – 121 DAUGHTER, YEILD 7.76E-01, IS RADIOACTIVE.

FIG. 15

Decay Scheme of $^{125}$I

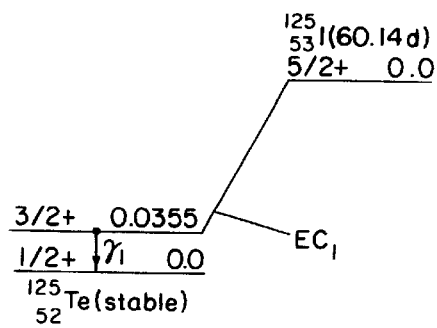

53 – IODINE – 125

HALFLIFE = 60.14 DAYS  
DECAY MODE(S): EC

17 – JUN – 78

| RADIATION | y(i) (Bq-s)$^{-1}$ | E(i) (MeV) | y(i) x E(i) |
|---|---|---|---|
| $\gamma$ 1 | 6.67E-02 | 3.549E-02 | 2.37E-03 |
| ce - K, $\gamma$ 1 | 8.03E-01 | 3.678E-03 | 2.95E-03 |
| ce - L$_1$, $\gamma$ 1 | 9.52E-02 | 3.055E-02 | 2.91E-03 |
| ce - L$_2$, $\gamma$ 1 | 7.64E-03 | 3.088E-02 | 2.36E-04 |
| ce - L$_3$, $\gamma$ 1 | 1.91E-03 | 3.115E-02 | 5.96E-05 |
| ce - M, $\gamma$ 1 | 2.09E-02 | 3.467E-02* | 7.25E-04 |
| ce - N$^+$, $\gamma$ 1 | 4.96E-03 | 3.549E-02* | 1.76E-04 |
| K$\alpha_1$ X-ray | 7.41E-01 | 2.747E-02 | 2.04E-02 |
| K$\alpha_2$ X-ray | 3.98E-01 | 2.720E-02 | 1.08E-02 |
| K$\beta_1$ X-ray | 1.40E-01 | 3.100E-02 | 4.34E-03 |
| K$\beta_2$ X-ray | 4.30E-02 | 3.171E-02 | 1.36E-03 |
| K$\beta_3$ X-ray | 7.20E-02 | 3.094E-02 | 2.23E-03 |
| K$\beta_5$ X-ray | 1.44E-03 | 3.124E-02 | 4.51E-05 |
| L$\alpha$ X-ray | 6.14E-02 | 3.768E-03* | 2.31E-04 |
| L$\beta$ X-ray | 5.93E-02 | 4.092E-03* | 2.43E-04 |
| Auger-KLL | 1.32E-01 | 2.254E-02* | 2.97E-03 |
| Auger-KLX | 5.97E-02 | 2.635E-02* | 1.57E-03 |
| Auger-KXY | 7.95E-03 | 3.013E-02* | 2.40E-04 |
| Auger-LMM | 1.01E-00 | 3.086E-03* | 3.11E-03 |
| Auger-LMX | 5.17E-01 | 3.855E-03* | 1.99E-03 |
| Auger-LXY | 7.33E-02 | 4.386E-03* | 3.21E-04 |
| Auger-MXY | 2.99E-00 | 6.989E-04* | 2.09E-03 |
| $\Delta$E | 6.22E-01 | 5.577E-05* | 3.47E-05 |

| | |
|---|---|
| LISTED X, $\gamma$ AND $\gamma$ ± RADIATIONS | 4.20E-02 |
| OMITTED X, $\gamma$ AND $\gamma$ ± RADIATIONS** | 4.58E-05 |
| LISTED $\beta$, ce AND Auger RADIATIONS | 1.94E-02 |
| LISTED RADIATIONS | 6.14E-02 |
| OMITTED RADIATIONS** | 4.58E-05 |

\* AVERAGE ENERGY (MeV)  
\*\* EACH OMITTED TRANSITION CONTRIBUTES <0.100% TO $\Sigma$y(i) x E(i) IN ITS CATEGORY.  
TELLURIUM-125 DAUGHTER IS STABLE.

The energy-level scheme and resultant spectrum for Magnetic hyperfine splitting of an $I_g = 1/2 - I_e = 3/2$ transition. The relative splittings are scaled in accord with the magnetic moments of $^{119}$Sn ; $\mu_g = 1.04\mu_N$ and $\mu_e = +0.67\mu_N$. The line intensity ratios of 3 : 2 : 1 : 1 : 2 : 3 are appropriate to a polycrystalline absorber.

The effect of orientation upon the relative line Intensities of a magnetic hyperfine splitting and a quadrapole splitting of a $3/2 \to 1/2$ transition in an orientation absorber with a unique principal axis system.

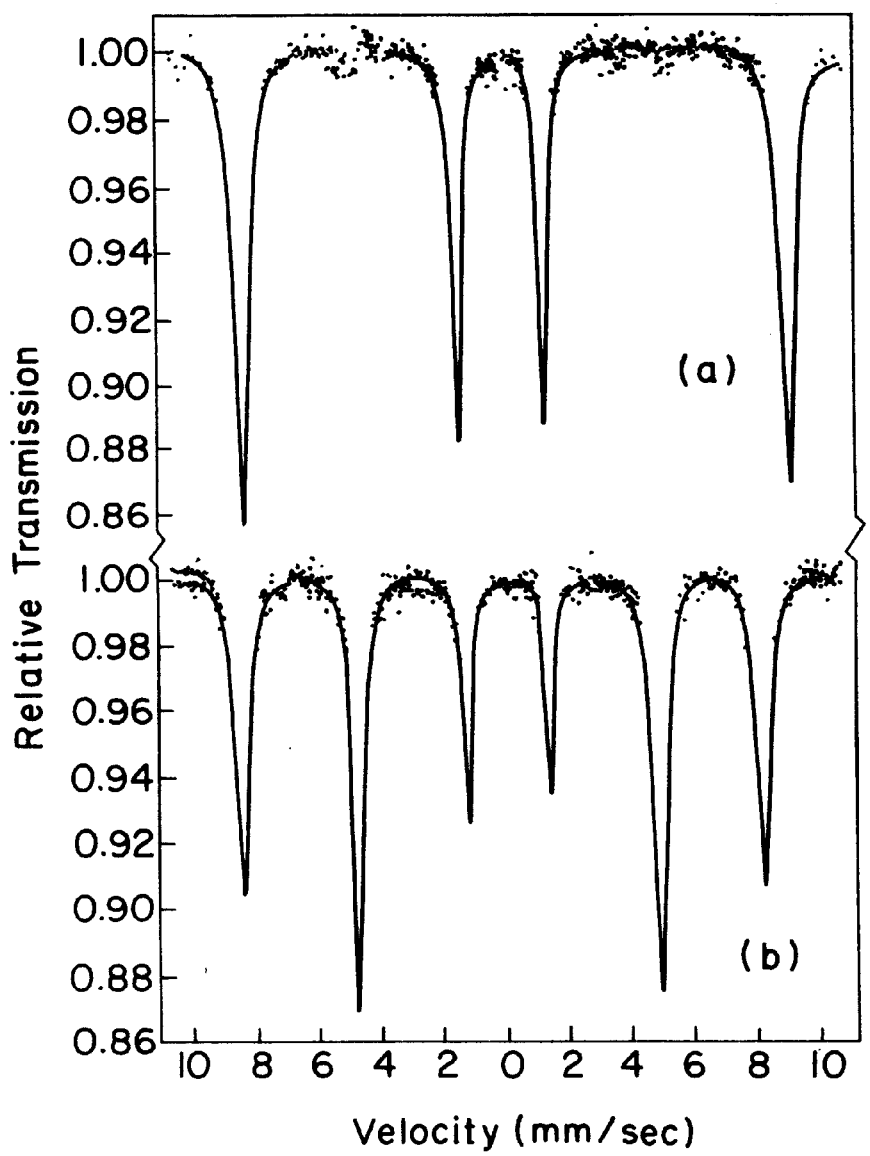
Spectra from a single crystal of α - $Fe_2O_3$ cut parallel to the basal plane and with the gamma ray direction along 111 : (a) at 80° K and (b) at 300° K. A source of $^{57}Co$ in Pt was used.
FIG. 18A,B

PHARMACEUTICALS PROVIDING DIAGNOSIS AND SELECTIVE TISSUE NECROSIS USING MOSSBAUER ABSORBER ATOM

CROSS REFERENCE TO RELATED APPLICATIONS

This application is a continuation of Ser. No. 07/950,973, filed Sep. 23, 1992, now abandoned, which is a continuation of Ser. No. 07/055,591, filed May 28, 1987, now abandoned, which is a continuation-in-part of Ser. No. 06/849,046, filed Apr. 7, 1986, now U.S. Pat. No. 4,815,448, which is a continuation-in-part of Ser. No. 06/713,448, filed Mar. 19, 1985, now U.S. Pat. No. 4,815,447.

FIELD OF THE INVENTION

The present invention relates to pharmaceuticals and apparatus to implement the Mossbauer effect for diagnostic and therapeutic purposes.

BACKGROUND OF THE INVENTION

In the treatment of tumors by ionizing radiation, typically X-rays or gamma rays are used. The ideal in radiation therapy of malignant disease is achieved when the tumor is completely eradicated, and the surrounding normal tissue, in the treated volume, shows little or no evidence of structural or functional injury. The important factor in successful treatment is the difference in radiosensitivity of neoplastic and normal cells. All tissues, normal and neoplastic, are affected by radiation so that radiosensitivity is a relative term. The basic consideration of radiation therapy is that cells that are actively proliferating or that cells which are of a primitive type are more sensitive than normal tissue so that there is usually a considerable margin between doses that are damaging to neoplastic and to normal cells. If this is the case, then a multifraction dose schedule decreases the size of the tumor over time while permitting time between doses for normal tissue to recover. A constant fraction of tumor cells are killed with each treatment, and theoretically the tumor can be completely eliminated with a sufficient number of treatments. However, normal tissue has a memory of its accumulated radiation dose such that a threshold to the total dose acquired over the patient's history is eventually reached. Exceeding this threshold results in unacceptable side effects. Thus, the tumor volume must be reduced sufficiently before the threshold is reached or the cancer is incurable by this modality of therapy.

SUMMARY OF THE INVENTION

The present invention is pharmaceuticals, apparatus, and a process which provides diagnosis, therapy and other biological effects by use of highly selective absorption of radiation called the Mossbauer effect. Mossbauer absorption which is exploited for diagnosis and therapy by the present invention is completely analogous to optical absorption. For purposes of the present application, Mossbauer resonance is synonymously defined as an energy and a frequency which are interchangeable by the relationship:

$$E = h\nu = hc/\lambda \qquad (1)$$

For optical absorption, the ultimate source of radiation consists of excited atoms or molecules which decay to the ground state. The radiation, after being suitably monochromatized by a prism or diffraction grating, is incident upon the sample, and the intensity of the beam which is transmitted through the sample (absorber) varies as a function of the frequency as the photons of energy equivalent to electronic, vibrational, rotational, and translational transitions are absorbed. In Mossbauer absorption, the source comprises excited nuclei in appropriate highly bonding surroundings. The nuclei, in decaying to their ground state, emit gamma radiation that is highly monochromatic. In fact, the gamma ray line can be so narrow that its frequency may be shifted significantly by incorporating the source or absorber in a mass driver oscillating at moderate velocities to produce a Doppler effect. The velocity of the mass driver which provides a Doppler shift to the gamma ray photons functions analogously to the dispersion device in optical absorption. By varying the driving velocity, a resonance system can be driven by the emitted gamma photons with regard to the nuclear energy transitions of the sample (absorber).

As part of the present invention, useful application of the Mossbauer effect in living tissue is provided by an administered pharmaceutical containing a Mossbauer isotope as the absorber. The pharmaceutical is resonantly excited by the gamma photons provided by this apparatus where the gamma ray energy, polarization and propagation direction are resonant with the nuclear transitions of the isotope in the target tissue, from which the surrounding nontarget tissue differs significantly in resonance conditions to achieve an enhanced therapeutic or diagnostic function and minimum effects in the nontarget tissue.

As a further aspect of the present invention the resonant (Mossbauer) absorption of gamma rays by nuclei of the administered isotopes at the target tissue, provides a specific, lethal release of energy to a susceptible biological target such as the DNA of the target tissue as part of a therapeutic process. Alternatively, the present invention provides diagrams by monitoring the release of nonlethal energy, as described in detail, below. An acronym for Mossbauer Isotopic Resonant Absorption of Gamma Emission, hereafter, MIRAGE, is created, and the corresponding therapy and pharmaceuticals are disclosed as MIRAGE therapy and MIRAGE pharmaceuticals.

The MIRAGE pharmaceuticals contain Mossbauer absorber isotopes and bind to a target tissue to become immobilized, permitting Mossbauer nuclear resonant absorption of gamma radiation in the vicinity of the target tissue. The excitation is by a radiation source, the apparatus of the invention, at the corresponding resonant Mossbauer absorption frequency of selected tissue having received the administered pharmaceutical where excitation effects nuclear transitions to cause selective energy absorption in the selected target tissue. For diagnostic purposes, de-excitation fluorescence of the isotope is monitored with gamma ray scanning equipment. For therapeutic purposes, the energy is converted into particle radiation by the Mossbauer isotope at the target tissue by internal conversion followed by an Auger cascade which results in damage to a susceptible biological target such as radiolysis of DNA resulting in lethal double strand breaks in the DNA molecules of the target tissue.

Tissue selectivity is achieved by causing the Mossbauer effect to occur to a greater extent in the selected target tissue than the nontarget tissue. One aspect of the present invention providing selectivity is by administering pharmaceuticals which are selectively taken up by the selected tissue. Alternate embodiments of the present invention selectively control Mossbauer resonant absorption by control of the conditions for resonance of gamma ray energy, polarization, and propagation direction, wherein pharmaceuticals when in the vicinity of selected versus nonselected tissue, have a differential of one or more such conditions. Such conditions are made different by magnetic fields or ultrasonic power which are applied, effecting an absorption differential for selected versus nonselected tissue. Mossbauer absorption at the target tissue is provided by shifting the source frequency to conform to that of the MIRAGE isotope in the vicinity of the target tissue. Alternately the absorption characteristics of the MIRAGE isotope is controlled to match the imparted radiation at the site of the target tissue.

Apparatus providing the selectively shifted radiation comprises a Mossbauer source supported by a mass drive or ultrasonic transducer drive which can suitably "tune" the emitted radiation to the proper Mossbauer absorption frequency by imparting a Doppler frequency shift or by shifting the energy of emission side bands, respectively. In addition, the apparatus includes means to polarize the emission and possesses means to produce external magnetic fields and an ultrasonic beam to effect selective absorption by changing the gamma ray energy and/or polarization and propagation direction conditions to achieve resonance in the absorber pharmaceutical selectively.

In addition, the present invention includes apparatus to separately and controllably polarize both the emission radiation and the absorber pharmaceutical at the target tissue to achieve the desired controlled absorption. Alternate embodiments of the apparatus according to the present invention provide selectively controlled external magnetic fields at the target tissue to effect selective absorption by changing the gamma ray energy and/or polarization and propagation direction conditions to achieve resonance in the MIRAGE absorber pharmaceutical. The Apparatus, Systems, Compounds, Methods, and specifications of use are described in detail below.

BRIEF DESCRIPTION OF THE DRAWINGS

These and other features of the present invention will be better understood by reading the following detailed description taken together with the drawing, wherein:

FIG. 10 is a drawing of the MIRAGE pharmaceutical 12/29/w.

FIG. 11 is the decay scheme of $^{57}Co$.

FIG. 12 is an equation to calculate radiation dose.

FIG. 13 is the decay scheme of $^{119}Sn$.

FIG. 14 is the decay scheme of $^{121m}Sm$.

FIG. 15 is a decay scheme of $^{125}I$.

FIGS. 18a and b are the spectra from a single crystal of $\alpha$-$Fe_2O_3$ cut parallel to the basal plane with the gamma ray direction along 111.

FIG. 18a is the spectra of FIG. 18 at 80° K.

FIG. 18b is the spectra of FIG. 18 at 300° K.

DETAILED DESCRIPTION OF THE INVENTION

Figure 1:
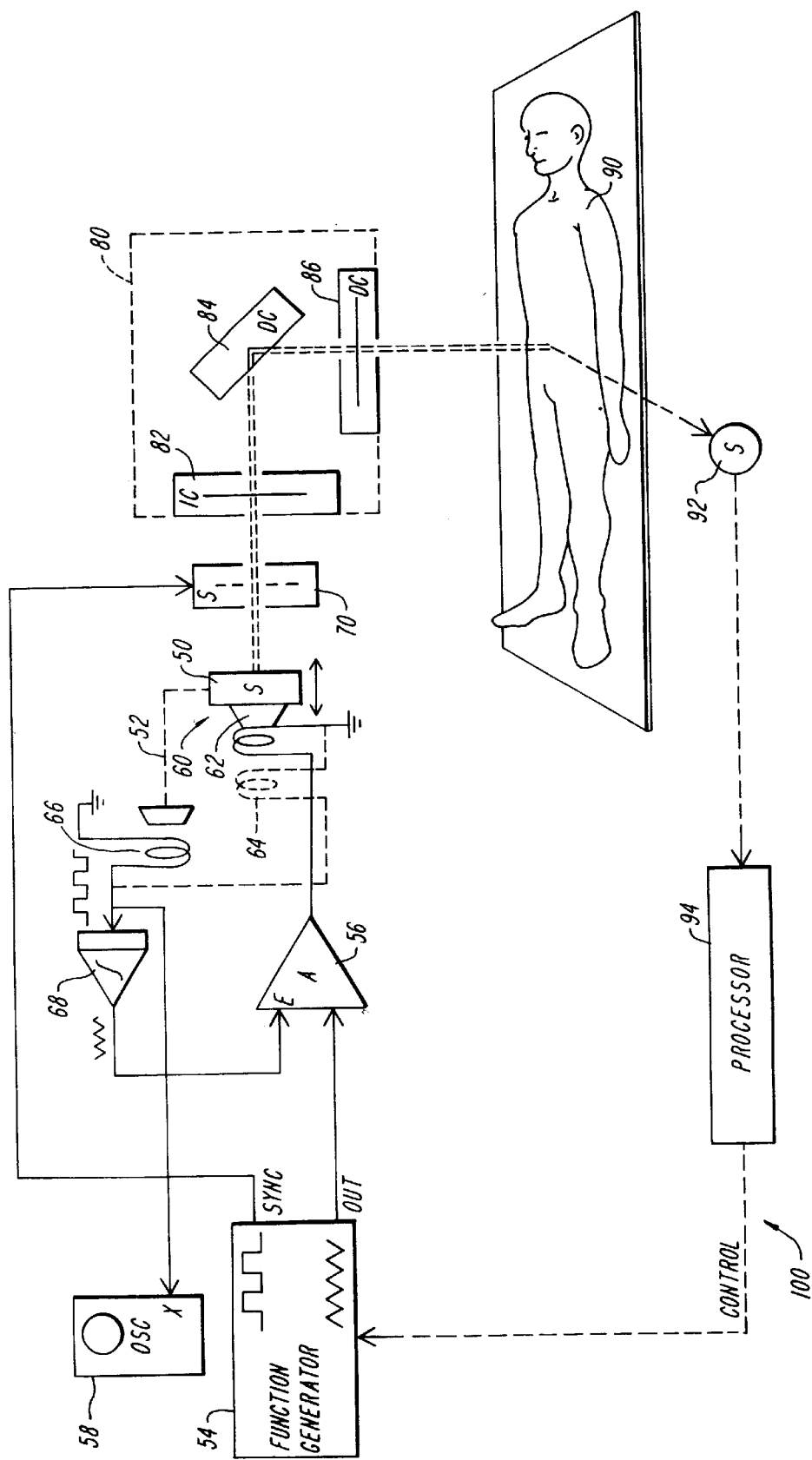
FIG. 1 is one embodiment of the system apparatus of the present invention.

The present invention includes the process of producing pharmaceuticals having desired Mossbauer nuclear parameters such that they possess physical and chemical properties which permit the Mossbauer phenomenon to be selectively effected in the target tissue. The application includes administering the pharmaceuticals and producing gamma radiation of the proper polarization, propagation direction, and energy with the radiation source to cause selective resonant absorption in the target tissue. The present invention also includes producing magnetic fields or an ultrasonic beam both of selected strength and direction with the apparatus of the radiation source to effect selective gamma ray absorption in the target tissue via the Mossbauer effect.

The pharmaceuticals of the present invention and the process of producing the pharmaceuticals is discussed first, which is followed by the apparatus used in combination with selected pharmaceuticals to effect the Mossbauer absorption in a biological target as a process of the invention to provide a therapeutic or diagnostic function. The latter, apparatus, provides a monochromatic source of gamma rays having an emission frequency or energy at or near the (or substantially monochromatic over the range of frequencies where Mossbauer absorption may occur in irradiated tissue) nuclear transitions of one or more Mossbauer atoms incorporated in the pharmaceuticals. Subsequently discussed are the features of the present invention wherein the energy which excites the nuclear transition is released as light which can be recorded for diagnostic purposes, or the energy is converted into charged particles or reactive species which irreversible damage a biological target to effect a therapeutic function.

Selectivity in treatment or diagnosis is obtained by causing the gamma ray absorption to occur with the Mossbauer absorber atoms of the pharmaceuticals in the target tissue to a greater extent than in the nontarget tissue due to differential uptake of the pharmaceutical or a differential in the conditions of the source gamma rays needed to achieve resonant absorption by the absorbers including a difference in energy and/or a difference in polarization and gamma ray propagation direction relative to the direction of the magnetic or quadrapole moments of the absorber Mossbauer atoms in the pharmaceuticals. Differential uptake involves physical, chemical, and biological properties of the pharmaceuticals which influence its uptake by cells.

The differential resonance conditions of gamma ray energy and/or polarization and propagation direction are provided by different chemical and/or physical interactions of the Mossbauer atoms of the pharmaceuticals with the environment in which they are present in target versus nontarget tissue. Furthermore, magnetic fields or an ultrasonic beam are selectively applied to the target area in such a fashion to produce a differential of these resonance conditions at different locations. Therefore, treatment is carried out by irradiating the selected tissue with gamma radiation of the proper energy and polarization and gamma ray propagation direction to match the conditions for resonant absorption by the Mossbauer absorber isotope atoms of the pharmaceutical molecules present in the target selected tissue.

Implementation of the process for making MIRAGE pharmaceuticals involves selecting an atom responsive to the Mossbauer effect at a convenient frequency, selecting the structure of the molecule to which the Mossbauer responsive atom (Mossbauer Atom) is attached, selecting the type of bond to form between the Mossbauer atom and the remainder of the pharmaceutical and the position at which the Mossbauer atom is attached. Mossbauer nuclear parameters (i.e., Table 8, includes absorption line width, recoil energy, nuclear magnetic moment, internal conversion coefficient, X-ray energy, magnetic quantum numbers of the ground and excited state) are used in calculations as demonstrated in the Theoretical Section, below, to perform the following steps in the design of the pharmaceutical:

1. A Mossbauer atom is selected such that it possesses chemical reactivity to form a bond of the nature described below under 3, a large cross-section for absorption of resonant gamma radiation with de-excitation primarily by particle production or fluorescence for the purposes of therapy and diagnostic imaging, respectively, a low recoil energy which is smaller than the vibrational energy of the bond between the Mossbauer atom and the remainder of the pharmaceutical molecule, a large nuclear moment which interacts with an imposed magnetic field to lift the degeneracy of existing magnetic sublevels to a significant extent that spatial discrimination with regard to the occurrence of the Mossbauer effect can be realized by changing the magnetic field direction and magnitude to change the resonance conditions of gamma ray energy and/or polarization and propagation direction, and a small absorption. line width so that aforementioned discrimination can be realized over small spatial dimensions, and so that an ultrasonic means of discrimination of shifting the Mossbauer absorption energy as described in the Theoretical Section can be realized with low MHz frequencies.

2. A molecular structure to which the Mossbauer atom is to be bound is selected such that it possesses the ability to also be bound to the selected biological target to immobilize the Mossbauer atom to prevent degradation of the Mossbauer effect by excitation of translational modes of the pharmaceutical molecule, that in certain cases is selectively taken up by the selected tissue, and that in certain cases interacts with the environment of the selected tissue differentially relative to nonselected tissue to cause different conditions to achieve resonance between these tissues.

3. The bond between the Mossbauer atom and the remainder of the pharmaceutical molecule is selected such that it possesses vibrational modes which are not excited by the recoil energy of the absorbed gamma ray; thus, the Mossbauer effect is not degraded by this mechanism.

4. The bonding position of the Mossbauer atom or functionality to the remainder of the pharmaceutical molecule has no effect on the binding affinity of the latter for the biological target.

The photon flux necessary for effective treatment is calculated where variables for each of the afore mentioned design parameters are included in the calculation, and the strength and direction of imposed magnetic fields to obtain selectivity are also calculated. Both types of calculations are demonstrated in the Theoretical Section.

The pharmaceutical possesses physical and/or chemical properties which permits it to bind sufficiently tightly to a massive biological target so that the effective mass of the Mossbauer atom which is incorporated in the pharmaceutical is the mass of the biological target. The effective mass is sufficient to prevent excitation of translational modes of the Mossbauer atom by the recoil energy of the absorbed gamma ray. Furthermore, the chemical bond between the Mossbauer atom and the remainder of the pharmaceutical has a bond energy that precludes excitation of vibrational modes of the bond by the recoil energy of the absorbed gamma ray. The pharmaceutical contains at least one Mossbauer atom which has a large cross-section for absorption and the atom de-excites primarily by fluorescence in the case of imaging pharmaceuticals and the atom converts the excitation energy primarily into charged particles and reactive species in the case of therapeutic pharmaceuticals. Also, the pharmaceutical possess physical and chemical properties so that it is selectively taken up by selected cells, or it possesses Mossbauer nuclear parameters which permit the nucleus of the Mossbauer atom to interact with an imposed magnetic field with a resultant change in the resonance conditions of gamma ray energy and/or polarization and propagation direction to a sufficient degree that selectivity of target versus nontarget tissues can be achieved by this interaction.

A further feature of the present invention is the use of selected pharmaceuticals and apparatus described herein in combination to apply the Mossbauer effect to treat selected tissues. Treatment includes providing selective uptake of a specific pharmaceutical by the target tissue, and irradiation of the target tissue with selected energy (frequency) radiation produced by the apparatus of one embodiment. The apparatus may also apply a magnetic field to cause the resonance conditions of gamma ray energy and polarization and propagation direction necessary to produce nuclear transitions in the absorber, to match these conditions of gamma rays produced by the source for the case of a stationary source (non-Doppler shifted, nonultrasonically driven). And, where the applied pharmaceutical is present in nonselected tissue, selectivity in treatment is provided by the imposition of fields by the apparatus to force differential resonance conditions of gamma ray energy and/or polarization and gamma ray propagation direction for resonant nuclear absorption by the Mossbauer absorber atoms of the target tissue to provide treatment to a tissue selected area or volume.

Magnetic fields are applied to the body where the field magnitude and direction change rapidly as a function of position in the space permeated by the field. The gamma rays of the source are made to match the gamma ray energy, polarization and propagation direction conditions for resonant nuclear absorption by the Mossbauer atoms of the pharmaceuticals present in the target tissue. Selectivity of treatment in this case is achieved because the conditions for nuclear resonant absorption in nonselected tissue through which the gamma rays travel to the selected tissue are different from those of the selected tissue.

The radiation of energy in resonance with the selected isotope and of proper polarization and propagation direction is produced by the apparatus which includes a selectable energy source such as a synchrotron source or a Mossbauer source which corresponds to the selected isotope (corresponding sources to selected absorber isotopes to be incorporated into pharmaceuticals appear in Table 7). The Mossbauer source is incorporated into a mass drive which can suitably tune the emitted radiation to the proper Mossbauer absorption frequency by imparting a Doppler shift, or the Mossbauer source can be adhered to a ultrasonic drive which creates emission side bands of energy which is selectable according to the ultrasonic driving frequency as described in the Theoretical Section, or magnetic fields may be applied to the target tissue such that the energy conditions for resonant absorption by the selected absorber isotope of the pharmaceutical are forced to match those of the stationary source. In addition, the apparatus includes a polarizing element, to polarize the emission. Polarized gamma rays are obtained by three methods: magnetized ferromagnetic sources, quadrapole split sources, or filter techniques. In addition, the apparatus possesses means to produce external magnetic fields and ultrasonic beams to change the gamma ray energy and/or polarization and propagation direction conditions to achieve resonant absorption in the absorber atoms of the pharmaceuticals to impart tissue selectivity according to the present invention. Magnetic fields and ultrasonic beams are produced by powerful surface coils such as those used in magnetic resonance imaging and piezo-electric transducers and transducer arrays such as those used in ultrasonic imaging, respectively. Such magnetic field producing means and ultrasonic beam producing means are described below in the Apparatus Section.

The process of providing selectivity by imparting magnetic fields with the apparatus involves providing a magnetic field in space which contains the selected tissue. Thus, spatial discrimination with regard to the occurrence of the Mossbauer effect can be realized by selectively changing the field direction and strength to change the resonance conditions of gamma ray energy and/or polarization and propagation direction in a specified area or volume of tissue. The Mossbauer atoms of the pharmaceuticals possess magnetic moments which interact with the imposed magnetic fields to cause the effects of creation of nondegenerate magnetic sublevels and alignment of the nuclear moments along the direction of the field lines with a concomitant alignment of the tissue resonance. The lifting of the magnetic sublevel degeneracy changes the energy for resonant absorption by the Mossbauer atoms and is a function of the imposed magnetic field strength and the magnetic moment of the particular absorber atoms. Magnetic fields which change rapidly in strength and time (for pulsed fields) are used to create a selective situation where the energy for resonance changes rapidly along the field gradient; thus, the energy of the source can be conformed to the energy for resonant absorption by the absorbers at the selected tissue site such that the resonant condition is satisfied only over the volume of the selected site. The alignment effect results in a dependency on the angle between the alignment direction of the nuclear moments of the absorber atoms and the propagation direction and polarization properties of gamma rays for resonant absorption by the absorbers to occur. Fields which change rapidly in vector direction in space and time (for pulsed fields) are used to create a rapidly changing spatial distribution of populations of atoms with the magnetic moments aligned in different directions. Thus, a magnetic field is provided wherein the magnetic moments of all of the Mossbauer atoms in the nonselected tissue through which the gamma ray travels are in a nonresonant orientation, and the Mossbauer atoms in the selected tissue are in a resonant orientation. Thus, selectivity is achieved by this alignment effect according to the transparency of the nonselected tissue to the gamma rays and absorption by the selected tissue.

The process of treatment involves using the pharmaceuticals and apparatus in combination to cause the Mossbauer effect to occur to a greater extent in the selected tissue than in the nonselected tissue. The tissue is irradiated with gamma radiation of energy and polarization and propagation direction resonant with the nuclear transitions of the selected tissue. Selectivity is achieved because the drug is uptaken by the selected tissue to a greater extent than the interposed nonselected tissue through which the gamma ray propagates. Or, a magnetic field of rapidly divergent strength and direction is applied, or an ultrasonic beam is applied. For the ultrasonic case, the process of effecting selectivity by causing an ultrasonic beam to intersect the administered gamma ray beam at the selected tissue site involves producing a component of ultrasonic motion of the Mossbauer absorber nuclei in the selected tissue in the direction of the gamma ray beam to produce absorption side bands of energy different from those of nonselected tissue through which the gamma rays resonant with a selected side band propagate. The production of absorption side bands by driving at ultrasonic frequencies is described in the Theoretical Section. In the magnetic case, the phenomenon of the magnetic field strength dependence of the lifting of the degeneracy of magnetic sublevels of nuclear transitions and nuclear magnetic moment alignment with the magnetic field lines and the concomitant dependency for resonant absorption on the angle between the nuclear magnetic moment and the gamma ray propagation direction and polarization of the gamma ray can be used to force a matching set of conditions by the apparatus between the source and the Mossbauer absorber atoms in the pharmaceuticals in the selected tissue. The parameters which are changed to achieve this result are the energy of the source gamma rays (e.g. by changing the velocity of the mass drive), the polarization of the source gamma rays (e.g. by changing the direction of the source polarization magnetic field in the case of a ferromagnetic source), the magnetic field strength gradient (e.g. by changing the current in the surface coils which give rise to the field and the distribution of the coils about the treatment volume), and the propagation direction of the gamma ray by changing the relative position of the source of magnetic fields and the source of gamma rays.

If the set of parameters which produce resonance selectively in the selected tissue are known (for example from calculations such as those demonstrated in the Theoretical Section or from prior experiments), then the therapy is carried out in an open loop fashion. For example, for the case where the drug is selectively uptaken by the selected tissue or has a unique energy for absorption in the selected tissue, the resonance energy of the source and absorber are forced to match each other by changing the energy of the source to match the energy of the nuclear transitions of the absorbers of the pharmaceutical, or the energy of the transitions of the absorber are changed to match that of the source. In the former case, the velocity of the mass drive or the frequency of the ultrasonic transducer can be adjusted, and in the latter case, magnetic fields can be used to change the energy of the absorber nuclear transitions. Selectivity can be achieved where the drug is distributed in nonselected tissue by use of a magnetic field of strong field gradient so that the energy of resonance is only met in a small spatial region. Such a magnetic field could be applied, and the energy of the source adjusted to match that required for resonance in the selected tissue. This mode of achieving selectivity could also be used in conjunction with a polarization mode where the Mossbauer nuclei of the pharmaceuticals of the selected tissue are aligned with an imposed magnetic field in a resonant direction with respect to the gamma ray propagation direction and polarization, and the interposed tissue is made transparent by orienting the nuclei in a nonresonent direction. An additional mode of achieving selectivity is to impose a narrow ultrasonic beam which intersects the administered gamma ray beam to induce a component of ultrasonic motion of the Mossbauer absorber nuclei at the selected tissue site to create absorption side bands of unique energy equal to the energy of the administered gamma rays as described in the Apparatus and Theoretical Sections.

If the parameters to achieve resonance between the apparatus and absorbers are unknown, then the afore mentioned modes of treatment are carried out in a closed loop fashion using gamma ray fluorescence. All Mossbauer nuclei undergo fluorescent emission to a certain extent after resonantly absorbing gamma rays. This phenomenon is used to detect where resonance is achieved. Fluorescence occurs at a continuum of angles, and a bank of detectors surrounding the treatment volume is used to detect the source of fluorescence, as described below. Thus, the position of the source of fluorescence is used in a feedback loop which feeds into a control system which changes the magnetic field strength and direction; ultrasonic beam frequency, direction and power; and gamma ray energy, polarization, and propagation direction until the source of fluorescence is the selected tissue. Treatment is then carried out to the level of an absorbed dose which is known from calculation or past experience. A representative calculation of an effective photon flux for treatment to achieve necrosis and the associated dose appears in the Theoretical Section as does the theory of achieving selectivity by the modes mentioned. (Implicit is that the process for diagnosis is the same as that for treatment with regards to excitation. Detection is with gamma ray scanning equipment which can be obtained by modification of existing radionuclide scanning equipment by one skilled in the art.)

EXPERIMENTAL

A. Synthesis of 12/29/w

The MIRAGE drug, 12/29/w, was synthesized by forming a coordinate bond of Fe with Bleomycin (see FIG. 10 for the structure).

12/12/w was prepared as follows:

Iron 57 metal was obtained from New England Nuclear DuPont and dissolved in concentrated HCl. The acidic solution of iron was neutralized with sodium hydroxide. 12/29/w was prepared by mixing a 1:2 molar ratio of a neutral aqueous solution of Blenoxane and the neutralized solution of $^{57}$Fe. A stable yellow solution was obtained as the product.

B. Cell Culture Testing Of MIRAGE Treatment Using MIRAGE Drug 12/29/w

The human colon and breast cancer cell lines, HT29 and MCF7, respectively, were obtained from Cambridge Research Lab Inc., and were negative for mycoplasma or bacterial contamination where these tests were performed by Kundsin Lab Inc. A bacterial and mycoplasma-free McCoy cell line was obtained from Kundsin Lab Inc., which the Kundsin Lab tested for these organisms. The human breast and lung cancer cell lines, HTB26 and A549, respectively, were obtained from the American Type Culture Collection. The cells were grown in growth media, Dubecco's modified Eagles medium with 10% fetal bovine serum, 50 ug/ml streptomycin; 1OOug/ml vancomycin, and 2 nM glutamine. The cells were grown in T25 flasks until a monolayer was obtained. The monolayer of each flask was washed twice with iron-free growth media and the cells were incubated with iron-free media to which the drug 12/29/w was added. The control experiments were no drug and drug for the same exposure time and concentration. For the MIRAGE treatment experiment, the cell monolayer was incubated in iron free growth media containing 12/29/w and was irradiated with the 14.4 Kev gamma ray emitted from a New England Nuclear DuPont $^{57}$Co Mossbauer source with a rhodium matrix where the source was driven at a velocity of +1.5 mm/sec by an Austin Science K4 linear motor controlled by an Austin Science S-700 drive module where the constant velocity mode was 85% of the duty cycle. After the time of the experiment had lapsed, the drug was removed by washing the monolayer twice with iron free growth media and once with phosphate buffered saline. The cells were trypsinized with 5% trypsin EDTA and a counted number of cells from each experiment was passed into a new T25 flask containing growth media where counting was performed using methylene blue stain and a hemocytometer.

The cells were grown as a monolayer for a period of time after which they were trypsinized and counted a second time using methylene blue stain and a hemocytometer. The percentage increase in cell number between counts was normalized to that of the control.

RESULTS

The effects of 1 m rad levels of Mossbauer radiation absorbed during MIRAGE treatment of the cancer cell lines MCF7, McCoy, HT29, HTB26, and A549 using the MIRAGE drug 12/19/w appear in Tables 1–5, respectively.

TABLE 1

The Effect of MIRAGE Treatment with Drug 12/29/w, on the MCF7 Cell Line
For all experiments the concentration of drug before addition was 2.3 × 10$^{-4}$M Bleomycin and 1.02 mM$^{57}$Fe.
For all experiments the radiation dose rate was 9 mrads/hr total and 1 mrad/hr for the 14.4 KeV gamma ray.

| | | | | | Proliferation Relative to Control | | | |
|---|---|---|---|---|---|---|---|---|
| Experiment Number | Volume of Drug Dispensed (μl) | Volume of Fe Free Media in Flask (ml) | Duration of Experiment (hrs) | Poliferation Time (hrs) | Control | Drug Alone | MIRAGE (velocity = omm/sec) | MIRAGE (velocity = +1.5 mm/sec) |
| 2 | 25 | 2 | 1 | 96 | 100 | 36 | — | 6.25 |
| 3 | 50 | 3 | 1 | 72 | 100 | 45 | — | 0 |
| 4 | 50 | 3 | .5 | 72 | 100 | 39 | 13 | 2.75 |
| 20 | 50 | 3 | 1 | 120 | 100 | 50 | — | 5.6 |

TABLE 2

The Effect of MIRAGE Treatment with Drug 12/29/w, on the McCoy Cell Line
For all experiments the concentration of drug before addition was $2.3 \times 10^{-4}$ M Bleomycin and 1.022 mM$^{57}$ Fe.
For all experiments the radiation dose rate was 9 mrad/hr total and 1 mrad/hr for the 14.4 KeV gamma ray.
All experiments has a duration of hour; all flasks contained 3 ml of Fe free media, and 50 μl of drug where indicated.

| Experiment Number | Proliferation Time (hrs) | Proliferation Relative to Control | | |
|---|---|---|---|---|
| | | Control | Drug Alone | MIRAGE (velocity = +1.5 mm/sec) |
| 6 | 96 | 100 | 88 | 23.5 |
| 8 | 144 | 100 | 80 | 28.8 |
| 9 | 120 | 100 | 80 | 40 |
| 14 | 120 | 100 | 82 | 39 |
| 7 | 168 | 100 | 25 | 12 |
| 11 | 48 | 100 | 34 | 5 |
| 12 | 120 | 100 | 37 | 26 |
| 13 | 120 | 100 | 34 | 4 |

TABLE 3

Effect of MIRAGE Treatment with Drug, 12/29/w, on the HT29 Cell Line
For all experiments the concentration of drug before addition was $2.3 \times 10^{-4}$ M Bleomycin and 1.02 mM$^{57}$Fe.
For all experiments the radiation dose rate was 9 mrad/hr total and 1 mrad/hr for the 14.4 KeV gamma ray.
All flasks contained 3 ml of Fe free media and 50 μl of drug where indicated.

| Experiment Number | Duration of Experiment (hrs) | Proliferation Time (hrs) | Proliferation Relative to Control | | |
|---|---|---|---|---|---|
| | | | Control | Drug Alone | MIRAGE (velocity = +1.5 mm/sec) |
| 15 | 1 | 72 | 100 | 41 | 28 |
| 16 | 1 | 72 | 100 | 47 | 28 |
| 18 | 3 | 144 | 100 | 56 | 24.6 |
| 21 | 1 | 96 | 100 | 51 | 29 |
| 22 | 1 | 96 | 100 | 53 | 37.7 |
| 23 | 3 | 72 | 100 | 55 | 25 |
| 24 | 3 | 72 | 100 | 63.6 | 13.6 |

TABLE 4

The effect of MIRAGE Treatment with Drug 12/29/2 on the HTB 26 Cell Line.
For all experiments, the concentration of drug before addition was $2.3 \times 10^{-4}$ M Bleomycin and 1.02 mM$^{57}$ Fe.
For all experiments the radiation dose rate was 8.3 mrad/hr total and .93 mrad/hr for the 14.4 KeV gamma ray.
All experiments had a duration of one hour, 5 min. except experiment 27 which had a duration of five hours; all flasks contained 3 ml of Fe free media and 50 μl of drug where indicated.

| Experiment Number | Proliferation Time (hrs) | Proliferation Relative to Control | | |
|---|---|---|---|---|
| | | Control | Drug Alone | MIRAGE (velocity = +1.5 mm/sec) |
| 25 | 192 | 100 | 78.9 | 31.5 |
| 26 | 192 | 100 | 71.4 | 23.8 |
| 27 | 168 | 100 | 82 | 0 |
| 28 | 168 | 100 | 67 | 17 |
| 30 | 144 | 100 | 88 | 25 |
| 31 | 120 | 100 | 92 | 33 |
| 32 | 120 | 100 | 100 | 20 |
| | | | x = 82.76 | x = 21.47 |
| | | | $\sigma_n$ = 10.7 | $\sigma_n$ = 10.2 |

TABLE 5

The Effect of MIRAGE Treatment with Drug, 12/29/w, on the A549 Cell Line
For all experiments the concentration of drug before addition was $2.3 \times 10^{-4}$ M Bleomycin and 1.02 mM$^{57}$Fe.
For all experiments the radiation dose rate was 8.3 mrad/hr total and .93 mrad/hr for the 14.44 KeV gamma ray.
All experiments had a duration of one hour, 5 mins; all flasks contained 3 ml of Fe free media and 50 μl of drug where indicated.

| Experiment Number | Proliferation Time (hrs) | Proliferation Relative to Control | | |
|---|---|---|---|---|
| | | Control | Drug Alone | MIRAGE (velocity =) +1.5 mm/sec |
| 33 | 192 | 100 | 87.5 | 12.5 |
| 34 | 192 | 100 | 80 | 20 |
| 35 | 168 | 100 | 77 | 7.7 |
| 36 | 168 | 100 | 100 | 20 |
| 37 | 144 | 100 | 69.4 | 19.4 |
| 38 | 144 | 100 | 83.3 | 20.8 |
| 39 | 120 | 100 | 97 | 8.8 |
| 40 | 120 | 100 | 70.1 | 17.5 |
| | | | x =83.04 | x =15.8 |
| | | | $\sigma_n$ =10.6 | $\sigma_n$ =5.0 |

DISCUSSION

A statistically significant effect was observed with mrad levels of radiation. Previous studies indicate that at least 500 rads of conventional X-rays or gamma rays is necessary to register a similar effect. 500 rads is $5 \times 10^5$ times the level of radiation used in these MIRAGE treatment experiments. Furthermore, 1mrad of radiation is far below levels which are toxic and can be compared to 200 mrad which is the yearly background dose. Furthermore, the MIRAGE pharmaceutical need not be toxic via chemical or biological reactivity, and pharmaceutical and radiation nontoxicity has implications of nontoxic human therapy for the elimination of a pathological cell population. Previous experiments demonstrated that the most potent killing effect in cells by radiation is from secondary particles produced by internal conversion of gamma ray energy followed by an Auger cascade which results in the radiolysis of the cell's genetic material. The present experiments indicate that it is possible to effect this eradication mechanism with nontoxic levels of radiation which are six orders of magnitude less than that of conventional radiation therapy where the Mossbauer effect was exploited for treatment. The ability to control the occurrence of the Mossbauer effect by the manipulation of the resonance conditions is the basis for selective cell eradication therapy in animals including humans.

STRUCTURE SECTION

One group of MIRAGE drugs is formed by derivatizing the DNA binding molecules of Table 6 with Mossbauer absorber isotopes of Table 7 where derivatizing constitutes the formation of a bond between one or more Mossbauer atoms or a functionality to which one or more Mossbauer atoms is bound and a DNA binding functionality. The MIRAGE compounds retain the DNA binding property of the DNA binding molecule, and contain at least one Mossbauer atom bound in a fashion to permit the Mossbauer phenomenon to occur.

For example, the phenyl group of ethidium bromide (see Table 6 for the structure) is substituted with many organic groups of alkyl, methyl, and phenyl without loss of the capacity to intercalate because the substituents can be positioned in the groove of the DNA molecule upon binding. A representative MIRAGE pharmaceutical is ethidium bromide derivatived with a Mossbauer isotope where the bond between the Mossbauer atom and the rest of the molecule is of high enough energy to permit the Mossbauer phenomenon to occur.

DNA binding molecules such as those in Table 6 are derivatized with Mossbauer absorber isotopes such as those in Table 7 yielding MIRAGE pharmaceuticals. Some representative structures are given with references to their synthetic pathway as follows.

1) A covalent bond directly between a Mossbauer atom and a DNA binding molecule as prepared by the synthetic pathway for compound 16 of the Exemplary Material.

2) A chelating functionality covalently attached to a DNA binding molecule and a chelation bond between the chelating functionality and a Mossbauer atom as prepared by the synthetic pathway for compound 153 of the Exemplary Material.

3) A covalent or organometallic bond between a DNA binding molecule and a Mossbauer organometallic molecule where bonding is with the organic part of the organometallic molecule in the case of a covalent bond and with the Mossbauer metal atom in the case of an organometallic bond as prepared by the synthetic pathways for compounds 100 and 25, respectively, of the Exemplary Material.

4) An organic molecule covalently bound to a Mossbauer nonmetal atom covalently bound to a DNA binding molecule as prepared by the synthetic pathway for compound 38 of the Exemplary Material.

5) A nonmetal Mossbauer atom covalently bound to an organic molecule covalently bound to a DNA binding molecule as prepared by the synthetic pathway for compound 45 of the Exemplary Material.

6) A covalent bond between a DNA binding molecule and an organic molecule to which a Mossbauer atom is attached by chelation with a chelate covalently attached to the organic molecule as prepared by the synthetic pathway for compound 89 of the Exemplary Material.

7) The DNA binding molecule having a coordinate or organometallic bond directly with the Mossbauer atom as prepared by the synthetic pathways for compounds 90 and 60, respectively of the Exemplary Material.

TABLE 6

DNA Binding Molecules

Phenosafranine

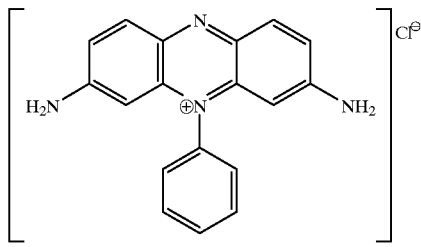

Triostin A

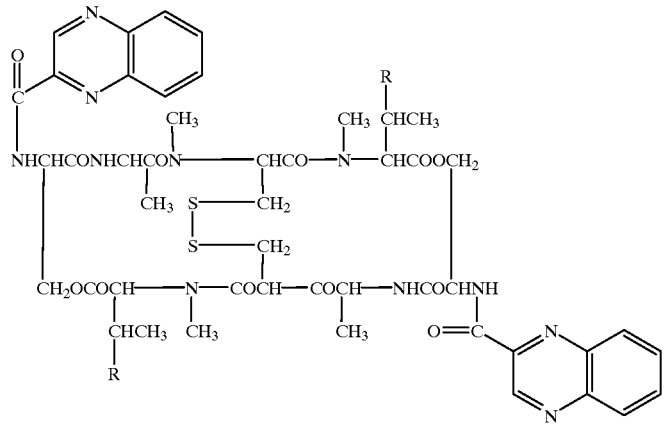

TABLE 6-continued
DNA Binding Molecules
Anthracycline glycosides (Daunorubicin)
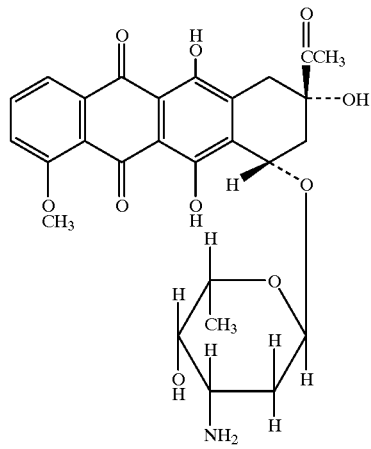
Adriamycin
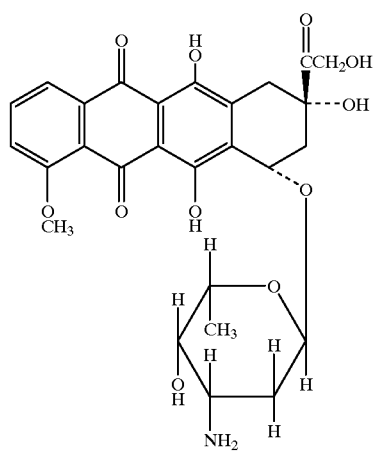
Nogalamycin
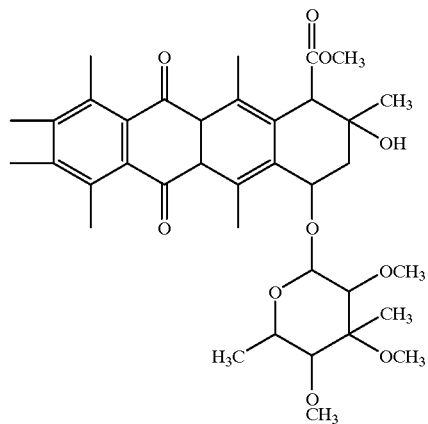

TABLE 6-continued
DNA Binding Molecules
Mithramycin
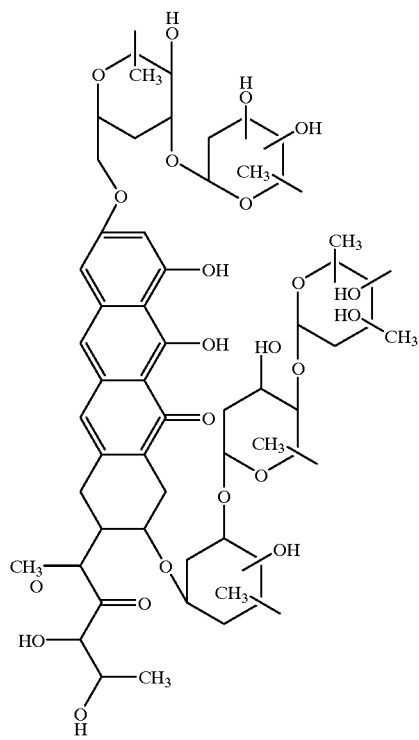
Chromomycin A$_3$
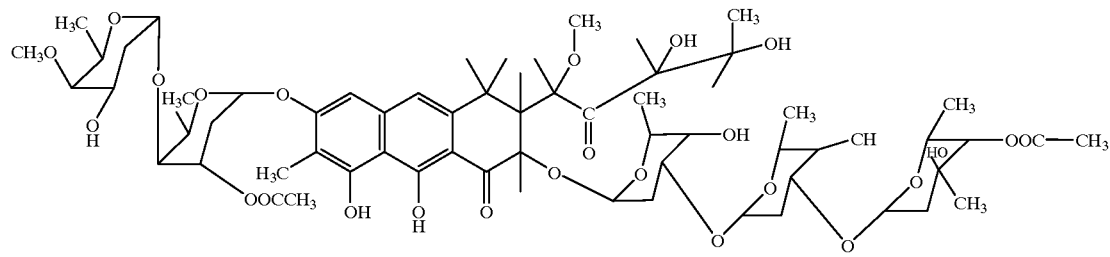
Phenoxazone Antibiotics (Actinomycin D)
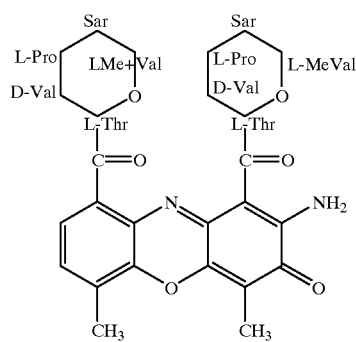

TABLE 6-continued
DNA Binding Molecules
Acridine
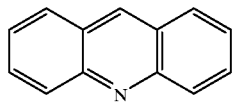
Acridinylmethanesulphonanilide
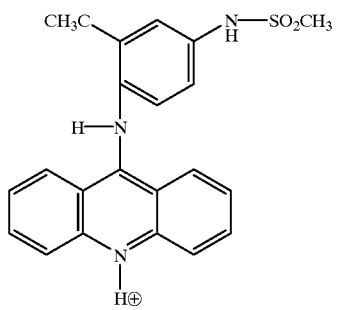
Diacridine
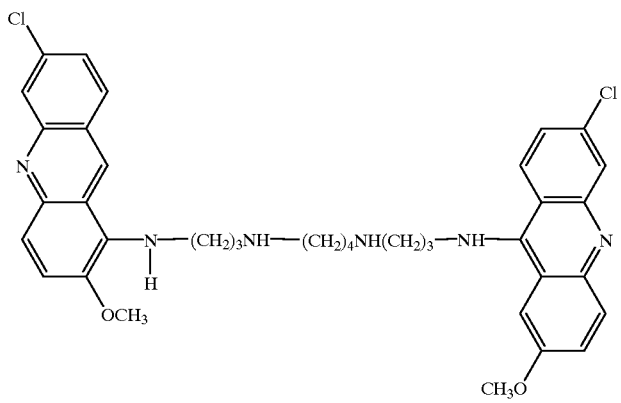
Proflavine
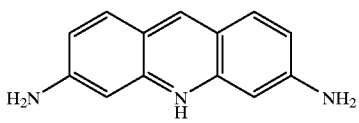
Rhodanine
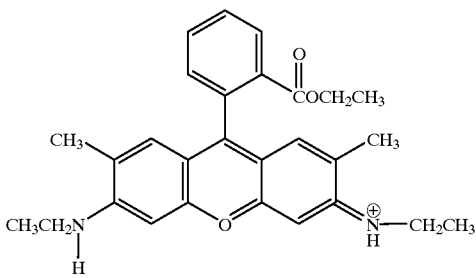

TABLE 6-continued
DNA Binding Molecules
Acriflavine
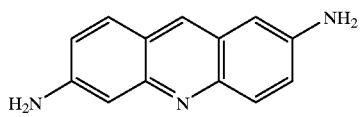
8-Aminoquinoline
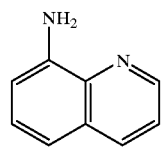
Chloroquine
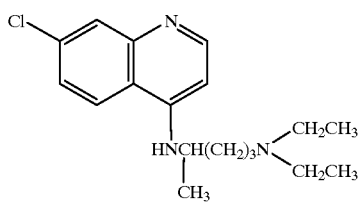
2-Hydroxyethanethiolato(2,2',2"-terpyridine)platinum (II)
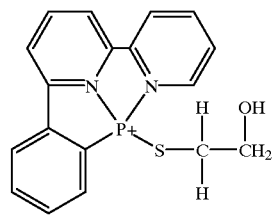
Naphtholthiopheneethanolamine
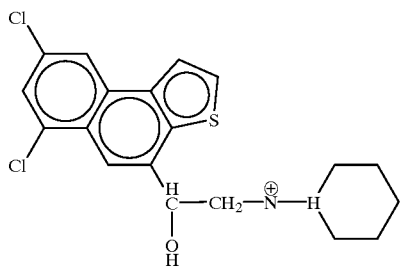
Phenanthridine (Ethidium Bromide)
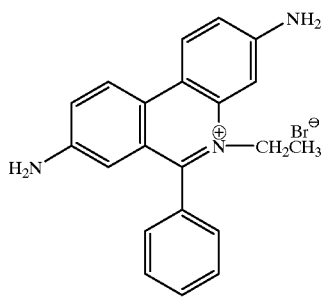

TABLE 6-continued
DNA Binding Molecules
Phenanthroline
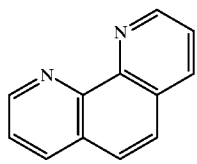
Ellipticene
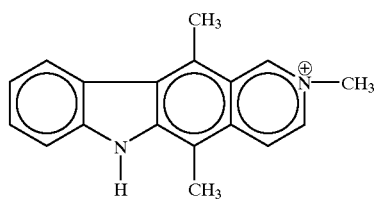
2-Methyl-9-hydroxyellipticine
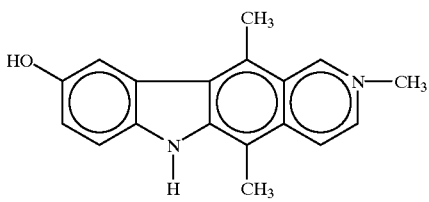
Tilorone
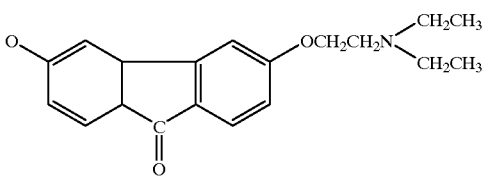
Thioxanthenone (Miracil D)
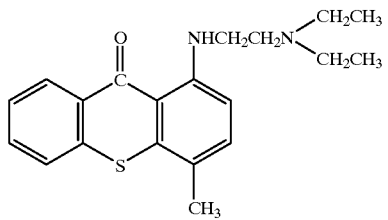
Psoralen
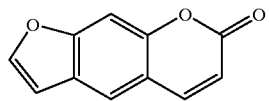

TABLE 6-continued
DNA Binding Molecules
Bleomycin
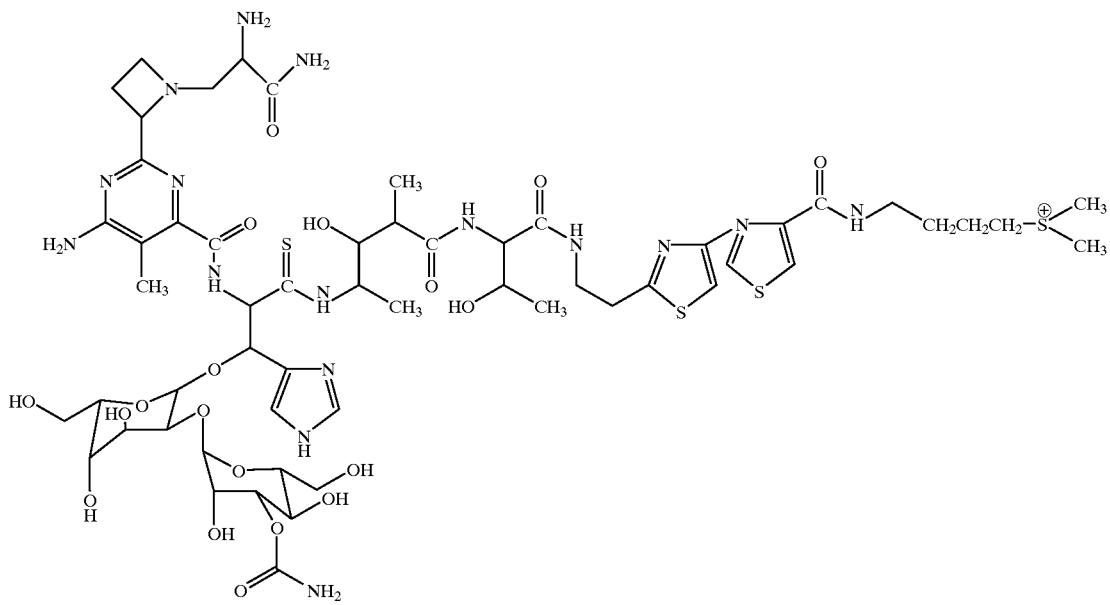
Distamycin A
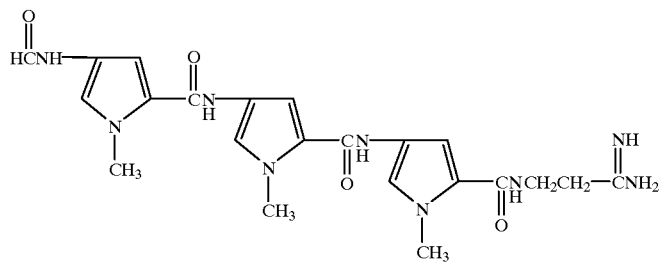
Netropsin
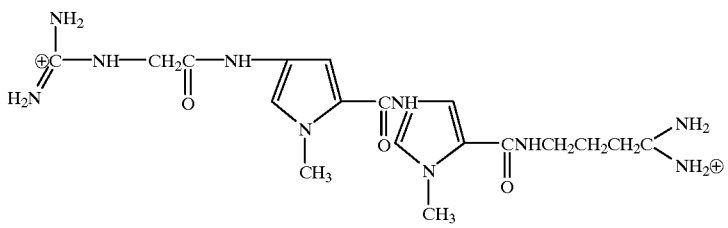
Hydroxystilbamidine
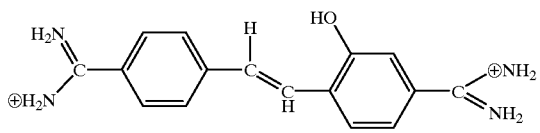

TABLE 6-continued
DNA Binding Molecules
Berenil
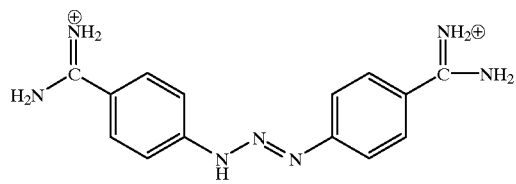
DAPI
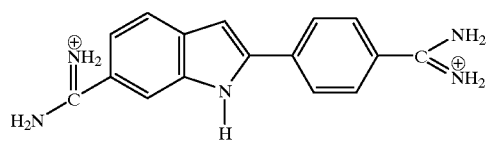
Hoechst 33258
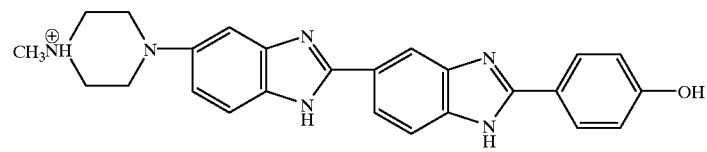
Irehdiamine A
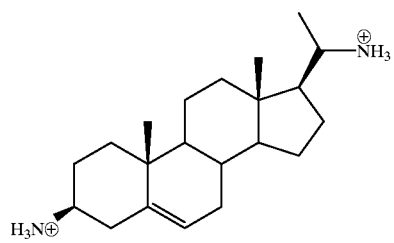
Dipyrandium
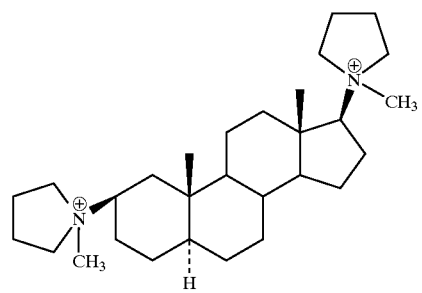

TABLE 6-continued
DNA Binding Molecules
Leteoskyrin
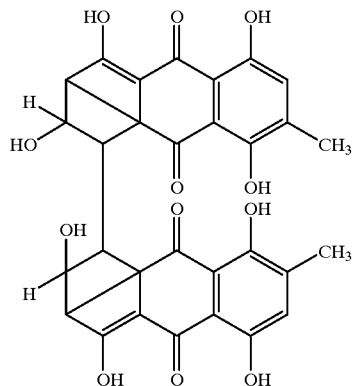
Kanchanomycin
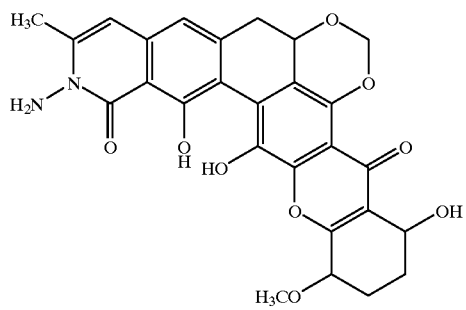
Mitomycin C
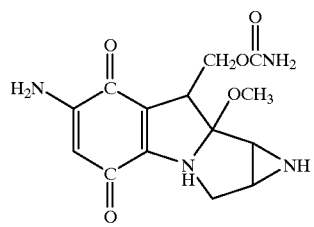
Pyrrolo-(1,4)-benzodiazepine Antibiotics (Anthramycin)
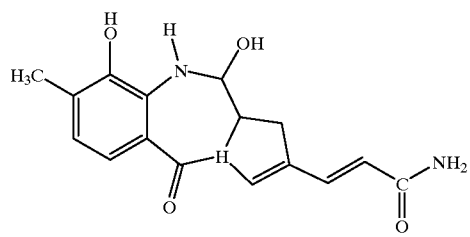

TABLE 6-continued
DNA Binding Molecules
Sibiromycin
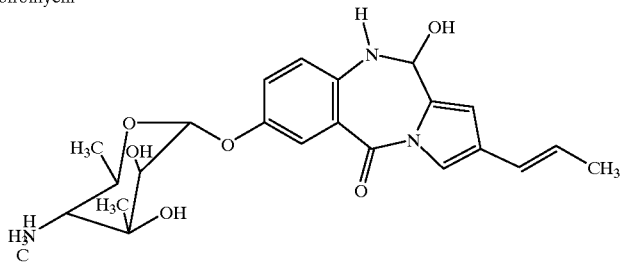
Nitrogen Mustard (Mechlorethamine)
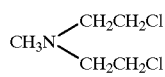
Alkyl Sulfonate (Bulsulfan)
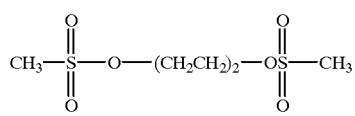
Nitrosourea (Carmustine)
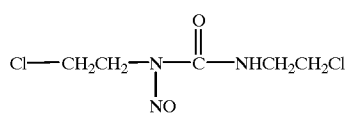
Ethylenimine (Triethylene thiophosphoramide)
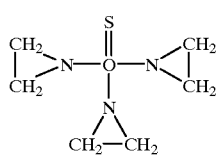
N-2-Acetylaminofluorene
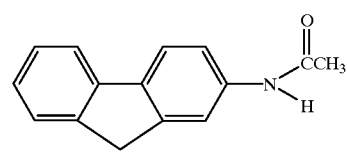
Benzo [a] pyrene
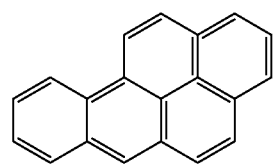
Cis-Diamminedichloroplatinum (II)
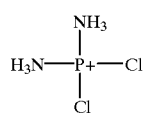

TABLE 6-continued

DNA Binding Molecules

Hedamycin
$C_{41}H_{52}O_{11}N_2$
Rubiflavin
$C_{23}H_{29}NO_5$
Stretonigrin

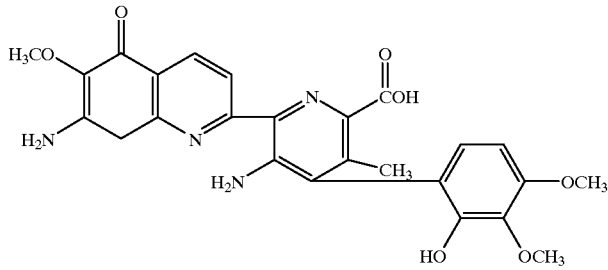

Neocarzinostatin
Ala-Ala-Pro-Thr-Ala-Thr-Val-Thr-Pro-Ser-Ser-Gly-Leu-Asp-Gly-Val-Val-Lys-Val-
Gly-Ala-Gly-Leu-Gln-Ala-Gly-Thr-Ala-Tyr-Asp-Val-Gly-Gln-Cys-Ala-Ser-Val-
Asn-Thr-Gly-Val-Leu-Trp-Asn-Ser-Val-Thr-Ala-Ala-Gly-Ser-Ala-Cys-As
Pro-Ala-An-Phe-Ser-Leu-Thr-Val-Arg-Arg-Ser-Phe-Glu-Gly-Phen-L
Phe-Asp-Gly-Thr-Arg-Trp-Gly-Thr-Val-Asx-Lys-Thr-Thr-Ala-Ala
Cys-Gln-Val-Gly-Leu-Ser-Asp-Ala-Ala-Gly-Asp-Gly-Glu-Pro-Gly
Val-Ala-Ile-Ser-Phe-Asn

EXEMPLARY MATERIAL

The materials which are listed below are representative examples of possible MIRAGE drugs which can be synthesized by the derivatization of known DNA binding materials and known Mossbauer absorber isotopes from Tables 6 and 7, respectively to yield the representative structures given in the Structure Section. The following examples of reaction pathways are intended to be exemplary and other pathways can be devised by one skilled in the art. Furthermore, only a representative number of MIRAGE pharmaceuticals are shown and a vast number of other MIRAGE pharmaceuticals can be made by one skilled in the art following the guide lines herein disclosed.

And, the disclosed MIRAGE pharmaceuticals and representative structures disclosed in the Structure Section can be modified to further MIRAGE pharmaceuticals to improve properties such as permeability to cells, solubility, and enhanced selectivity by addition of functional groups by one skilled in the art. Representative functional groups include alkyl, cycloalkyl, alkoxycarbonyl, cyano, carbamoyl, heterocyclic rings containing C, O, N, S, sulfo, sulfamoyl, alkoxysulfonyl, phosphono, hydroxyl, halogen, alkoxy, alkylthiol, acyloxy, aryl, alkenyl, aliphatic, acyl, carboxyl, amino, cyanoalkoxy, diazonium, carboxyalkylcarboxamido, alkenyl thio, cyanoalkoxycarbonyl, carbamoylalkoxycarbonyl, alkoxy carbonylamino, cyanoalkylamino, alkoxy carbonylalkylamino, sulfoalkylamino, alkylcarbonyloxy, cyanoalkyl, carbonyloxy, carboxyalkylthio, arylamino, heteroarylamino, alkoxycarbonyl, alkylcarbonyloxy, carboxyalkoxy, cyanoalkoxy, alkoxycarbonylalkoxy, carbamoylalkoxy, carbamoylalkyl carbonyloxy, sulfoalkoxy, nitro, alkoxyaryl, halogenaryl, aminoaryl, alkylaminoaryl, tolyl, alkenylaryl, allylaryl, alkenyloxyaryl, allyloxyaryl, allyloxyaryl, cyanoaryl, carbamoylaryl, carboxyaryl, alkoxycarbonylaryl, alkylcarbonyoxyaryl, sulfoaryl, alkoxysulfoaryl, sulfamoylaryl, and nitroaryl.

GENERAL SYNTHETIC PATHWAYS

The following synthetic reactions are exemplary of general synthetic reactions to be used to link a Mossbauer absorber atom such as one from Table 7 with a DNA binding molecule such as one from Table 6.

General reactions involving general organic chemistry such as Wittig reactions, nucleophilic substitution reactions, tosylate reactions, Friedel-Crafts alkylations and acylations, etc. appear in the Exemplary Material and are generally known to one skilled in the art. These same types of reactions can be used by one skilled in the art to derivatize the DNA binding molecules of Table 6 to produce the starting materials generally shown in the Exemplary Material. In some cases which are exemplified in the Exemplary Material Grignard reagents are prepared of the DNA binding molecules or derivatizing organic or organometallic molecules containing a Mossbauer atom. The Grignard reagents can be prepared by halogenation using a halogen gas and an initiator or by using a halogen gas and a catalyst such as $FeX_3$ where X is halogen followed by reaction with magnesium.

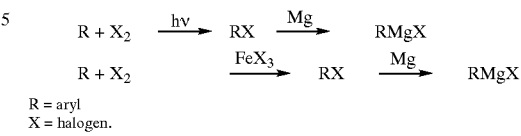

R = aryl
X = halogen.

For Grignard reagents as well as other compounds formed by the above synthetic pathways, multiple side products of the materials shown in the Exemplary Material are possible and are often desirable. However, the reactions shown are intended to be exemplary of the types of reactions possible and are in no way intended to be exhaustive.

General Reactions of Tin

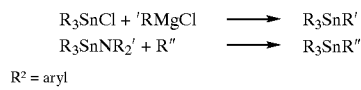

$R^2$ = aryl (Comprehensive Organometallic Chemistry, Sir Geoffrey Wilkinson, Editor, (1982), Vol. 12, Chapter 11) incorporated by reference.

General Reactions of Antimony

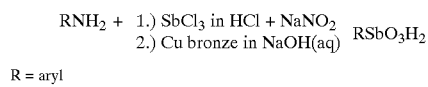

R = aryl

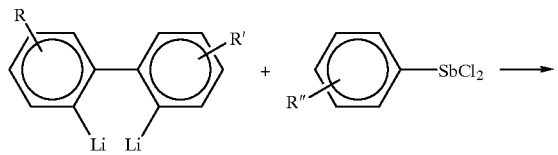

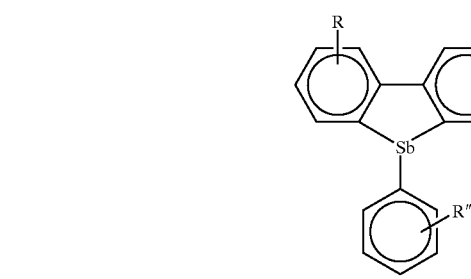

R″ = 1° alkyl (Organometallic Compounds Methods of Synthesis Physical Constants and Chemical Reactions, Michael Dubb, Editor, 2nd Edition, Vol. III, (1968), pp. 653–925) incorporated by reference.

General Reactions of Tellurium

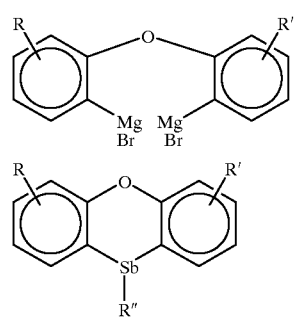

R = alkyl, vinyl, aryl (Seebach, P.; Beck, A.L., Chem. Ber., 108, (1975), 314–321) incorporated by reference.

General Reactions of Germanium

(Comprehensive Organometallic Chemistry, Sir Geoffrey Wilkinson, Editor, (1982), Vol. 2, Chapter 10) incorporated by reference.

General Reactions of Mercury

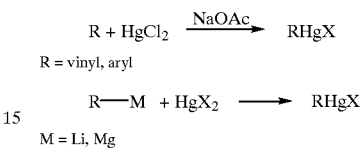

R = vinyl, aryl

M = Li, Mg (Comprehensive Organometallic Chemistry, Sir Geoffrey Wilkinson, Editor, (1982), Vol. 2, Chapter 17) incorporated by reference.

General Reactions of Iodine

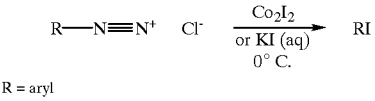

R = aryl (Organic Chemistry, Fessenden, R. J., Fessenden, J. S., (1979) p. 728) incorporated by reference.

Representative examples of reactions which yield DNA binding MIRAGE pharmaceuticals are given in the following examples. These examples are not to be taken as an exhaustive listing, but only illustrative of the possibilities according to the present invention.

EXAMPLE 1

Compound 5 is prepared as follows:

Trimethylstannylchloride 1, is reacted with imine 2, to form aminotin compound 3. The aminotin 3, is reacted with psoralen 4 to form the tin derivatized psoralen product 5 where the reaction between 3 and 4 is as described in *Comprehensive Organometallic Chemistry*, Sir Geoffrey Wilkinson, Editor, (1982), Vol. 2, p. 601, incorporated by reference. Substitution at other aryl sites is likely, and these products are also expected to have utility.

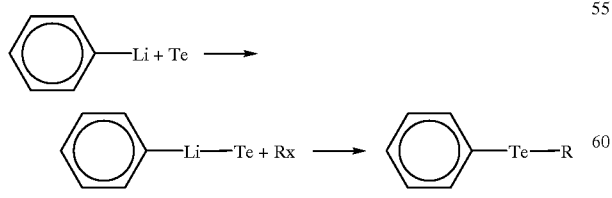

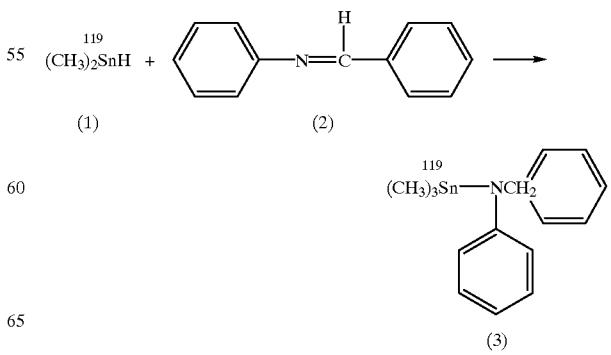

EXAMPLE 3

Compound 11 is prepared as follows:

Actinomycin D, 9, is reacted with tetraalkyltin compound 10 to form the tin derivatized Actinomycin D product 11.

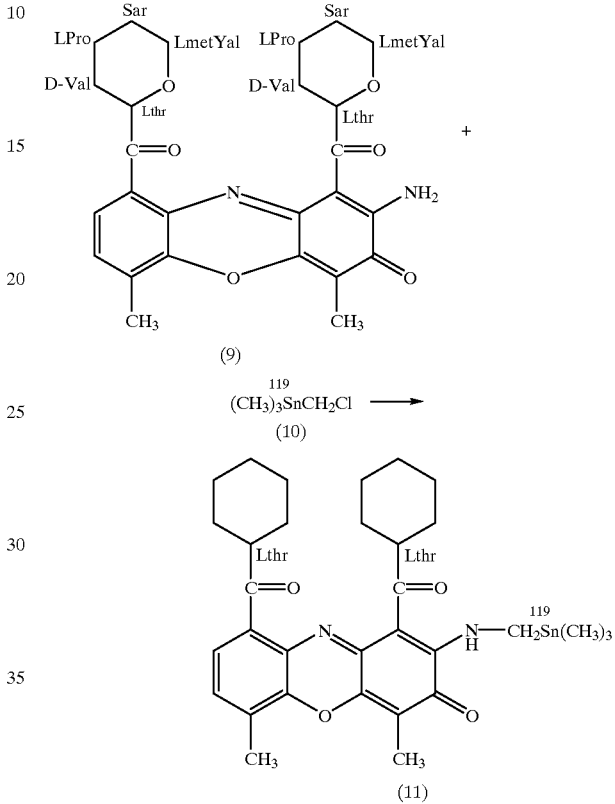

EXAMPLE 2

Compound 8 is prepared as follows:

The Grignard reagent 6, which is an 8-aminoquinoline derivative, is reacted with trimethylstannylchloride 7, to give the tin derivatized quinoline product 8 where the reaction between 6 and 7 is described in *Comprehensive Organometallic Chemistry*, Sir Geoffrey Wilkinson, Editor, (1982), Vol. 2, pp. 530–532 incorporated by reference.

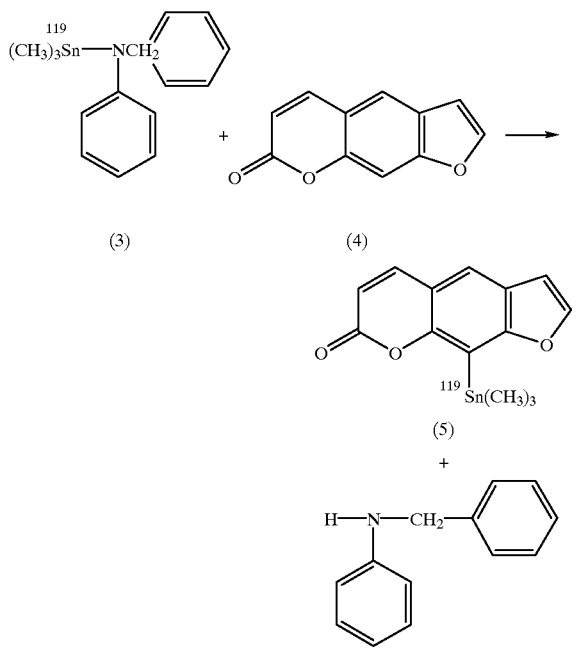

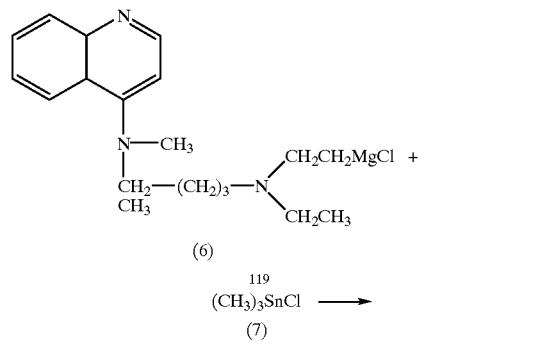

EXAMPLE 4

Compound 13 is prepared as follows:

Trimethystannylchloride is reacted with a Grignard reagent derivative of Irehdiamine A to give product 13.

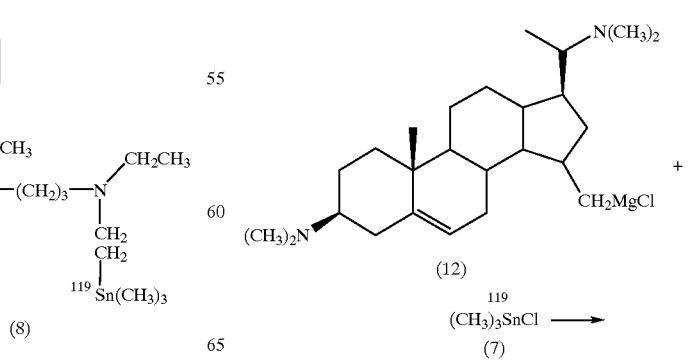

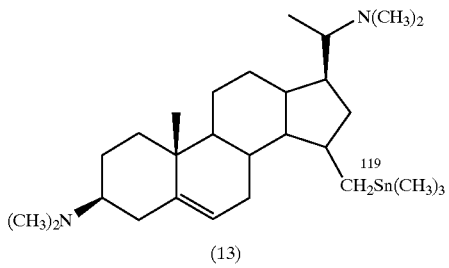

(13)

EXAMPLE 5

Compound 16 is prepared as follows:

A Grignard reagent of phenosafranin is reacted with trimethylstannylchloride 7 to give product 16.

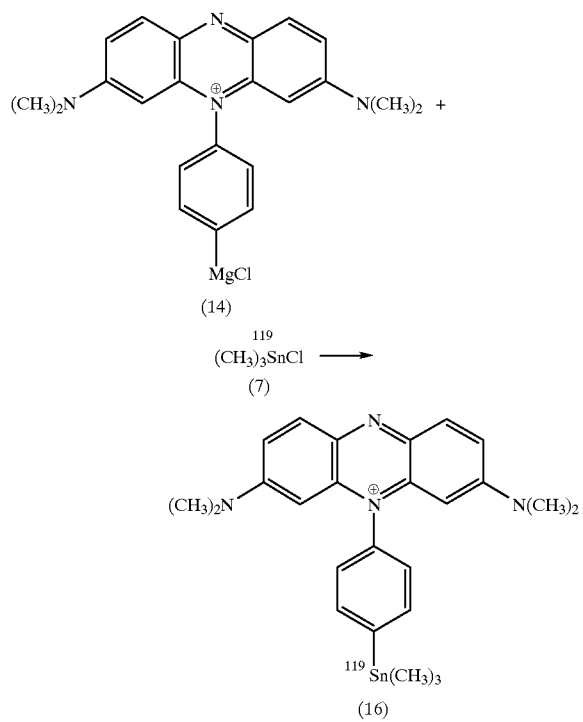

EXAMPLE 6

Compound 19 is prepared as follows:

Proflavine 17, is reacted with antimony trichloride in the presence of HCl and NaNo$_2$. The product is hydrolyzed and the diazonium salt decomposed by reaction with NaOH and copper bronze to yield the antimony derivatized acridine 19 according to the method of O'Donnell, G. J., Iowa State Coll. J. Sci., 20, 34-6 (1945); CA 40. 4689; Ph.D. Thesis No. 760, submitted Aug. 23, 1944 at Iowa State College, incorporated by reference.

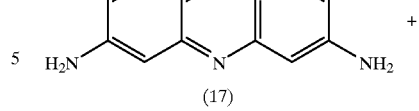

(17)

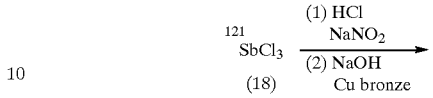

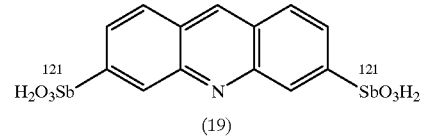

(19)

EXAMPLE 7

Compound 23 is prepared as follows:

1,2-dihydroxybenzene is reacted with antimony trichloride in the presence of HCl to give 2-chloro-1,3,2,-benzodioxastibole 21. Nucleophilic condensation of hydroxy derivatized ethidium bromide 22, with compound 21 yields the antimony derivatized ethidium bromide product 23. Substitution products at the amino groups are also anticipated, and utility of these products is expected.

The synthetic pathway of product 23 is in general described in *The Heterocyclic Derivatives of Phosphorus, Arsenic, Antimony, and Bismuth,* Frederick G. Mann, 2nd Ed., (1970) pp. 615–619, incorporated by reference.

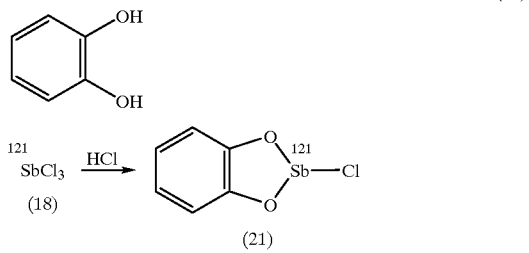

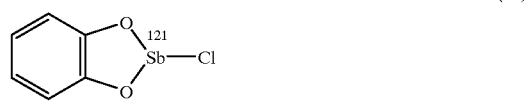

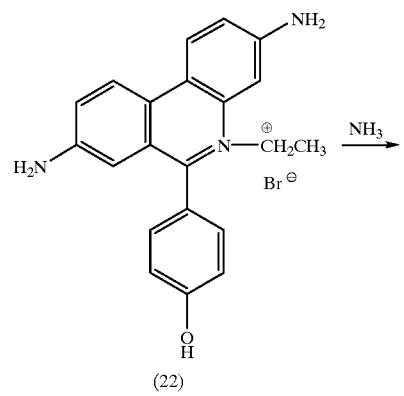

(22)

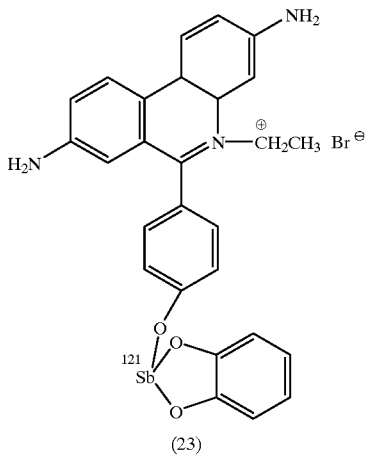

(23)

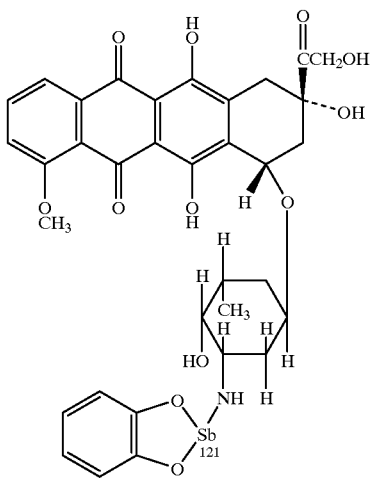

(25)

EXAMPLE 8

Compound 25 is prepared as follows:

2-chloro-1,3,2-benzodioxastibole 21, is reacted with the anthracycline, doxorubicin 24, to give the antimony derivatized doxorubicin product 25. Substitution products of the sugar hydroxyl groups are anticipated, and utility of these side products is expected.

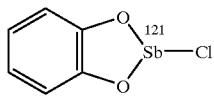

(21)

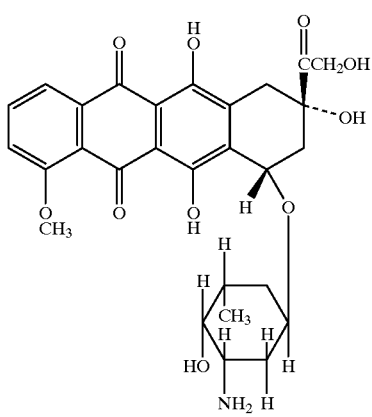

(24)

EXAMPLE 9

Compound 28 is prepared as follows:

Compound 26, 2,2'-biphenyldilithium is condensed with aryldihalostibine 27, in benzene under reflux to yield the product 28.

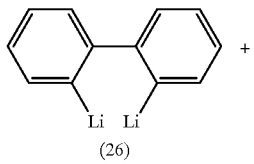

(26)

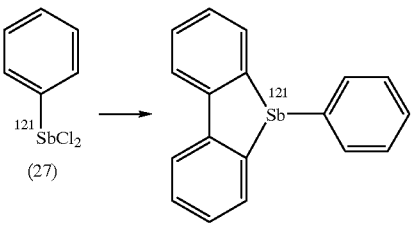

(27) → (28)

EXAMPLE 10

Compound 31 is prepared as follows:

N,N'-dimethyl-4,4'-diamino-2,2'-oxybis (phenylenemagnesium bromide) is condensed with primary dihalostibine 27, in ether, benzene, dioxane, or their mixtures to give product 31.

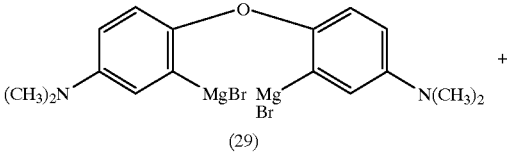

(29)

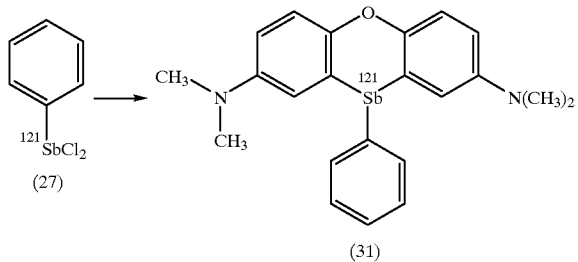

(27) → (31)

EXAMPLE 11

Compound 34 is prepared as follows:

Luteoskyrin 32, is reacted with 2-chloro-1,3,2-benzo-dioxastibole 21, to give the product 34. Substitution products of other hydroxyl groups is expected and utility is expected for many of these products.

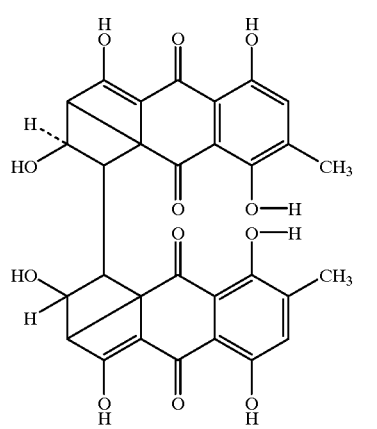

(32)

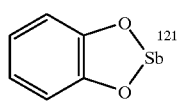

(21)

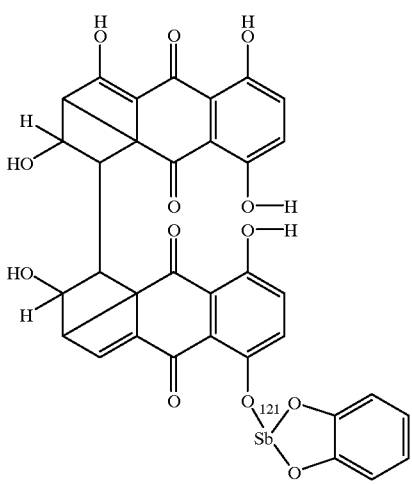

(34)

EXAMPLE 12

Compound 38 is prepared as follows:

Phenyllithium is reacted with tellurium to give adduct 36 which is reacted with the phenanthridine 37 to give the tellurium derivatized product 38 according to the reaction of Seebach, D.; Beck, A. L., Chem. Ber. 108, (1975) pp. 314–321, incorporated by reference.

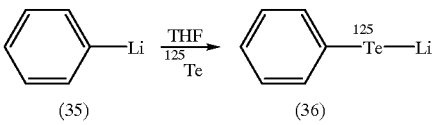

(35) → (36)

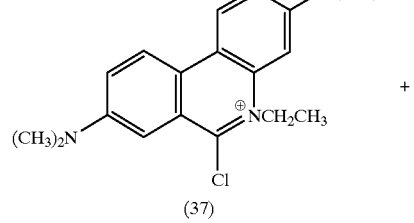

(37) +

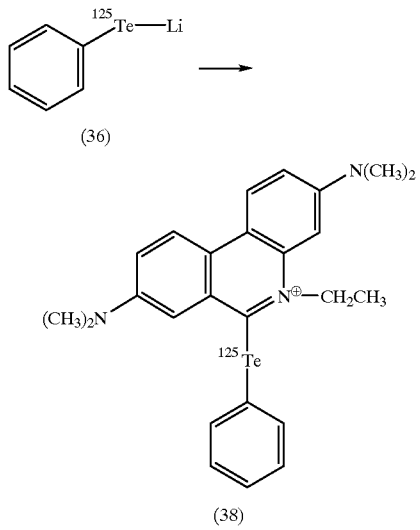

(36) →

(38)

EXAMPLE 13

Compound 40 is prepared as follows:

1,8-dilithium naphthalene 39, is reacted with tellurium to yield the product 40 according to the method of Marfat, A., et al, Journal of the American Chemical Society, 99, (1977) pp. 255–256, incorporated by reference.

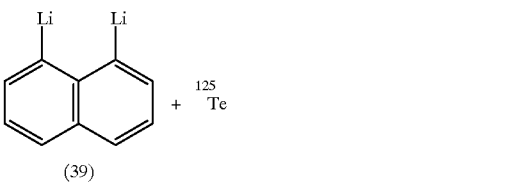

(39)

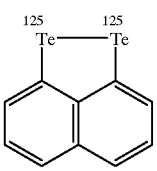

(40)

EXAMPLE 14

Compound 42 is prepared as follows:

3,6-dichloroacridine 41, is reacted with lithium followed by tellurium and methylchloride to give the alkyl tellurium derivatized acridine product 42.

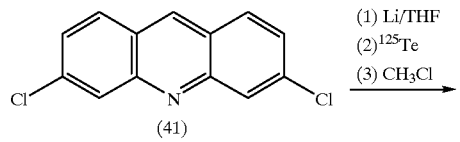

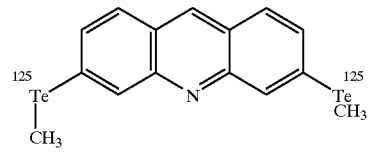

EXAMPLE 15

Compound 45 is prepared as follows:

Kanchanomycin 43 is reacted with the dialkyl telluride 44 to give the product 45. Additional products substituted at the hydroxyl groups are anticipated, and utility of these products is expected.

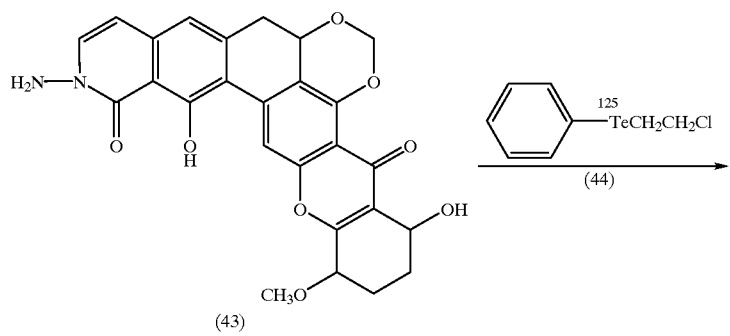

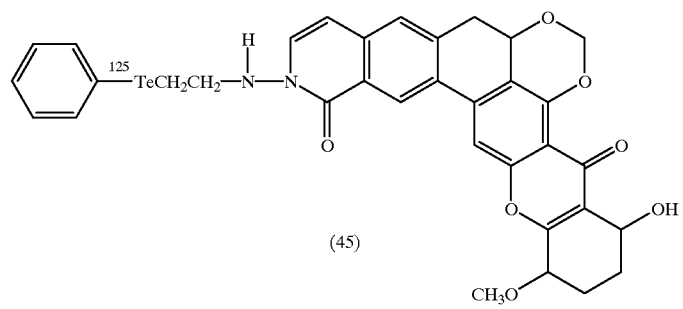

EXAMPLE 16

Compound 47 is prepared as follows:

Diacridine 46 is reacted with lithium followed by tellurium and methylchloride to give the methyltellurium derivatized biacridine product 47.

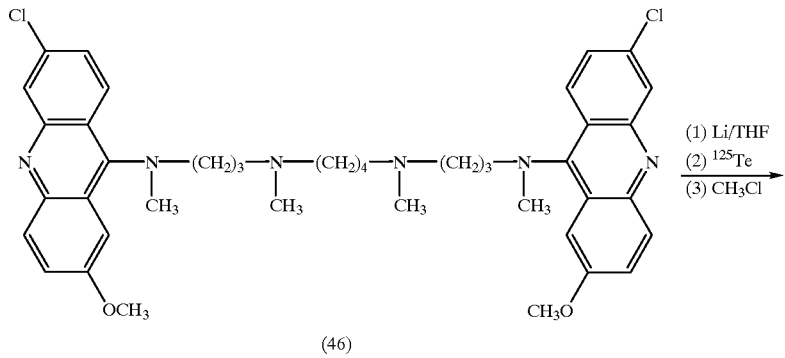

-continued

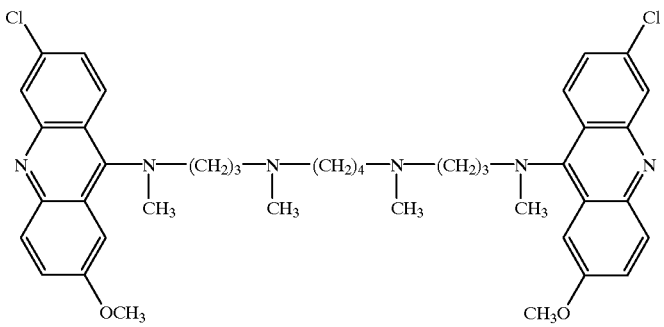

(47)

EXAMPLE 17

Compound 50 is prepared as follows:

Hycanthone 48, is reacted with the tellurium derivatized phosphonium ylid 49 to give the alkyl tellurium derivatized thioxanthenone product 50.

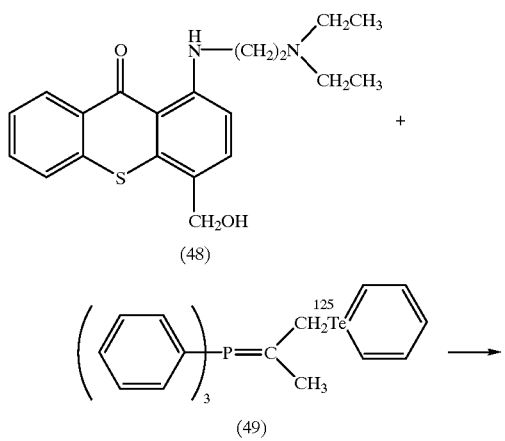

+

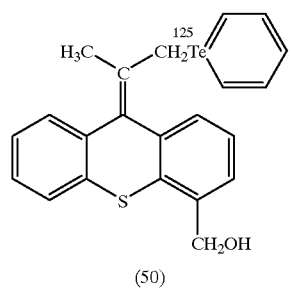

(50)

EXAMPLE 18

Compound 52 is prepared as follows:

Trimethylithium germanide 15, is reacted with 1,2-dichloroethane 30, and 2-chloloethyltrimethylgermanium 33, is isolated from the product mixture which is reacted with Netropsin to give the product 52. Other substitution products are anticipated, and are expected to be of utility.

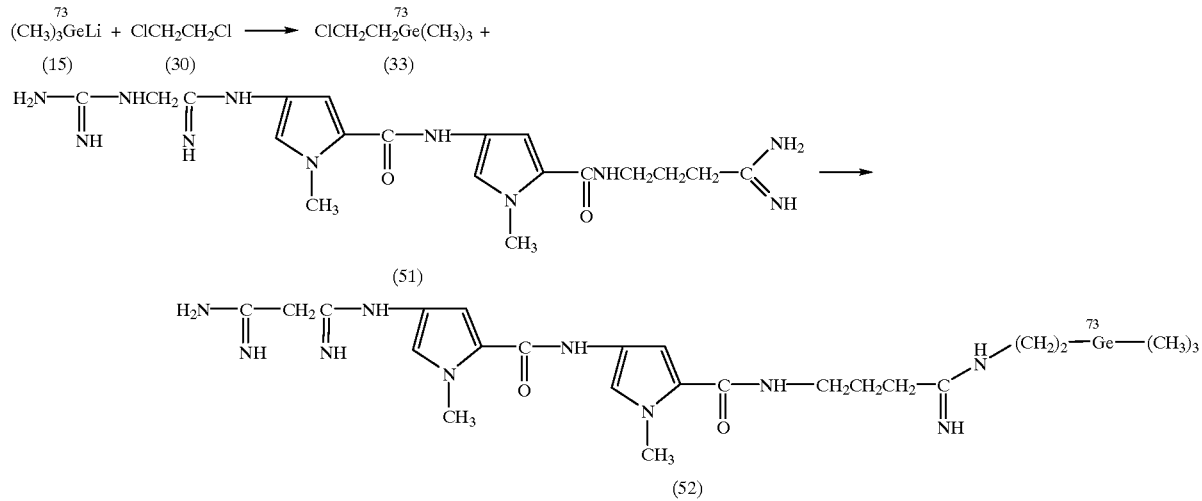

EXAMPLE 19

Compound 55 is prepared as follows:

The halogenated derivatize of ellipticine 53, is reacted with trimethyllithium germanide 15, to give the product 55, according to the method described in *Comprehensive Organs Metallic Chemistry*, Sir Geoffrey Williams, Editor (1982) Vol. 2, Ch. 10, incorporated by reference.

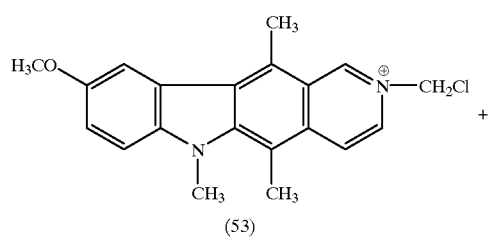

(53)

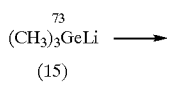

(15)

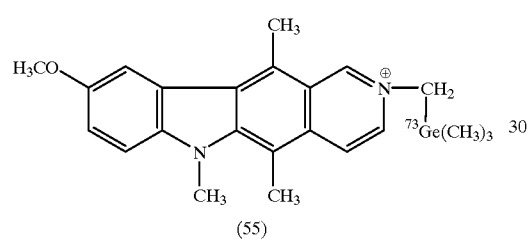

(55)

EXAMPLE 20

Compound 58 is prepared as follows:

Platinum compound 56 is reacted with 9-hydroxyquinoline in acetic acid to give the product 58 according to the reaction described by Kite, K. and Truter, M. R., J. Chem. Soc. (A), 1966, 207, incorporated by reference.

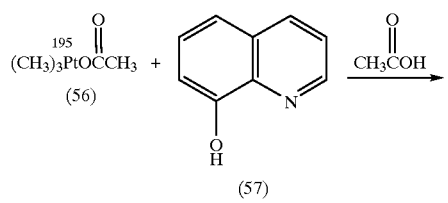

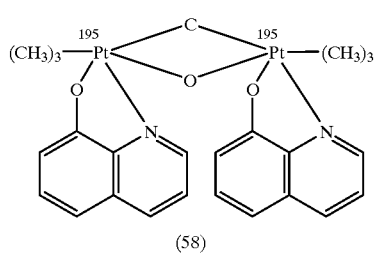

(58)

EXAMPLE 21

Compound 59, cis-diamminedichloro-platinum(II), is a compound which binds directly to DNA.

It is synthesized using $^{195}$Pt as described in Dhara, S. C., Indian J. Chem., 8, (1970) p. 193, incorporated by reference.

EXAMPLE 22

Compound 60, 2-hydroxyethanethiolato(2,2',2"terpyridine)platinum(II) intercalates directly into DNA.

It is synthesized using $^{195}$Pt as described in Jeannette, L. W.; Lippard, S. J.; Vassiliades, G. A. and Bauer, W. R. (1974), Proc. Nat. Acad. Sci. USA, 71, 3839–3843, incorporated by reference.

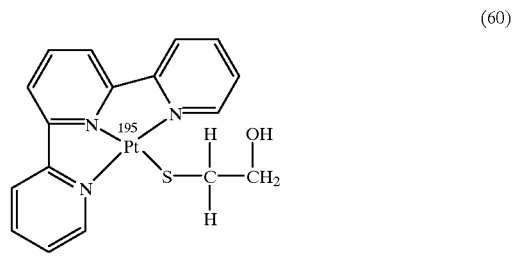

EXAMPLE 23

Compound 64 is prepared as follows:

Gold compound 61 is reacted with trimethylphosphonium-ylid 94, and dimethylchloromethylphosphoniumylid 54, to give product 62 as described by Schmidbaur, H., and Franke, R., Inorganica Chimica Acta, 13 (1975) 79–83 (incorporated by reference) with the exception that dimethylchloromethylphos-phoniummythylid is also made present with trimethylphos-phoniummethylid and the desired product is isolated from the reaction mixture. 62 is reacted with phenanthridine 63, to give the product 64 where products with substitution at the aniline nitrogens are anticipated and these products are expected to have utility.

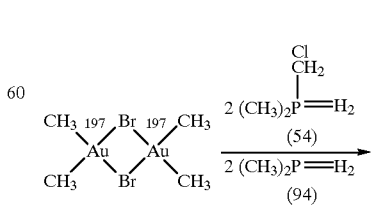

-continued

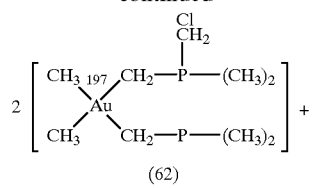
(62)

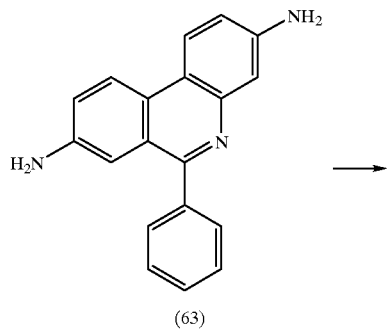
(63)

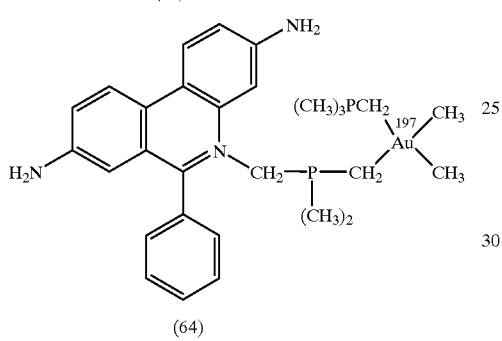
(64)

EXAMPLE 24

Compound 67 is prepared as follows:
Gold ylid compound 65 is reacted with nitrogen mustard 66 to give the product 67.

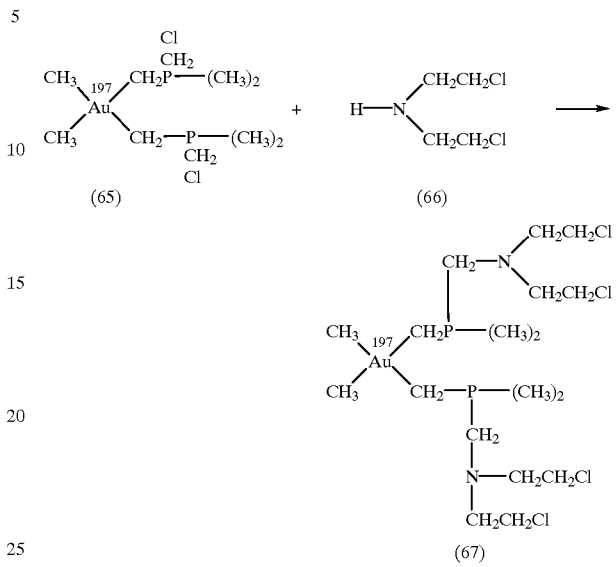
(65)  (66)  (67)

EXAMPLE 25

Compound 72 is prepared as follows:
Pyrrole adduct 68 is mercurated by the reaction described in *Comprehensive Organometallic Chemistry,* Sir Geoffrey Wilkinson, Editor, (1982), Vol. 2, p. 871 (incorporated by reference) to give adduct 69 which is reacted with oxalyl chloride to give acid chloride 70. The acid chloride is reacted with amine 71 to give the mercurated derivative of Distamycin A 72.

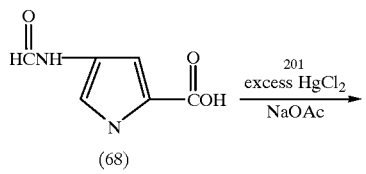
(68)

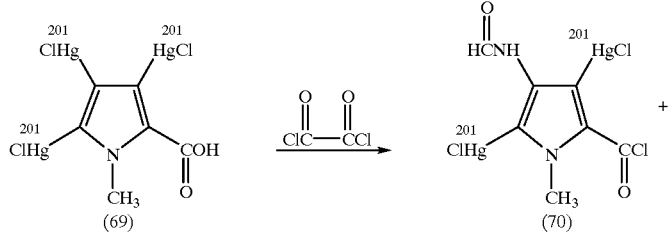
(69)  (70)

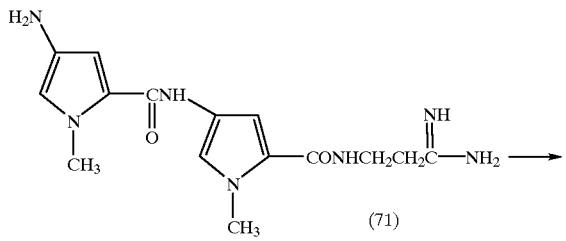
(71)

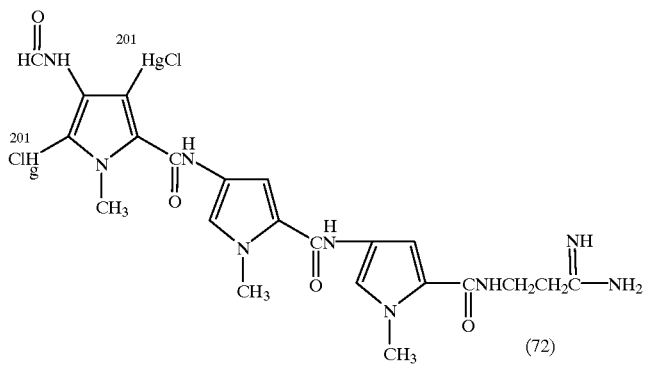

(72)

EXAMPLE 26
Compound 74 is prepared as follows:

Miracil 73 is mercurated to give product 74. Mixtures of mercuration products are anticipated, and these products are expected to be of utility.

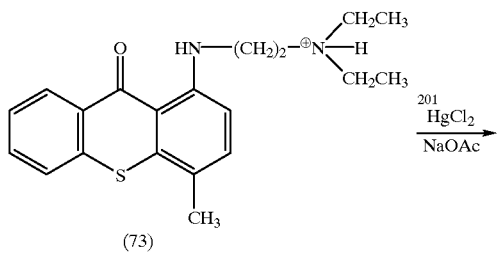

(73)

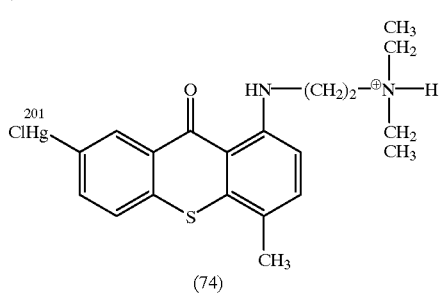

(74)

EXAMPLE 27
Compound 76 is prepared as follows:

N-acetylaminofluorene 75 is mercurated to give product 76. Mixtures of mercuration products are anticipated and these products are expected to be of utility.

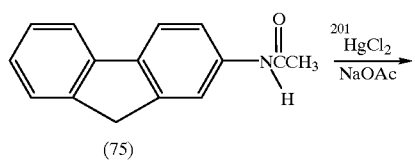

(75)

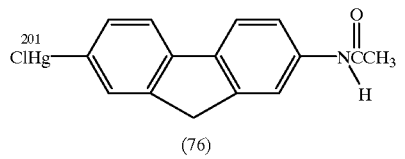

(76)

EXAMPLE 28

Compound 82 is prepared as follows:

Rutheniumtrichloride is reacted with cyclopentadiene to give ruthenocene 77, which is acylated to give ketone 78. Both reactions appear in *Comprehensive Organometallic Chemistry,* Sir Geoffrey Wilkinson, Editor, (1982), Vol. 4, pp. 754–773, incorporated by reference. Adduct 78 is reduced with lithium aluminum hydride to give alcohol 79 which is reacted with p-toluenesulphonylchloride 123 to give tosylate 80. Adduct 80 is reacted with Adriamycin 81, to give product 82. Substitution of other nucleophilic sites of Adriamycin is anticipated, and these products are expected to be of utility.

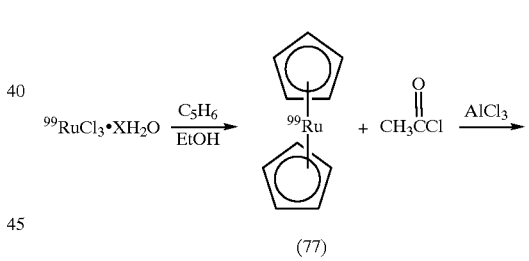

(77)

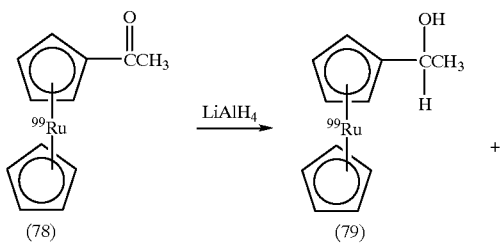

(78) (79)

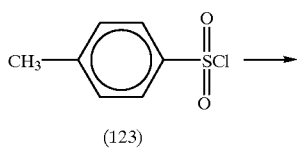

(123)

55
-continued

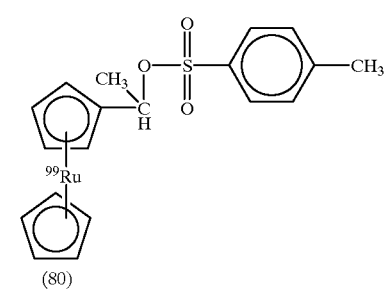

(80)

+

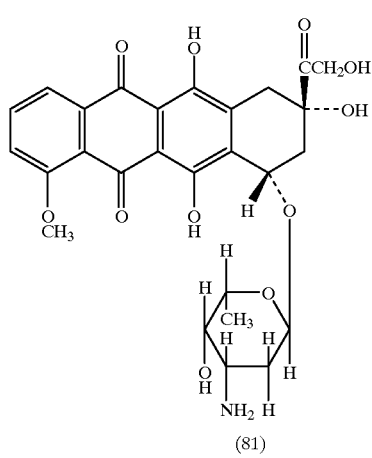

(81)

⟶

56
-continued

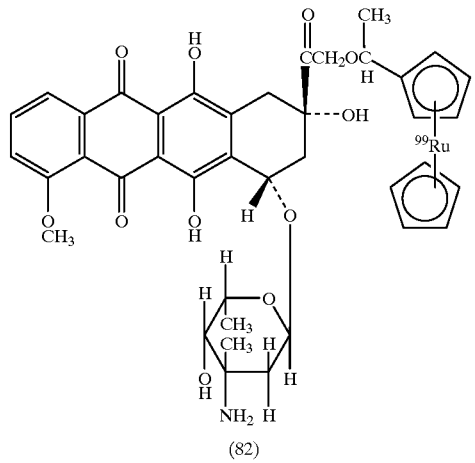

(82)

EXAMPLE 29

Compound 85 is prepared as follows:

Alkyl halogen derivative of ruthenocene 83 which is prepared from 79 by treatment with phosphorous trichloride is reacted with Sibiromycin 84, to give the product 85 which is the preferred substitution product.

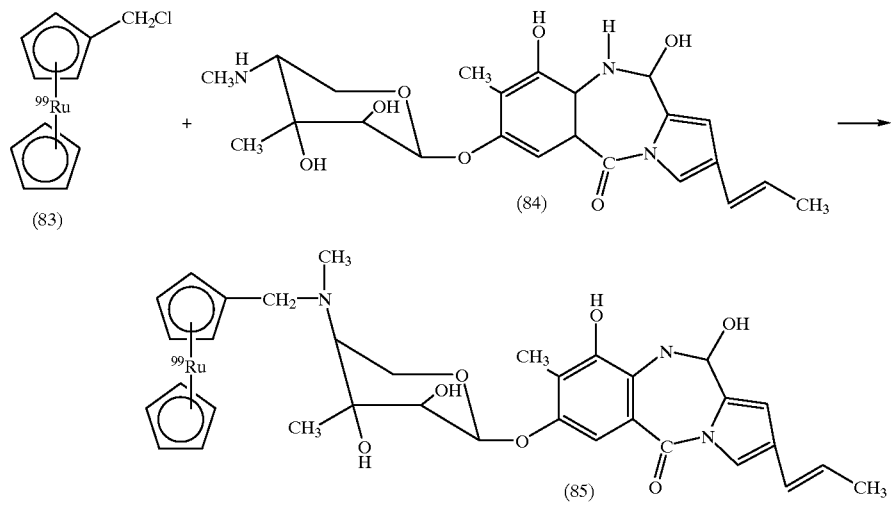

EXAMPLE 30

Compound 86 which is a coordinate compound of ruthenium and phenanthroline intercalates DNA directly.

It is synthesized using 99Ru as described in *Comprehensive Organometallic Chemistry,* Sir Geoffrey Wilkinson, Editor, (1982), Vol. 4, pp. 704–705, incorporated by reference.

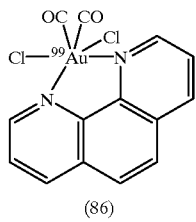

(86)

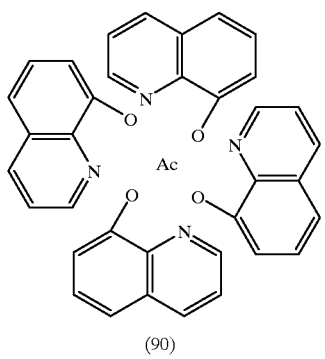

(90)

Ac = $^{214}U^{4+}$, $^{238}U^{4+}$, $^{232}Th^{4+}$

EXAMPLE 31

Compound 89 is prepared as follows:

Quinacrine derivative 87 is reacted with a chloromethyl derivative of diethlenetriaminepentaacetic acid 88, to give the product 89 which is the preferred product of the possible mixture involving substitution of the other nucleophilic sites.

EXAMPLE 33

Compound 93 is prepared as follows:

Alkyl halogen derivatied Bis(arene) tungsten compound 91, which is synthesized as described in *Comprehensive Organometallic Chemistry*, Geoffrey Wilkinson, Editor, (1982), Vol. 3, pp. 1356–1359 (incorporated by reference) with the modifications of using benzene and methyl substituted benzene following the synthetic route described in the above reference. The monomethyl product is isolated from the product mixture and chlorinated to give 91 or chloromethylbenzene is used in the referenced synthesis with isolation of 91 which is reacted with alcohol derivative of 8-aminoquinoline 92, to give the product 93 where other substitution products are anticipated, and utility is expected.

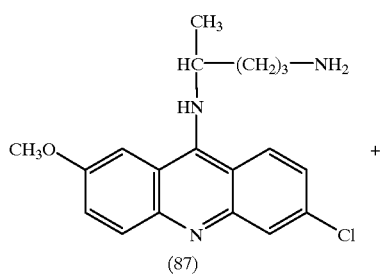

(87)

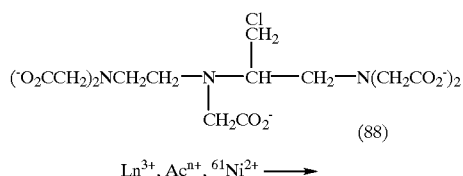

(88)

$Ln^{3+}$, $Ac^{n+}$, $^{61}Ni^{2+}$ ⟶

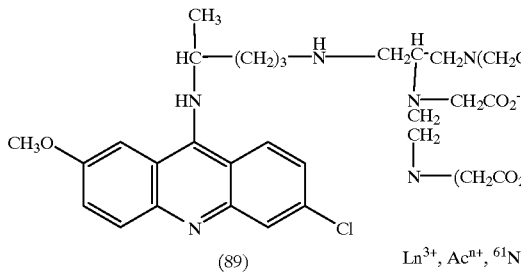

(89)

$Ln^{3+}$, $Ac^{n+}$, $^{61}Ni^{2+}$

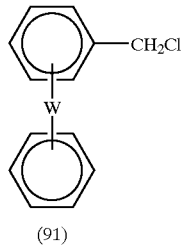

(91)

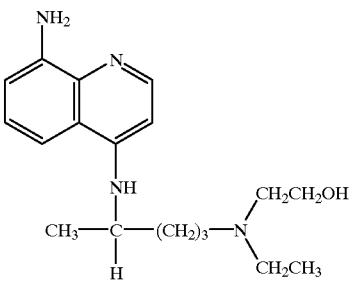

(92)

Ln = $^{145}$Nd, $^{145}$Pr, $^{147}$Pr, $^{149}$Sm, $^{151}$Sm, $^{153}$Sm, $^{154}$Sm, $^{151}$Em, $^{153}$Eu, $^{154}$Gd, $^{155}$Gd, $^{156}$Gd, $^{157}$Gd, $^{158}$Gd, $^{160}$Gd, $^{159}$Tb, $^{160}$Dy, $^{161}$Dy, $^{162}$Dy, $^{164}$Dy, $^{165}$Ho, $^{164}$Er, $^{166}$Er, $^{167}$Er, $^{168}$Er, $^{170}$Er $^{171}$Yb, $^{172}$Yb, $^{174}$Yb, $^{176}$Yb $Ac^{nr}$ = $^{233}Th^{4+}$, $^{231}Pa^{4+}$, $^{234}U^{4+/6+}$, $^{238}U^{4+/6+}$, $^{237}Np^{4+/6+}$, $^{239}Pu^{4+/6+}$, $^{243}Am^{3+/6+}$

EXAMPLE 32

Compound 90 is a coordinate compound of an actinide and 8-hydroxyquinoline which intercalates DNA directly.

90 is synthesized using the indicated Mossbauer isotopes by the procedures referenced in *The Actinide Elements*, K. W. Bagnall, (1972) pp. 211–229, incorporated by reference.

-continued

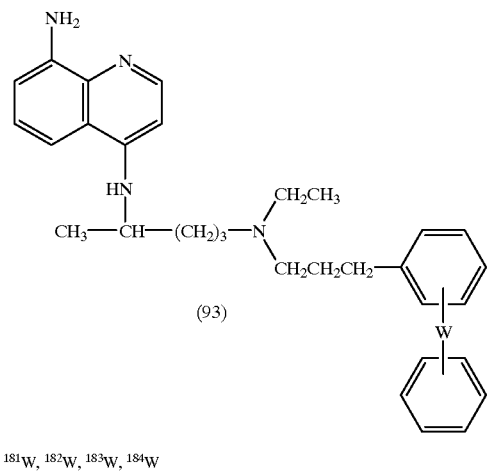

(93)

W = $^{181}$W, $^{182}$W, $^{183}$W, $^{184}$W

EXAMPLE 34

Compound 96 is prepared as follows:

Alkyl halogen derivatized bis(arene) tungsten compound 91, is reacted with the carboxylate derivatized Anthramycin 95, to give the product 96 which is the preferred product of the mixture which could result from substitution at the hydroxyl groups.

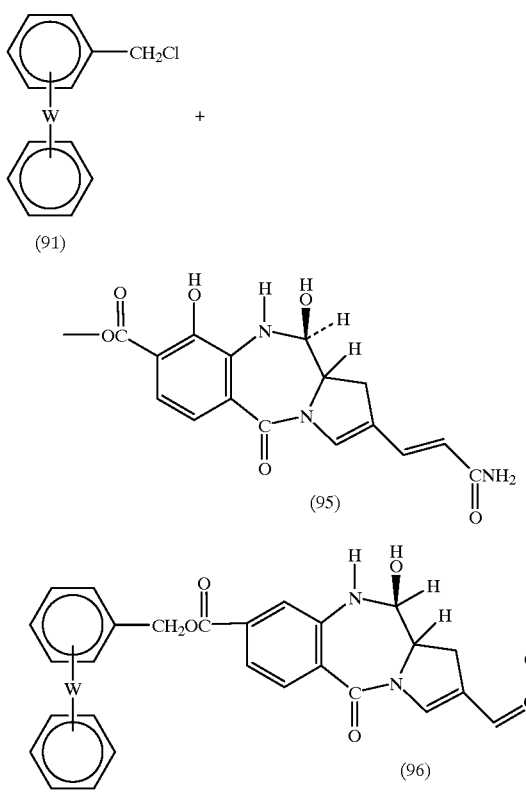

EXAMPLE 35

Compound 100 is prepared as follows:

Osmocene 97, is prepared from osmiumtetrachloride and sodium pentadienide as described in *Comprehensive Organometallic Chemistry,* Geoffrey Wilkinson, Editor, (1982), Vol. 4, p. 1018, incorporated by reference. Osmocene is acylated to give ketone 98 as described in the above reference. 98 is reacted with an ylid derivative of acridine 99, to give the product 100.

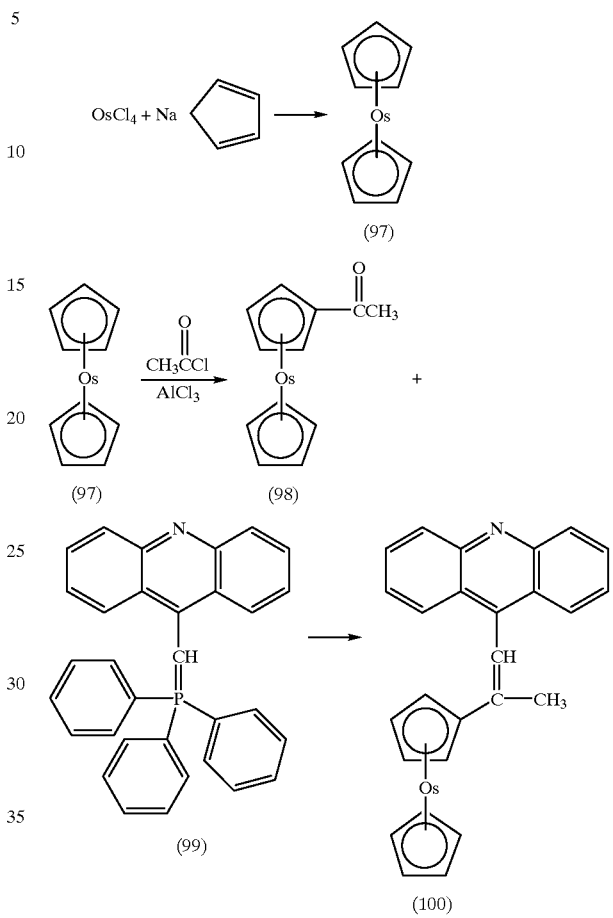

EXAMPLE 36

Compound 103 is prepared as follows:

Methylalcohol derivatized osmocene 101, which is prepared according to the method described in *Comprehensive Organometallic Chemistry,* Geoffrey Wilkinson, Editor, (1982), Vol. 4, p. 1018 (incorporated by reference) is reacted with the tosylate derivative of Mitomycin, C 102, to give the product 103.

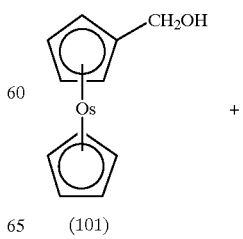

(101)

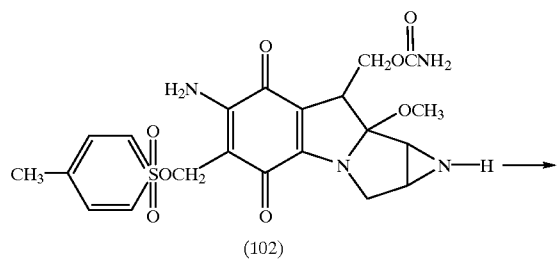

(102)

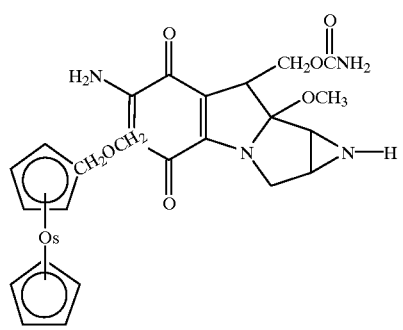

(103)

EXAMPLE 37

Compound 106 is prepared as follows:

The diazonium derivative of Mithramycin 105, is prepared by treating the amino derivative 104, with nitrous acid. The diazonium derivative is reacted with aqueous potassium iodide to give the product 106.

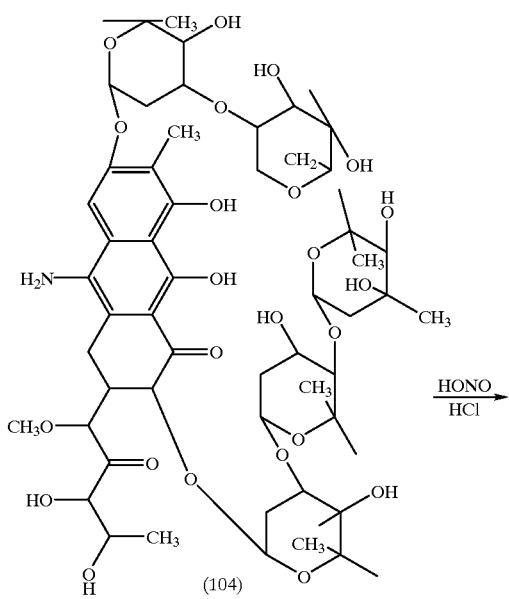

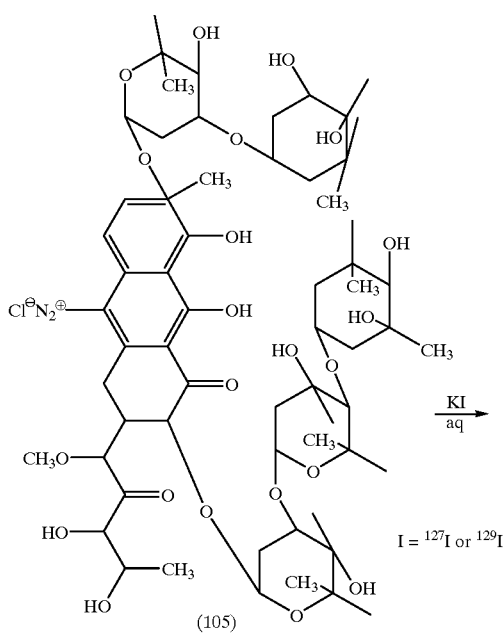

$I = {}^{127}I$ or ${}^{129}I$ (105)

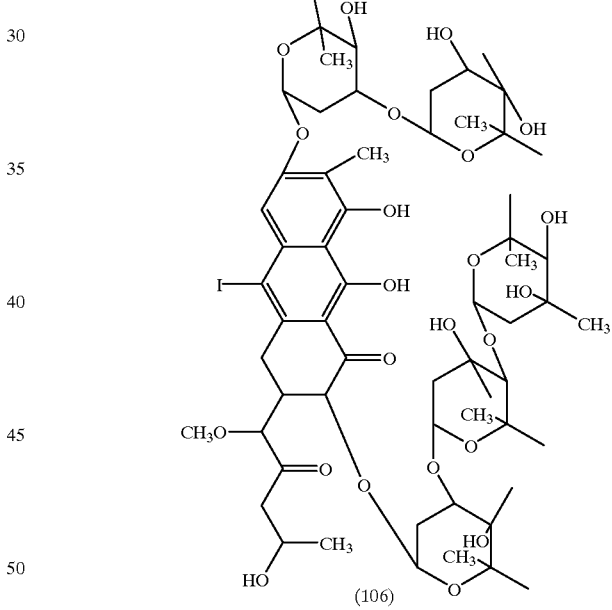

(106)

EXAMPLE 38

Compound 108 is prepared as follows:

The amino derivative of benzo[a] pyrene 107 is iodinated by treatment with nitrous acid then aqueous potassium iodide.

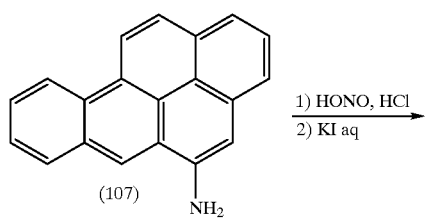
(107)
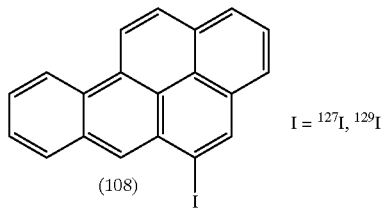
(108) I = $^{127}$I, $^{129}$I
EXAMPLE 39
Compound 110 is prepared as follows:
The amino derivatized quinoline antibiotic 109, is iodinated by treatment with nitrous acid and aqueous potassium iodide to give the product 110. The reaction is carried out under cold conditions to prevent hydrolysis of the antibiotic.
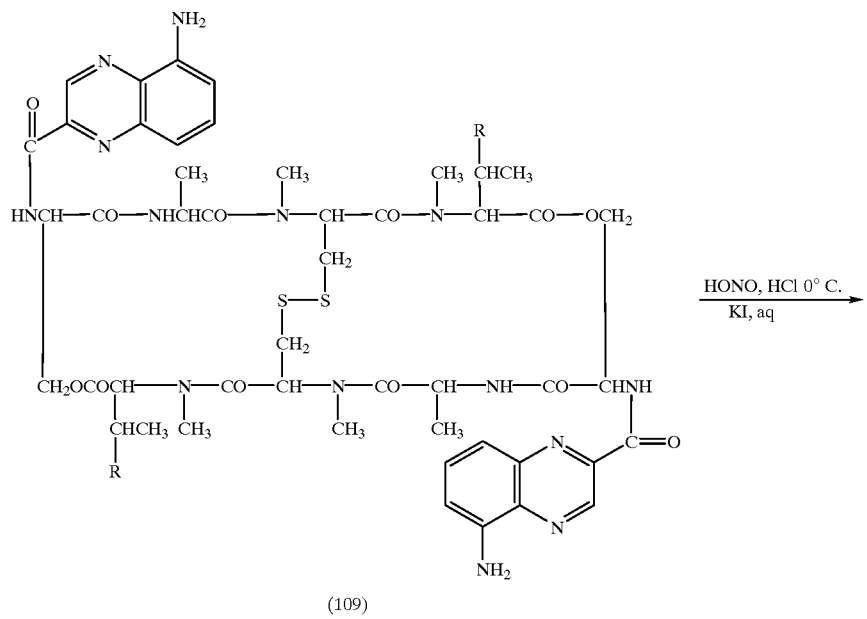
(109)
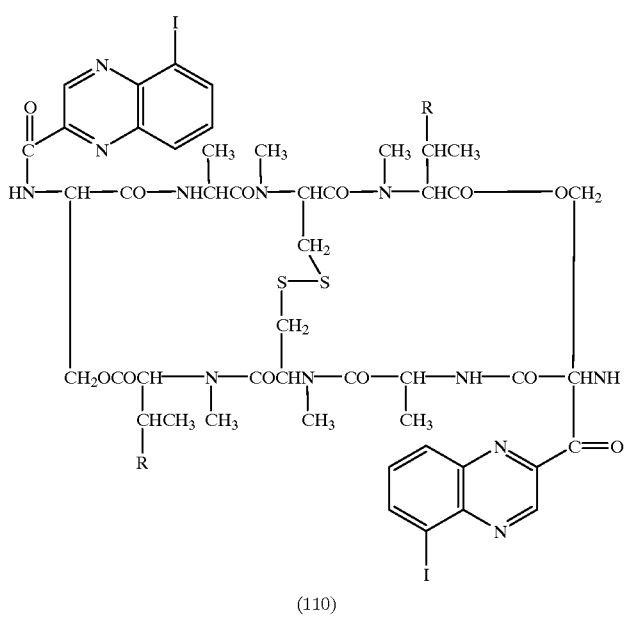
(110)
I = $^{127}$I, $^{129}$I

EXAMPLE 40

Compound 112 is prepared as follows:

Amino derivatized naphthothiopheneethanolamine 111, is iodinated by treatment with nitrous acid and aqueous potassium iodide to give the product 112.

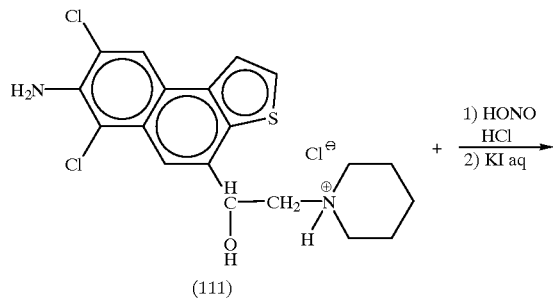

(111)

(112)

$I = {}^{127}I, {}^{129}I$

EXAMPLE 41

Compound 115 is prepared as follows:

Hafnium adduct 113 is reacted with 8-hydroxyquinoline 114 to give the product 115 as described in *Comprehensive Organometallic Chemistry*, Geoffrey Wilkinson, Editor, (1982), Vol 3, p. 565 (incorporated by reference) where 113 is prepared as described in the same reference p. 569.

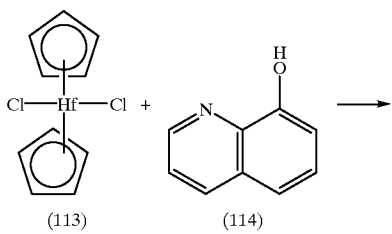

(113)    (114)

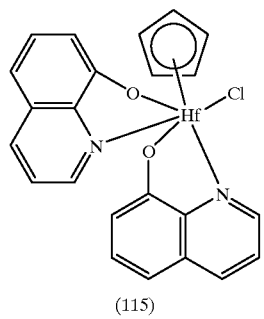

(115)

$Hf = {}^{176}Hf, {}^{177}Hf, {}^{178}Hf, {}^{180}Hf$

EXAMPLE 42

Compound 118 is prepared as follows:

The alkyl chloride hafnium compound 116 which is prepared by preparing the methyl substituted bis (cyclopentadienyl) hafnium dichloride as described in *Comprehensive Organometallic Chemistry*, Geoffrey Wilkinson, Editor, (1982), Vol. 3, pp. 569–570 (incorporated by reference) which is chlorinated, and 116 is isolated from the product mixture and is reacted with proflavine 17, to give the product 118 where the disubstituted product is anticipated, and utility is expected.

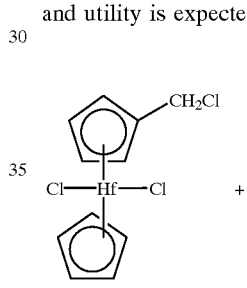

(116)

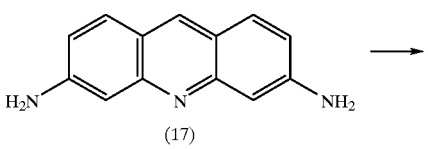

(17)

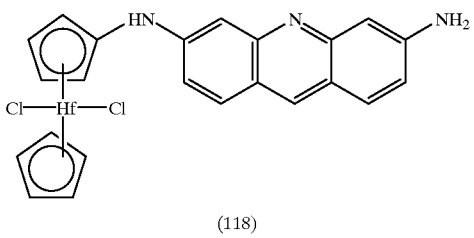

(118)

EXAMPLE 43

Compound 121 is prepared as follows:

The alkyl chloride hafnium compound 116 is reacted with Hoechst 33258 120, to give the product 121.

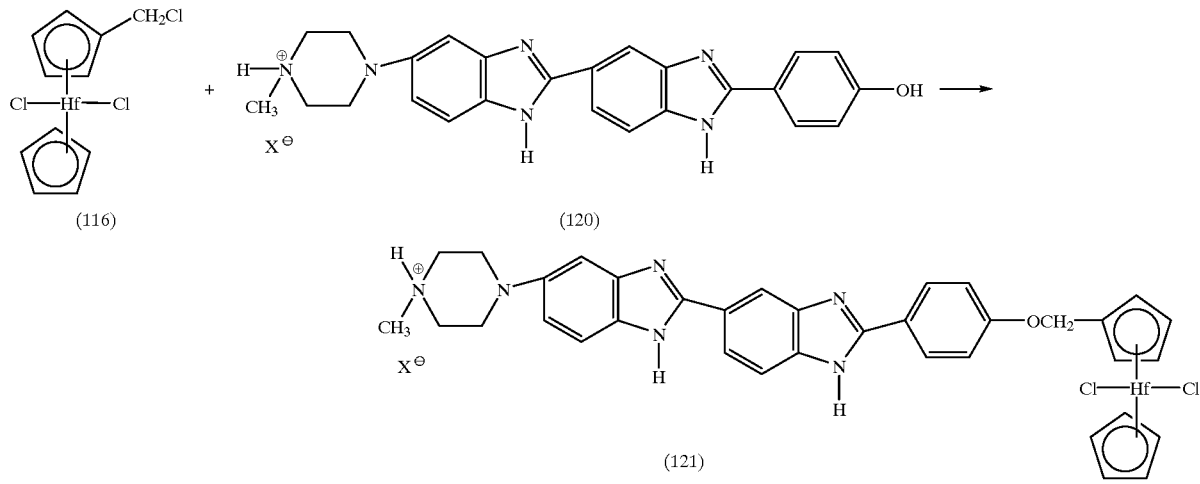

EXAMPLE 44

Compound 126 is prepared as follows:

Tantalum alcohol adduct 122 which is prepared by using the synthetic route of Wilkinson, G. and Birmingham, J. M., Journal of the American Chemical Society, (1954), Vol. 76, pp. 4281–4284 (incorporated by reference) with the exceptions that follow: In addition to cyclopentadiene, methyl substituted cyclopentadiene is used as a starting material to prepare the methyl-bis-cyclopentadienyl chloride of tantalum. This compound is chlorinated to yield 127 which is treated with hydroxide to yield 122. This alcohol is reacted with p-toluenesulphonylchloride 123 to form the tosylate 124 which is reacted with the hydroxy derivative of psoralen 125, to give the product 126.

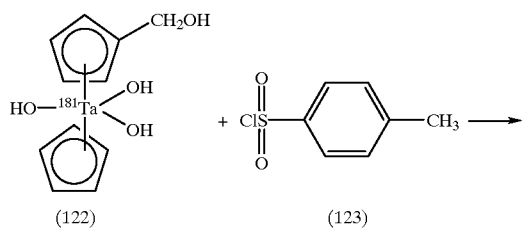

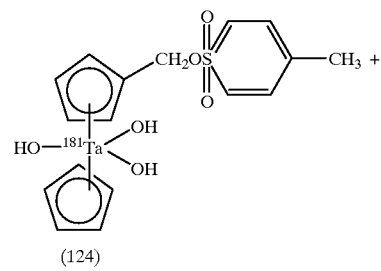

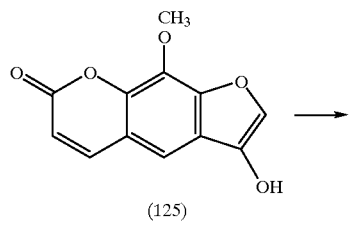

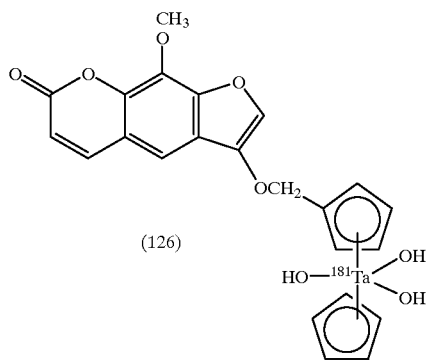

EXAMPLE 45

Compound 129 is prepared as follows:

The alkyl chloride adduct of tantalum 127, is reacted with Berenil 128, to give the product 129. Other substitution products are expected, and utility is expected.

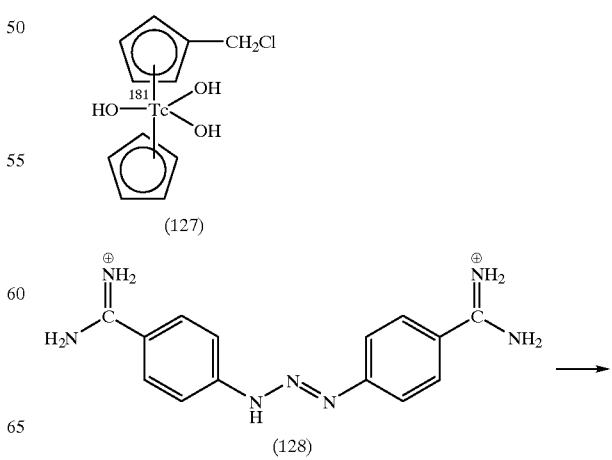

-continued

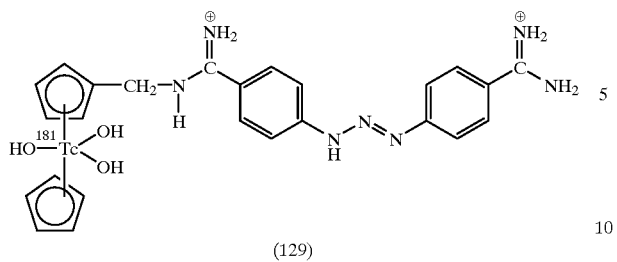

(129)

-continued

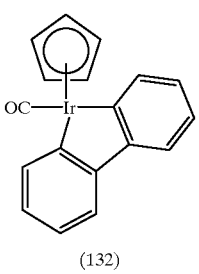

(132)

Ir = $^{191}$Ir, $^{193}$Ir

EXAMPLE 46

Compound 132 is prepared as follows:

Diphenyldilithium compound 130, is reacted with iridium adduct 131 to give the product 132 by the procedure described by Gardner, S. A., et al, Journal of Organometallic Chemistry, 60 (1973) 179–188, incorporated by reference.

EXAMPLE 47

Compound 137 is prepared as follows:

Iridium adduct 133 is reacted with diazonium adduct 134 to give the o-metallated adduct 135 according to the method of Farrell, N.; et al, Journal of the Chemical Society, Dalton, Trans., 1977, 2124, incorporated by reference. 135 is reacted with phenanthridine 136, to give the product 131 where other substitution products are anticipated and utility is expected.

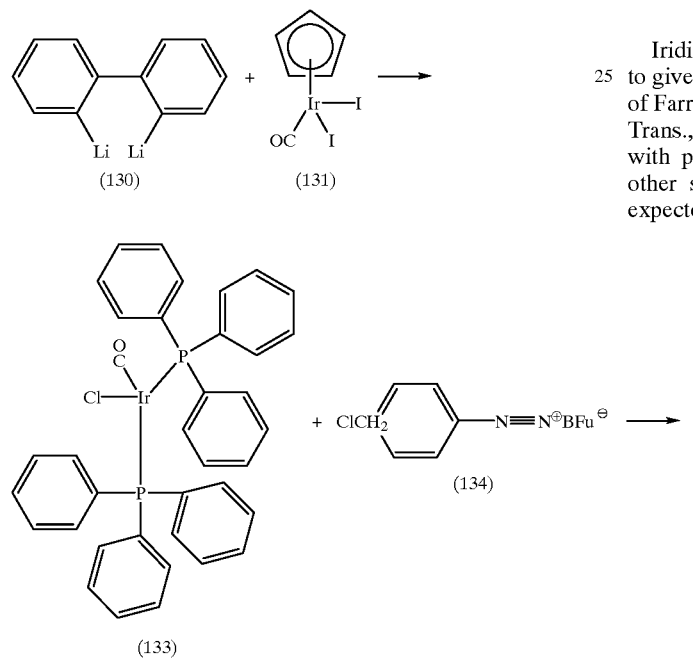

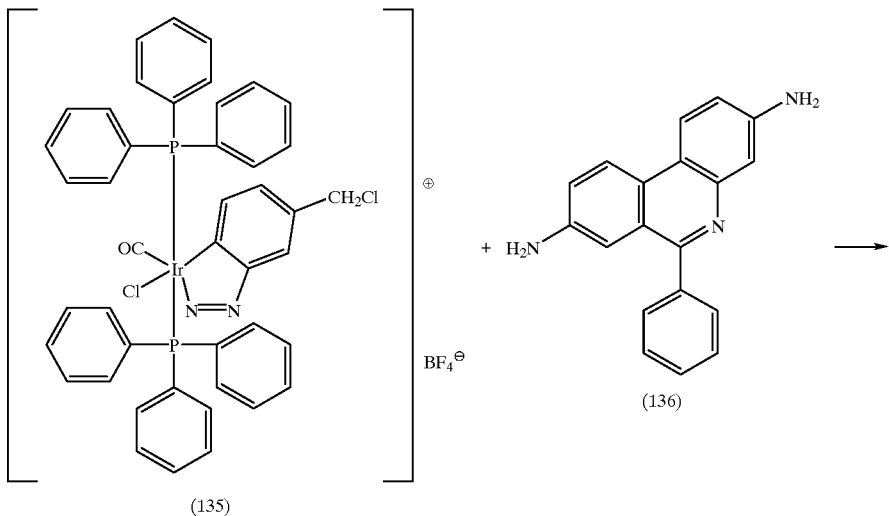

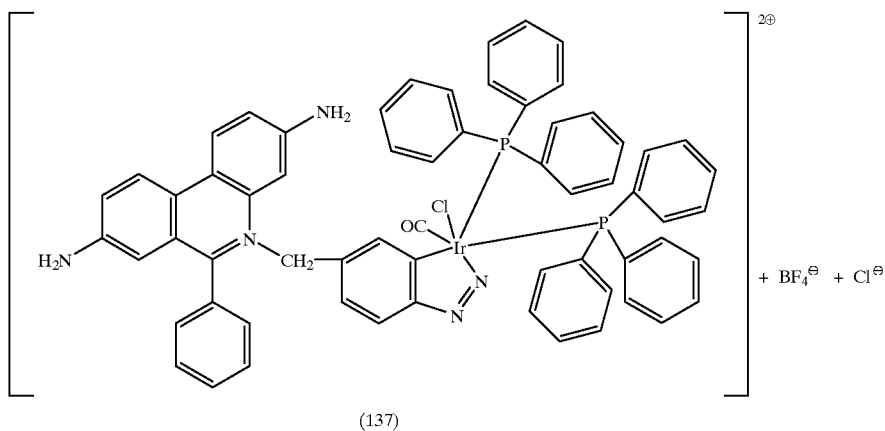

(137)

EXAMPLE 48

Compound 142 is prepared as follows:

Iridium compound 138 is reacted with Grignard reagent 139 followed by chlorination to give chloride adduct 140 according to the procedure of Rausch, M. D. and Moser, G. A., Inorganic Chemistry, Vol. 13, No. 1, 1974, pp. 11–13, incorporated by reference. 140 is isolated from the reaction mixture and reacted with the alkyl amine derivative of psoralen 141, to give the product 142.

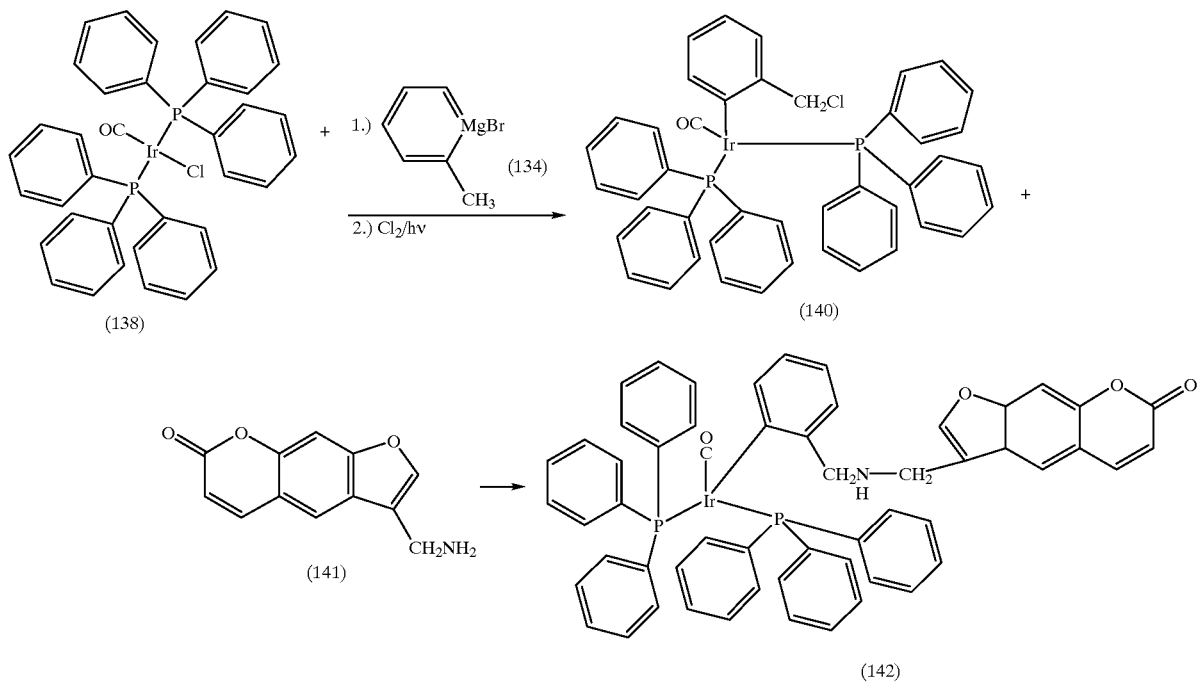

EXAMPLE 49

Compound 145 is prepared as follows:

Sodium hexachloroiridium (III) is reacted with benzo[h]quinoline 143 to give 144 which is reacted with tributylphosphine 119, to give product 145 as described in *Comprehensive Organometallic Chemistry*, Geoffrey Wilkinson, Editor, (1982) Vol 5, p. 587, incorporated by reference.

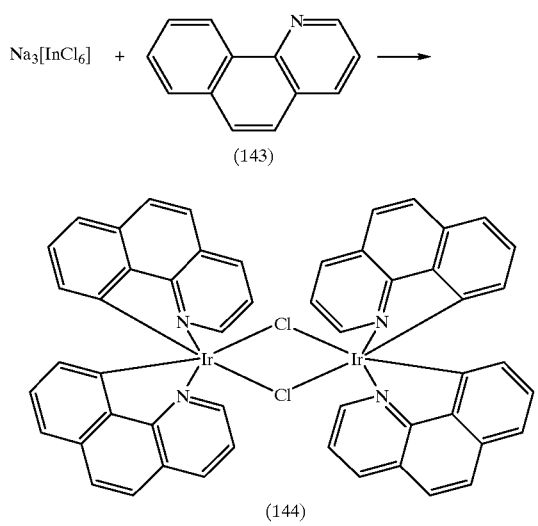
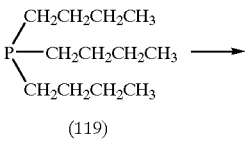
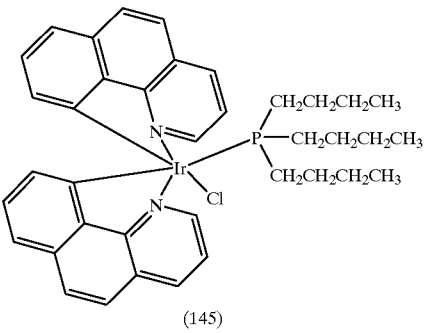

EXAMPLE 50

Compound 150 is prepared as follows:

Iridium adduct 146 is reacted with phosphine compound 147 to give o-metallated adduct 148 according to the procedure described in *Comprehensive Organometallic Chemistry,* Geoffrey Wilkinson, Editor, (1982), Vol. 5, pp. 578–587, incorporated by reference. 148 is acylated with an acid chloride derivative of acridine 149, to give the product 150. Substitution at any of the other aromatic sites can occur, and any of these side products are of equal utility.

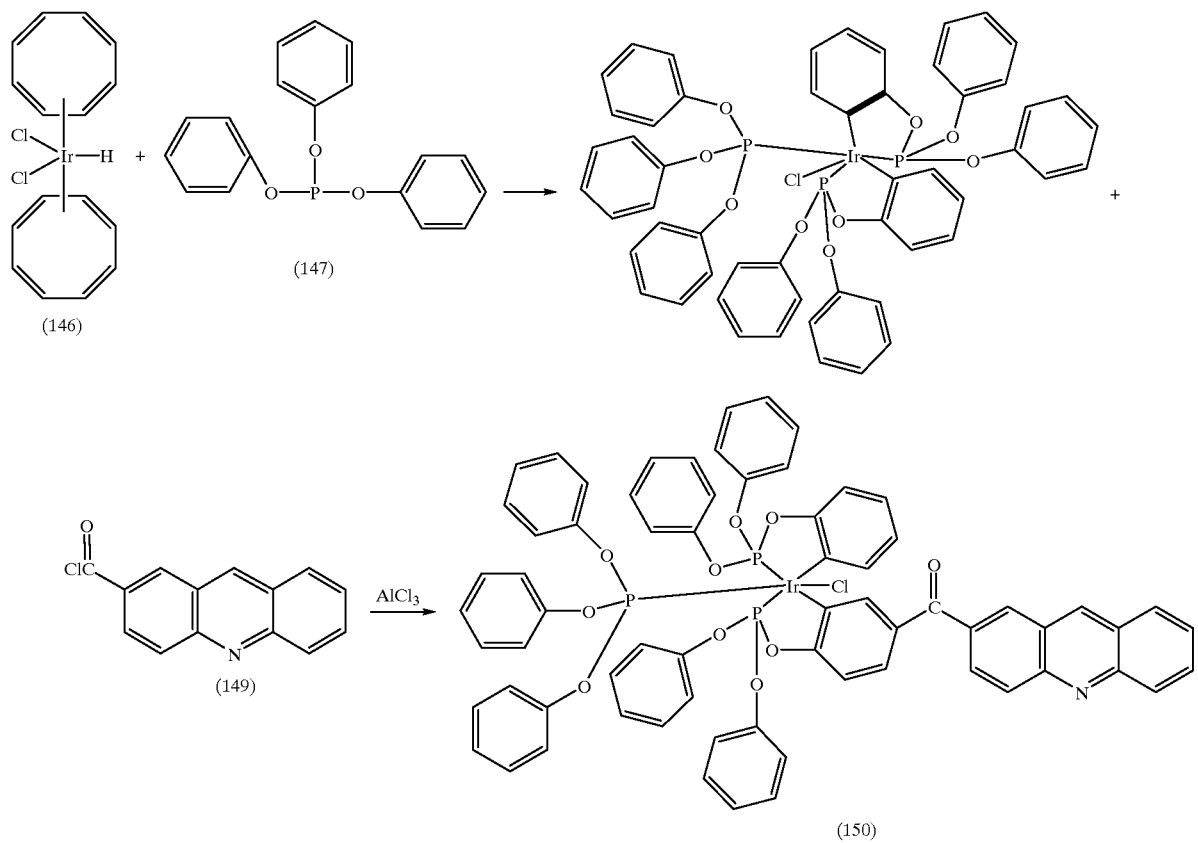

EXAMPLE 51

Compound 153 is prepared as follows:

The crown ether 18-crown-6 151, is reacted with Tilorone derivative 152, to give the product 153.

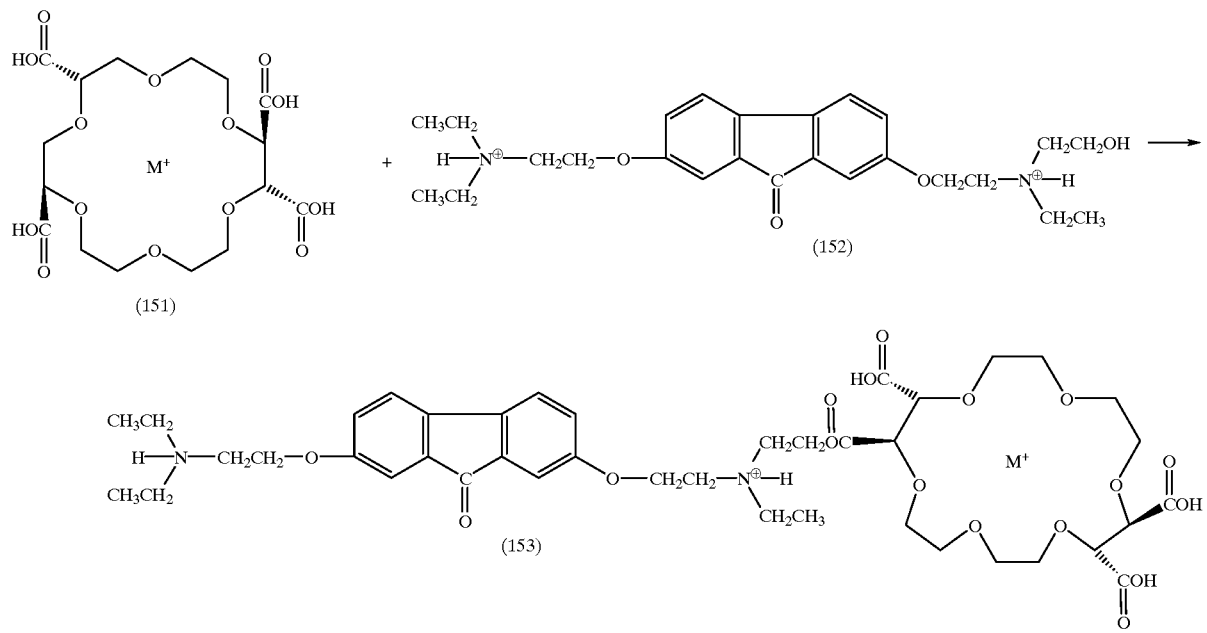

$M^+ = {}^{40}K, {}^{133}Cs$

EXAMPLE 52

Compound 158 is prepared as follows:

Acid chloride derivatized ferrocene 154, is prepared by treatment of the ferrocene carboxylic acid whose synthesis is described in *Comprehensive Organometallic Chemistry*, Geoffrey Wilkinson, Editor, (1982), Vol. 4, p. 476 (incorporated by reference) with oxalyl chloride; 154 is reacted with 1,3,4-butanetriol 155, followed by isolation of 156 from the reaction mixture. Compound 156 is reacted with methylsulfonyl chloride 157 to give the product 158 which is a derivative of Bulsulfan.

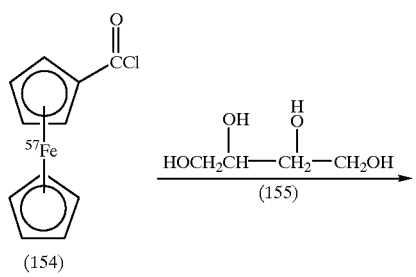

-continued

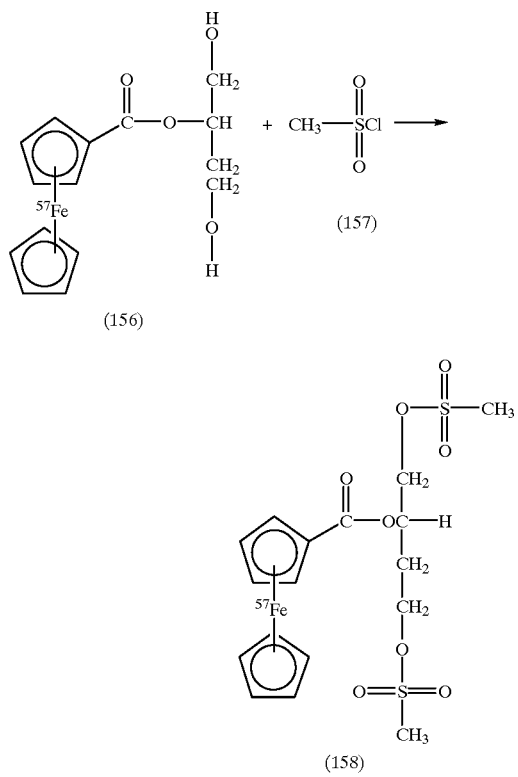

Macromolecular MIRAGE Pharmaceuticals

MIRAGE imaging compounds include those that are generally used in nuclear medicine and are massive in a recoil sense. When a Mossbauer absorber atom is bound to a massive compound the effective mass of the atom becomes the mass of the compound; therefore the recoil energy is not transferred to the Mossbauer atom, and resonant recoilless absorption which is the Mossbauer phenomenon occurs. This effect is discussed in the Theoretical Section. Examples of massive imaging compounds include the colloids described in the Image Scanning Section where the radioactive atoms are replaced with Mossbauer absorber atoms having a low internal conversion coefficient or inorganic or organic molecules possessing Mossbauer absorber atoms having a low internal conversion coefficient where the substitute atoms or molecules form the same type of bonding as the substituted radioactive atoms. Mossbauer compound, $^{197}$Au colloidal gold and antimony 121 sulfide colloid are examples of this type of imaging compound.

Furthermore, MIRAGE compounds for diagnosis and therapy, in addition to the compounds described in the Structure and Exemplary Material Sections, are compounds containing Mossbauer absorber atom(s) and are massive in a recoil sense or are compounds containing Mossbauer absorber atoms which become incorporated into the biological media as part of a massive compound which includes polymer molecules such as proteins or crystalline structures such as bone.

The inherently massive compounds are organic or inorganic polymers, colloids, gelatin and dextran protected colloids, water insoluble macroaggregates or crystals or combinations thereof which contain Mossbauer absorber atoms which are covalently or ionically bound to these carrier molecules or exist in a metallic, inorganic, or organic form as occlusions or inclusions in these carrier molecules. Polymer MIRAGE pharmaceuticals include proteins labeled with Mossbauer absorber atoms such as $^{57}$Fe hemoglobin, $^{127}$I and $^{129}$I labeled thyroxine, $^{119}$Sn, $^{121}$Sb, $^{125}$Te, $^{73}$Ge, $^{127}$I, $^{129}$I, and $^{201}$Hg labeled albumin and organic and inorganic polymers of the size range of approximately 5–50 nm with Mossbauer absorber atoms bound covalently, by chelation, by coordination, or electrostatically. Examples include dibutyltin(119) dimethylacrylate, ruthenium(99) bisbipyridine poly 4-vinyl-pyridine, poly[bis bipyridine osmium(189) bis vinylpyridine], $^{57}$Fe polyvinyl-ferrocene, sulfonated polystyrene and Nafion and polymers containing ethylenediaminetetra acetate and organo silane-styrene sulfonate copolymers containing trapped cations of Mossbauer absorber atoms including those cations of the lanthqnide, actinide and transition metals.

The colloids include carboxyl, sulphate, phosphate, hydroxide, and sulfide colloids containing Mossbauer absorber atoms exclusively with the appropriate counter ion(s). Examples are antimony 121 sulfide colloid and $^{197}$Au colloidal gold. Or, the colloids contain Mossbauer absorber atoms in metallic, inorganic, or organic form as inclusions and occlusions. Carrier colloids of this type include carboxyl, sulphate, phosphate, hydroxide, and sulfide colloids and gelatin and dextran protected colloids and micelles. Specific examples are Tc sulfur colloid, chromic phosphate colloid, antimony sulfide colloid and dextran and gelatin protected colloidals, yttrium hydroxide and colloidal gold, containing inclusions or occlusions of cations of Mossbauer absorber atoms including those cations of the lanthanide, actinide, and transition metals. Micelles include soaps and carry organic compounds containing Mossbauer absorber atoms such as benzene labeled with $^{125}$Te or $^{119}$Sn.

Water insoluble macroaggregates include $^{57}$Fe ferric hydroxide and ferric hydroxide macroaggregate containing occlusions and inclusions including the aforementioned cations. Crystals include water insoluble microprecipitates of the approximate size range of 5–50 nm of cations or anions of Mossbauer absorber atoms such as $^{125}$I$^-$ and $^{129}$I$^-$, AgI or silver halide micropricipitates containing Mossbauer absorber atoms in metallic, inorganic, or organic form as inclusions or occlusions in the crystal including all of the aforementioned cations of the lanthanides, actinides, and transition metals, and metallic and inorganic forms of these isotopes.

Polymer compounds are prepared by attaching Mossbauer absorber atoms or organic functionalities containing Mossbauer absorber atoms to an organic polymer carrier by using the type of reactions described in the General Synthetic Pathways and Exemplary Materials Sections, or these types of reactions are used to attach Mossbauer absorber atoms to monomers which are polymerized to produce particles of the approximate size range of 5–50 nm by reactions generally known to one skilled in the art. For the cases where the Mossbauer absorber atoms are held by chelation, coordinate, or electrostatic bonding, the atoms are exchanged into the polymer backbone by reactions generally known to one skilled in the art.

MIRAGE compounds which are inorganic polymers or colloids, or micelles or water insoluble macroaggregates or crystals or combinations thereof and consist of Mossbauer absorber atoms or functionalities containing Mossbauer absorber atoms and counterions or contain inclusions or occlusions of Mossbauer absorber atoms are prepared by preparing the Mossbauer atoms or functionalities containing Mossbauer absorber atoms and the other starting reagents of the carrier compounds in the proper physical form and by allowing them to form condensation nuclei and grow in solution and by isolating the product by filtration or evaporation of the solvent using reactions and techniques generally known to one skilled in the art.

For example, sodium thiosulfate is treated with HCl and technicium pertechnitate to give Tc sulfur colloid. And, gold colloid is prepared by reducing a solution of gold chloride with ascorbic acid or by heating gold chloride with an alkaline glucose solution in the presence of gelatin. The product in each case can be obtained by removing the solvent by vacuum distillation.

Additional MIRAGE compounds for diagnosis and therapy include those compounds which contain mossbauer absorber atoms which become incorporated into biological molecules which are massive in a recoil sense following administration of the compounds. Such compounds which contain Mossbauer atoms in a form to permit incorporation into proteins include water soluble ionic compounds containing a Mossbauer absorber atom(s), as the cation or anion such as those which dissolve in water to release $^{57}$Fe$^{3+}$ which is incorporated into hemeproteins and $^{127}$I$^-$ or $^{129}$I$^-$ which is incorporated into thyroid compounds. Mossbauer atoms which can be incorporated into bone as occlusions and inclusions include inorganic and metallic forms of $^{40}$K, $^{153}$Gd, $^{155}$Gd, $^{157}$Gd, $^{161}$Dy, $^{163}$Dy, and $^{149}$Sm. The corresponding MIRAGE pharmaceuticals are water soluble ionic compounds, colloids, crystals, or macroaggregates containing bone seeking Mossbauer absorber atoms in ionic form or the MIRAGE pharmaceuticals are carrier compounds such as colloids, crystals, or macroaggregates possessing bone seeking Mossbauer absorber atoms in an inorganic or metallic form as occlusions or inclusions. These compounds are prepared as described previously.

PREPARATIONS AND ROUTES OF ADMINISTRATION

MIRAGE pharmaceuticals alone or combined with carrier molecules can be administered orally, as sprays, intramuscularly, intravenously, or by subcutaneous, intra-articular, or intra-arterial injection.

Medicinal formulations which contain one or more MIRAGE compounds as the active compound can be prepared by mixing the MIRAGE pharmaceutical(s) with one or more pharmacologically acceptable excipients or diluents, such as, for example, fillers, emulsifiers, lubricants, flavor correcting agents, dyestuffs or buffer substances, and converting the mixture into a suitable galenic formulation form, such as, for example, tablets, dragees, capsules or a solution or suspension suitable for parenteral administration. Examples of excipients or diluents which may be mentioned are tragacanth, lactose, talc, agar-agar, polyglycols, ethanol and water. Suspensions or solution in water, dextrose, saline, or dimethyl sulfoxide can preferably be used for parenteral administration.

Also, MIRAGE pharmaceuticals can be prepared as sterile lyophilized powder to which a sterile solvent such as water or dimethylsulfoxide is added. MIRAGE pharmaceuticals are also prepared as a sterile lyophilized powder containing deoxycholate to effect a colloidal dispersion of insoluble MIRAGE pharmaceutical. These preparations are administered as injectables including intramuscular and intravenous administration.

Topical MIRAGE pharmaceuticals can be prepared as a cream, lotion, gel, ointment, and spray.

It is also possible to administer the active compounds as such without excipients or diluents, in a suitable form, for example in capsules.

MIRAGE pharmaceuticals can be packaged employing the usual sorts of precautions which the pharmacist generally observes. For example, the preparations may be packaged in light protecting vials and may be refrigerated if necessary.

THE APPARATUS

The overall operation of the system may be exemplified by the $Co^{57}/Fe^{57}$ Mossbauer pair as follows: the radioactive source in the form of a thin film of material such as stainless steel, copper, or palladium into which radioactive Co-57 has been allowed to diffuse to provide a beam of highly homogeneous photons having an average energy of 14.4 KeV. The homogeneity, or line width $\Delta E$ is $4.5 \times 10^{-9}$ eV so that $\Delta E/E$ is less than $10^{-12}$. A filter selects the 14.4 KeV photon from the other two photons of different energy.

The source is mounted on an accurately controlled mass drive, which shifts the energy or frequency of the photon by the Doppler effect. A wide variety of commercially available velocity drives exist. A velocity of 1 mm/sec corresponds to an energy change of $4.8 \times 10^{-8}$ eV or more than ten line widths. The arrangement 100 shown in FIG. 1 is one in which the source 50 is mounted on a cone 62 of a speaker 60 and the speaker is driven so that the relative position of the speaker coil increases and decreases linearly with time (symmetric triangular wave form) at approximately 5 Hz. Since the displacement of the speaker coil is quite closely proportional to the input voltage, it is necessary to provide a ramp voltage in order to produce a linear velocity. This is accomplished by a triangular wave. A function generator 54 is employed to produce an accurate, low frequency triangular voltage. This voltage is applied to the speaker 60 through a power amplifier 56. In practice, it is necessary to employ considerable negative feedback to produce an accurate linear velocity. This is accomplished by coupling a second (or using a double voice coil 64) speaker 66 to the drive speaker 60 with a rigid rod 52, and providing the error signal from the second speaker (monitored by oscilloscope 58) to the amplifier 56 through the integrator 68 as shown schematically in FIG. 1. The source 50 is mounted on the rod connecting the two speakers.

Since the source executes two velocity excursions, one at positive and one at negative velocities, a synchronized shutter 70 can be used to block radiation during the non-resonant excursion.

In addition to tuning the energy via a Doppler shift, the emission energy of a Mossbauer source is continuously tunable by driving it ultrasonically. A Mossbauer source can be adhered to a piezo-electric transducer such as a quartz or barium titanate transducer and driven at ultrasonic frequencies to produce an infinite number of side bands in the emitted radiation which are removed from the central, unshifted line by an integer multiple of the ultrasonic frequency and the relative amplitudes of the side bands can be varied by varying the power applied to the transducer. The ultrasonic Mossbauer side bands can serve as a variable-frequency energy source. The ultrasonic power is selected so that essentially only the first side bands have appreciable intensity and the ultrasonic driving frequency is chosen so that the emission sidebands are of the desired energy. A variable-frequency ultrasonic Mossbauer spectrometer based on this principle is described by J. Mishory and D. I. Bolef, *Mossbauer Effect Methodology*, Irwin J. Gruverman, Editor, Vol. 4, (1968) pp. 13–35, incorporated by reference.

Figure 7:
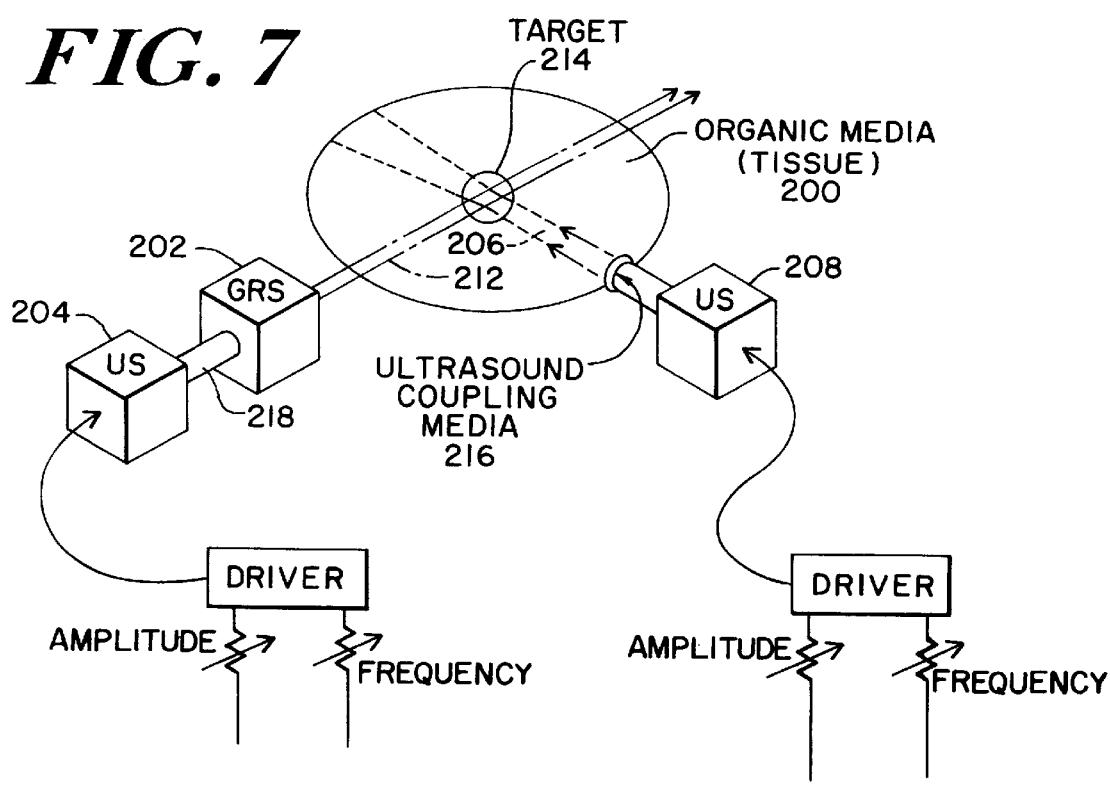
FIG. 7 is an isometric drawing of a system according to the present invention showing ultrasound modulation of the gamma ray source and the Mossbauer atom at the target area.

In one embodiment, ultrasonic tuning of the gamma ray source 202 is shown in FIG. 7 where a source 204 of ultrasonic energy energizes the gamma ray source 202 through an acoustic coupling media to produce emission side bands of energy which is tunable by changing the ultrasonic driving frequency.

The source, or emitter of radiation, can also include the techniques known to Mossbauer spectroscopy of narrowing the line width or absorbing unwanted Mossbauer lines. In addition, unwanted radiation such as particle radiation can be absorbed by a filter and wanted electromagnetic radiation can be separated from unwanted electromagnetic radiation by addition of single frequency filter 80 shown in FIG. 2. The filter 80, receives source 50 radiation through an input collimator 82 and enters a diffraction crystal 84. Since the diffraction angle can be calculated (Bragg equation $n\lambda = 2d \sin\theta$), the desired frequency is selected by placement of a second output collimator 86 and the selection of a crystal having an appropriate intranuclear layer distance (d).

In addition to the above-mentioned photon sources, the photon emitters of Table 7 are useful in conjunction with the correspondingly listed absorbers incorporated as pharmaceutical agents.

Fluorescence, or nuclear emissions of the tissue components excited at the Mossbauer frequency can be observed from the target area. The dynamic range (signal-to-noise) can be enhanced by viewing the subject 90 shown in FIG. 1 off-axis from the incident radiation from the source, thereby eliminating the background level from the source. Off-axis viewing is possible due to the continuum of angles of fluorescent emission of the target tissue component at the Mossbauer frequency. Moreover, the frequency of the fluorescence will coincide with the frequency of the source due to the narrow spectrum of the Mossbauer resonance. Also, due to the finite half life of the excited state, fluorescence can be discriminated from exciting radiation by timing the arrival of the signals.

Furthermore, fluorescence can be continuously monitored by sensors such as 92 shown in FIG. 1 to give a characteristic plot of the treatment effectiveness. A spatially distributed system of multiple detectors such as proportional counters or scintillation detectors, or lithium drifted silicon and germanium detectors where each detector has a collimator at the aperture for the entry of photons can localize the source of fluorescence. Photons must travel in a straight line, and each collimator will only permit photons propagating parallel to its axis to enter its detector. Thus, the orientation of the axis of each detector's collimator relative to the treatment field assigns a propagation direction for source gamma rays called a ray path. The direction that gamma rays are being administered assigns another, and signals from multiple detectors at other orientations assign other ray paths. The intersection of two or more ray paths gives the location of the fluorescent source of gamma rays. In addition to the location of the source of fluorescence which is the site of treatment, the intensity at the detectors gives the intensity of treatment. A control signal can be derived from the fluorescence, and combined or processed by processor 94 of FIG. 1 according to the orientation of detectors which record signal direction and the intensity of the recorded signals to continuously control the source of fluorescence to optimize the treatment. And, the apparatus could also be combined with imaging equipment such as computed tomography, magnetic resonance imaging, and ultrasound imaging which could be used to determine the spatial location of the selected tissue to provide the coordinates to be used with the fluorescent signal to control the site of treatment.

Figure 2:
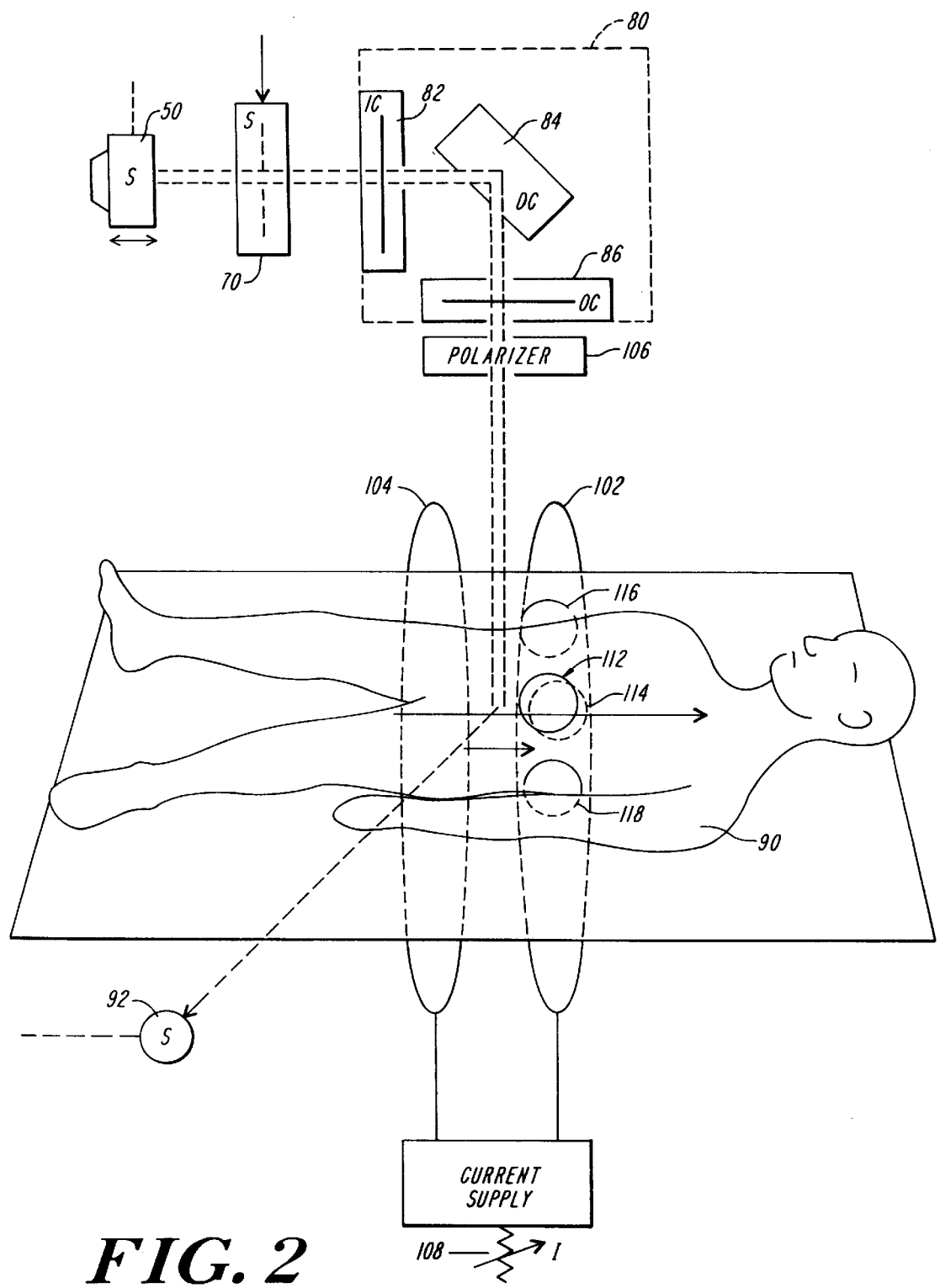
FIG. 2 is an alternate embodiment of the system apparatus of the present invention.

In an alternate design, the imposed magnetic field may be used to produce an energy transition for absorption of the radiation without the necessity of a doppler shift of the gamma source. The requirement of a magnetic field of predetermined magnitude provided by current adjustment 108 of FIG. 2 and direction can be accomplished by using Helmholtz coils or surface coils discussed below. An exemplary apparatus is shown in FIG. 2 which uses Helmholtz coils 102, 104 where the patient 90 is oriented along the z axis of the coils. A uniform field of specified spatial dimensions can be created by varying the radius, a, and the distance, z, between the coils. The field is saddle shaped with the field at the saddle point being uniform and strongly divergent from uniform immediately adjacent to the saddlepoint. The equation for the field of the coils with the current in the same direction is given as follows:

$$H_2 = \frac{NI}{2} \frac{a^2}{(a^2 + z^2)^{3/2}} \qquad (2)$$

Helmholtz coils can be placed in a longitudinal configuration relative to the patient as shown in FIG. 2 and transverse to the patient. A system of such Helmholtz coils are used as described below to effect the field characterstics necessary to cause selective absorption of Mossbauer radiation in the desired location via the mentioned magnetic hyperfine splitting and polarization effects.

Selectivity in treatment is achieved by imposing a magnetic field gradient of sufficient steepness which exploits the dependence of resonance energy on field strength so that resonant absorption can be localized to specific dimensions (such as that of a tumor) while maintaining nonresonant, and therefore nonabsorptive, conditions in the surrounding non-selected tissue at the energy of gamma rays imparted to the tissue. To achieve this situation, the field gradient (field strength difference) must be such that the induced resonant energy difference across the selected space is one line width of the exciting gamma rays.

The parameters and calculations involved are discussed in the Theoretical Section, below.

In one embodiment, a gradient field is produced by the Helmholtz coils of FIG. 2 where the steepest gradient is produced when the induced field from each coil opposes that of the other. The field gradient produced by such configuration of Helmholtz coils is given as follows:

$$G_2 = \frac{\mu_o N I 3 z_o}{a^2 (1 + z_o^2)^{5/2}} \qquad (3)$$

where Zo is the normalized source coordinate. Equation 3 and equations for current distributions to produce desired field gradients appears in U.S. Pat. No. 4,617,516 and its references which are incorporated by reference.

Figure 3:
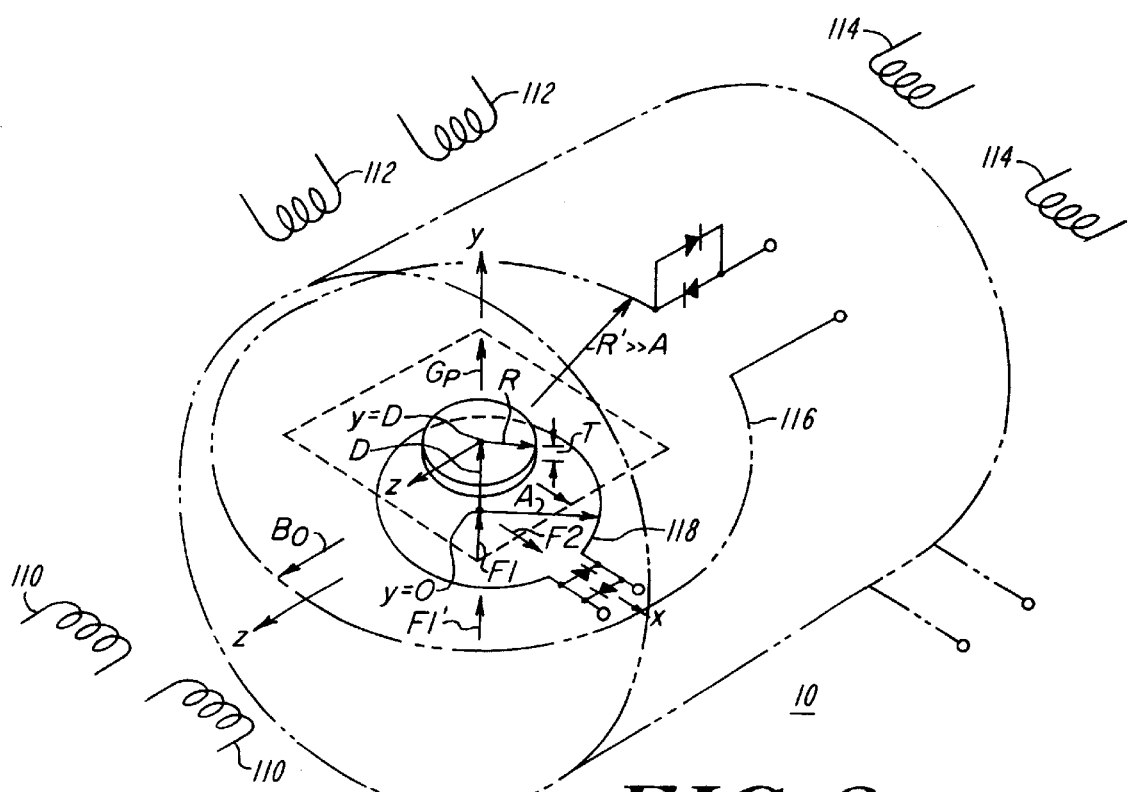
FIG. 3 is an alternate embodiment of a portion of the system of FIGS. 1 or 2, showing the position of surface coils.
Figure 3A:
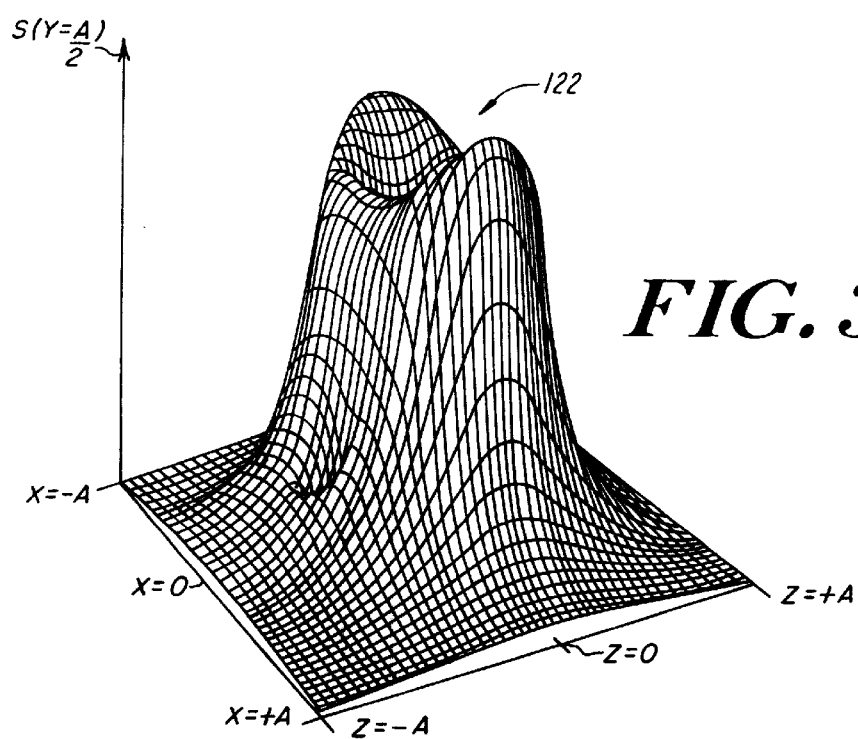
FIG. 3A is a plot of the field produced by the coils disposed in FIG. 3.
Figure 4:
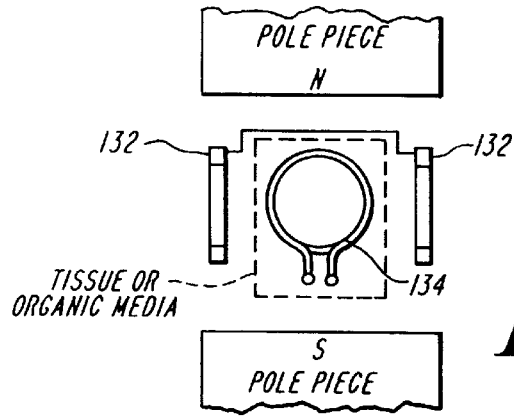
FIG. 4 is an alternate embodiment of the disposition of Helmholtz and a surface coil.
Figure 4A:
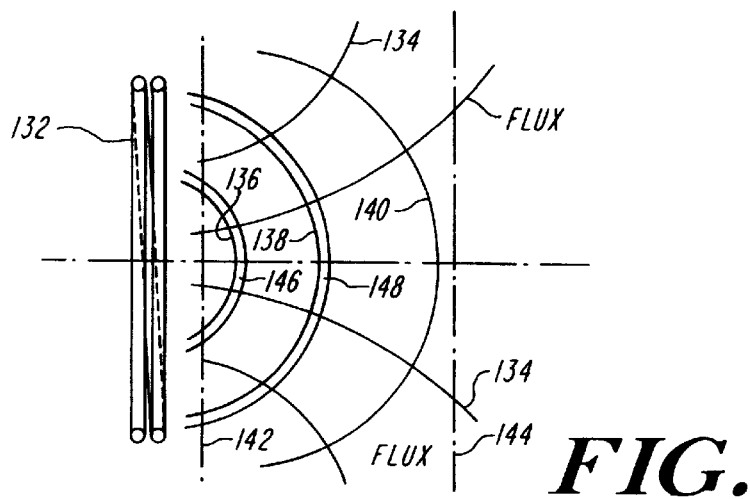
FIG. 4A is a plot of the field produced by the coils of FIG. 4.
Figure 6:
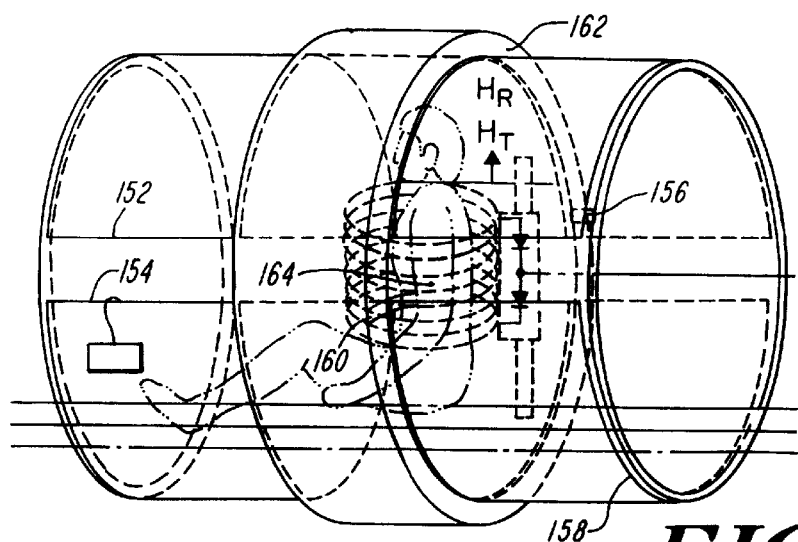
FIG. 6 is an isometric view of an alternate embodiment of an array of coils for use in the system apparatus of FIGS. 1 and 2.

In addition, a magnetic field of high field strength gradient and/or with field lines which change from linear to linear at a 90 degree (perpendicular) angle over a small spatial displacement is produced by Helmholtz surface coils such as 110, 112, 114, and 132, 134 used in magnetic resonance imaging which appear in FIGS. 3 and 4, respectively, and which appear in Nature, Vol. 287 (1980) p. 736 incorporated by reference. Such surface coils can typically achieve field strength gradients of 2000 gauss per centimeter. The corresponding magnetic field lines are shown in FIGS. 3A and 4A, respectively, where a saddlepoint is shown at 122. Moreover, the gradient can be significantly increased in the case where a very high coil current is sustained for a limited time to prevent thermal damage to the coils. Surface coils can be used singularly or in combination to effect the desired field configuration and field gradient. And, the coil dimensions, number of turns, current in each coil, and the relative position of the coils can be adjusted to achieve the desired field. The configuration of FIGS. 3, 4, 5 and 6 can be used with the apparatus of FIGS. 1 and 2 to achieve localization of the Mossbauer effect by exploiting the dependence for resonance on the polarization and propagation direction of the gamma ray for Mossbauer absorber nuclei aligned by the presence of a magnetic field as described in the Theoretical Section, below.

For example, the gamma ray could follow radially directed field lines into the body and cut axial field lines deep in the body at the location of the target tissue. As explained in the Theoretical Section, when the gamma ray has the proper energy, polarization and propagation direction, the nuclear transitions of the Mossbauer atoms in the presence of the parallel field lines are nonresonant with the administered gamma rays while those in the presence of the perpendicular field lines are resonant for the $\Delta m=0$ transition.

Combinations of Helmholtz coil pairs could achieve selectivity by exploiting the conditions for resonance of gamma ray energy, polarization and propagation direction. For example, the pair of Helmholtz coils 102, 104 of FIG. 2 can be used to produce a saddle shaped field where a uniform field parallel to the body axis is produced at the saddle point. As described for a structure of FIG. 6 having coils 152, 154, 156, 158, 160 and 162, the Volume 164 of the field saddle point can be made less than 1 mm$^3$. Furthermore, the transverse component of the magnetic field of a surface coil is zero along its axis, and, the axial field is zero in the equidistant plane of two matched Helmholtz surface coils with opposite currents. The intersection of the axis of the coils with the equidistant plane constitutes the saddle point of these coils.

Spatial treatment selectivity can be achieved at the 1 mm$^3$ volume level by applying surface coils in a configuration of FIG. 2 such that the planes of the surface coils are parallel to each other and perpendicular to the planes of the Helmholtz coils 102, 104 and such that the saddle point of the former superimposes that of the latter. Treatment is carried out such that the gamma rays propagate along the axis of the two surface coils 112 and 114 or along a radial field line in the equidistant plane of the two surface coils 116 and 118. In both cases, the gamma rays would encounter parallel aligned nuclei except at the intercept of the saddle points where the rays would encounter nuclei aligned transversely to the gamma rays' propagation direction, and selective absorption will occur for the $\Delta m=0$ line by the process described in the Theoretical Section.

An alteration of this scheme is to use two pairs of body Helmholtz coils such as those shown in FIG. 2. Each pair is matched, and the current is in opposite directions for one pair and is in the same direction for the other pair. The field produced by the former pair is greater than that produced by the latter. Treatment is performed by administering the gamma rays in the radial direction in the equidistant plane perpendicular to the axis of all four coils. Selectivity is achieved by the polarization and energy mechanism for the $\Delta m=0$ transition as described in the Theoretical Section because the field is predominantly radial except where the gamma ray intersects the coils' axes where the field is predominantly axial. This is because the field contributed by opposing coils is radial with zero longitudinal component at this point; whereas, the field of the coils with the current in the same direction produce a large longitudinal component at this point.

The axes of coils used to produce a magnetic field discussed so far coincide with an axis which passes through the patient. Another configuration of coils to produce a gradient field is two external coils whose common axis does not intersect the body but is aligned parallel to the axis through the body selected as the gradient axis. With such a coil arrangement as demonstrated in FIG. 3, the depth at which the resonance conditions occur can be selected by controlling the ratio of the currents in the two coils.

The coils discussed thus far are Helmholtz coils, shown in FIG. 4, which produce a field as shown in FIG. 4A. In FIG. 4A, the flux pattern of the surface coil 132 is indicated by the lines 134, and the field profile (i.e. lines of constant intensity) are indicated by lines 136, 138, and 140.

The field is rotationally symmetric with respect to the axis of the coil 132, but the component of the field directed perpendicularly to the axis of the coil does not exhibit the same rotational symmetry. For all points off axis, there is a non-zero transverse component. Thus, the surfaces of constant transverse field (whose traces in the plane of FIG. 4A correspond to lines such as 136 to 140) are of somewhat distorted spherical shape. The location of the selected tissue is between lines 142 and 144. In practical terms, it is appropriate to consider the operation in relation to layers of finite thickness corresponding to a resonant condition along the field gradient of one linewidth; two such layers are indicated at 146 and 148 in FIG. 4A.

Figure 5:
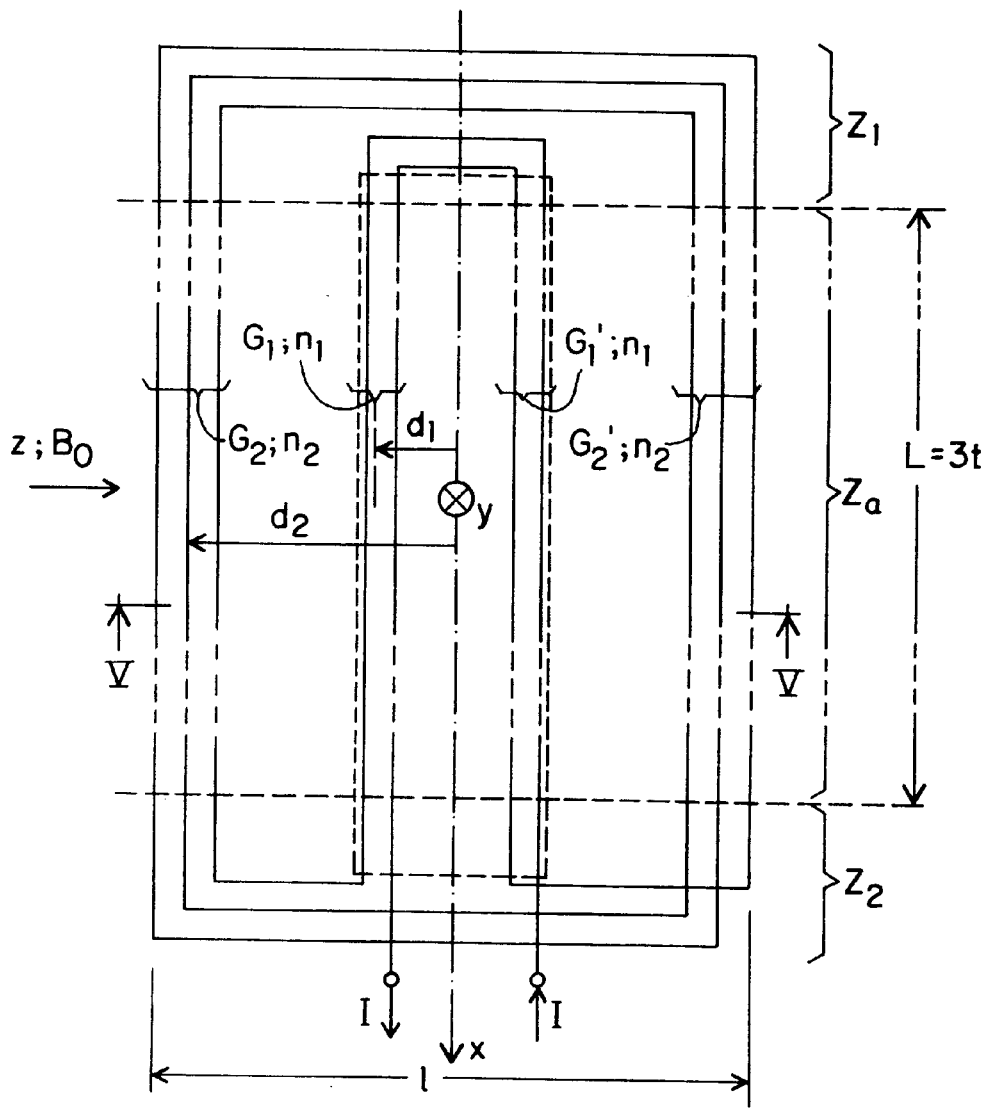
FIGS. 5 and 5A are drawings of a surface coil.
Figure 5A:
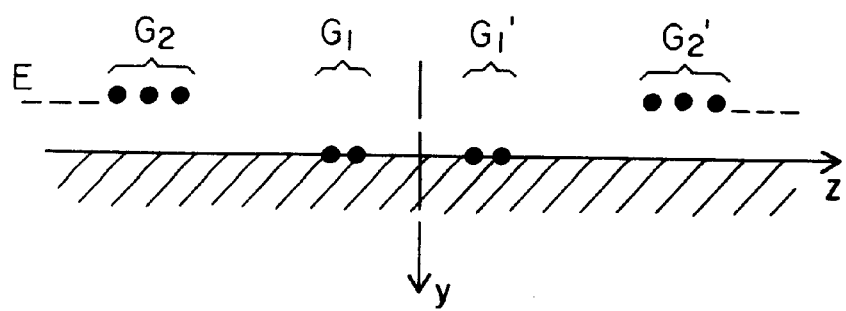
Figure 5B:
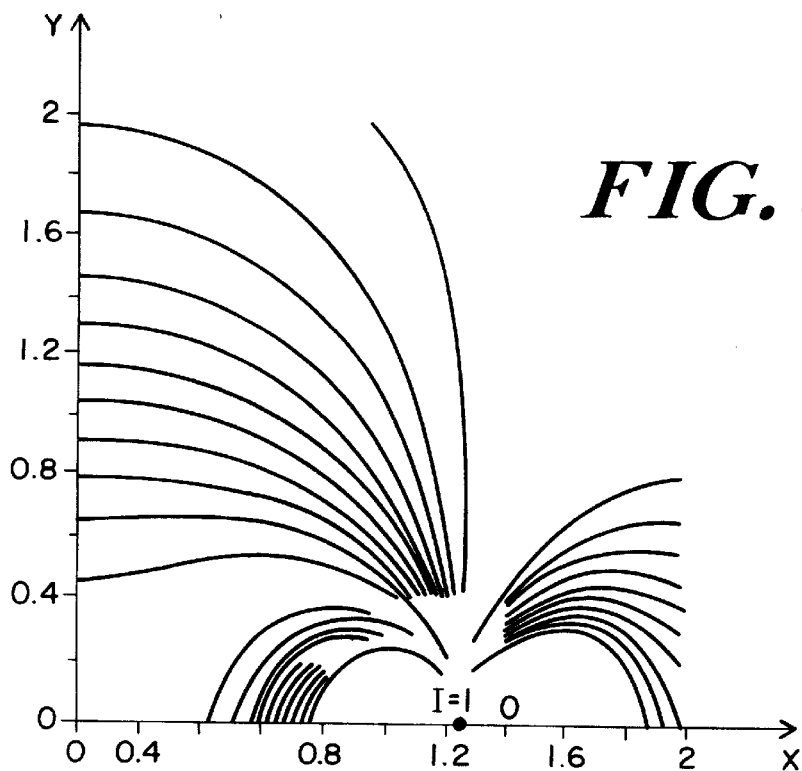
FIG. 5B is a plot of the field produced by the coil of FIG. 5.

A surface coil shown in FIG. 5 is wound in a fashion and geometry which departs from that of a Helmholtz coil where the field produced, FIG. 5A, by the former is considerably different from the latter. In FIG. 5, a surface coil is shown which has several turns 182, and 183 which enclose each other at least partially and which are arranged at different geometrical points. Each turn preferably comprises substantially a single conductor section or several conductor sections arranged in a group, the current flows being opposite to each other in mutually adjacent turns. The field produced by this coil is shown as FIG. 5A. In FIG. 5A, the field is shown in a plane perpendicular to the plane of the coil with the Y axis being the axis of the coils. The location coordinates are in arbitrary units and the lines of constant field strength are given with the relative strength ratios entered along the respective curves. Such a coil produces a steep field gradient in strength and direction at depths from the surface which is useful to realized selectivity by polarization and energy mechanisms discussed in the Theoretical Section.

In a preferred method where fields are used to achieve selectivity, treatment is carried out so that the propagation direction of the gamma ray is along the steepest part of the field gradient with regard to strength and/or direction such that no volume containing nonselected tissue along the ray path satisfies the resonance conditions for absorption of the gamma rays administered to the selected tissue.

In addition, the apparatus possess a means to selectively create absorption side bands of the Mossbauer absorber nuclei of the selected tissue. Absorption side bands of Mossbauer absorber nuclei can be produced by producing ultrasonic motion of the nuclei along the direction of the incident resonant gamma rays. The shift in energy and the amplitudes of the sidebands can be controlled by controlling the ultrasonic driving frequency and the ultrasonic power, respectively, as described by J. Mishory and D. I. Bolef, *Mossbauer Effect Methodology,* Irwin J. Gruverman, Editor, Vol. 4, (1968), pp. 13–35, incorporated by reference.

Selectivity is achieved by administering a narrow ultrasonic beam which intersects the administered gamma ray beam at the selected tissue site. The narrow ultrasonic beam is collimated or focused.

The beam from an ultrasonic transducer is collimated to a depth of $D^2/\lambda$ where D is the transducer width and $\lambda$ is the wavelength of the ultrasonic wave. Thus, for producing a collimated ultrasonic beam to produce absorption side bands at a depth z, the transducer size is given by equation 4.

$$D_{op} \cong \sqrt{\lambda Z_{max}} \tag{4}$$

Focused beams are produced by the use of an acoustic lens or by dynamic focusing through electronically controlled transducer arrays. An acoustic lens is generally made of a plastic material which has an acoustic propagation velocity greater than that of water; thus, the refractive index is less than one, and the lens is positive converging. For such a lens of spherical curvature, the field amplitude is the Fourier transformer of the source distribution at a depth of Z=f, the focal length. This results in an effective lateral beam width at the focal plane of $\lambda f/D$. The velocity of sound in soft tissue is $1.5 \times 10^5$ cm/sec and the relationship between velocity, v, wavelength, $\lambda$, and frequency, W, is as follows:

$$V = \lambda W \tag{5}$$

Thus, the width at a focal length depth of 10 cm of a 10 MHz beam produced by a transducer of 1 cm width is 0.15 cm. The same beam width relationship is achieved by electronically controlling a transducer array. The output intensity and temporal relationship of acoustic emission of the array elements are controlled to produce interference effects to produce a focused ultrasonic beam. Rectangular annular ring, concentric ring, and Theta arrays to produced electronically focused ultrasonic beams in addition to acoustic lenses and collimated transducers to produce narrow directed ultrasonic beams are described in *Medical Imaging Systems,* Albert Macovsik, (1983), pp 173–223, incorporated by reference.

Treatment is performed by directing the ultrasonic beam at the selected tissue to excite a component of ultrasonic motion of the Mossbauer absorber nuclei in the direction of the beam of the administered gamma rays which intersects the ultrasonic beam in the selected tissue. The ultrasonic beam creates absorption side bands for Mossbauer nuclei in the selected tissue of energy shift equal to the ultrasonic driving frequency. To achieve selectivity the driving frequency is varied to shift the side bands to an energy which is nonresonant with the nonselected tissue through which the gamma rays of energy resonant with the side bands travel to the selected tissue site. And, the amplitude of the excited absorption side band of the Mossbauer absorber nuclei of the selected tissue is maximized by controlling the power of the ultrasonic beam.

In one embodiment, ultrasonic tuning of the gamma ray source 202 is shown in FIG. 7. A source 204 of ultrasonic energy energizes the gamma ray source 202 through an acoustic coupling media. Alternatively, or in combination, a beam 206 of acoustic energy is provided by a source 208 to cause the Mossbauer absorber atoms to absorb the gamma rays at a target area common to both the path 212 of the gamma rays and the beam 206 of acoustic energy.

Treatment can be controlled by a microprocessor which receives digitized input from peripheral sensors which follow patient movement and displacement; velocity and acceleration of the mass drive; shutter position; the magnetic field strength and gradients; the frequency and voltage amplitude of the source ultrasonic transducer; the adsorber side band producing ultrasonic beam's direction, frequency, and intensity; and Mossbauer fluorescence. Source activities of the order of $10^3$ ci are possible so that treatment can occur over microseconds. Thus, precise treatment can be effected by electronic control in the presence of patient movement which occurs over times many orders of magnitude greater than the processing times of high speed control systems.

ADDITIONAL APPLICATIONS

MIRAGE drugs and therapy have many diverse applications in addition to the treatment of cancer. For example, MIRAGE compounds can be used for imaging and for treatment of any disorder which involves the eradication of cells which are implicated in the disorder. Disorders of the latter type include arthritis, autoimmune disease, tissue transplantation rejection, atherosclerosis, and AIDS.

IMAGE SCANNING

Radionucleotides, which have short half lives, on the order of hours, and which are gamma-emitting isotopes, are used in scintiscans to gain diagnostic information based on the physiological properties of the pathological process. These properties include differential uptake, concentration, or excretion of the radionucleotide by normal versus diseased tissue. For example, hepatic scintiscans are performed with gamma-emitting isotopes that are extracted selectively by the liver, followed by external radiation scanning of the upper abdomen. There are basically three types of liver scans: the colloidal scan, which depends on uptake of labelled colloid by Kupffer cells, where $^{198}$Au colloidal gold or $^{99m}$Tc sulfur colloid is most commonly used; the HIDA or PIPIDA scans ($^{99m}$Tc-labelled N-substituted iminoacetic acids) in which the dye is taken up and excreted by hepatocytes, and the gallium scan, in which the radionuclide $^{67}$Ga is concentrated in neoplastic or inflammatory cells to a greater degree than in hepatocytes. Hence, a hepatoma or liver abscess will produce an area of reduced uptake or "hole" using colloid or HIDA or PIPIDA scans, but there will be an area of increased uptake or "hot spot" with a gallium scan. The gallium scan is also helpful in diagnosing neoplastic infiltration in the patient with cirrhosis, since the tumor will show increased uptake, while fibrous bands will show decreased uptake. Another major application of HIDA or PIPIDA liver scans is in the diagnosis of acute cholecystitis, where failure of the nuclide to enter the gall bladder is considered evidence of cystic duct or common bile duct obstruction. The normal physiology involved is the uptake of these compounds by the hepatocytes followed by excretion into the biliary canaliculi and concentration in the gall bladder.

All Mossbauer isotopes are gamma emitters following absorption of the same energy gamma photon, and most are stable isotopes; therefore, they can be used in scintiscans. MIRAGE imaging compounds are described in the Macromolecular MIRAGE Pharmaceutical Section. As in the case of radionuclides, information can be gained based on differential uptake, excretion, or concentration as a consequence of the physiology of the pathological process. But, Mossbauer scintiscans also provide the ability to diagnose disease processes and to selectively image different tissues based on the phenomenon of the differential resonance frequency of the absorber isotope in different tissue environments via mechanisms discussed under selectivity in the Theoretical Section. Exciting the absorber isotope or isotopes by causing a selected energy emission from the source along one axis and simultaneously scanning with conventional Scintiscan instrumentation along an axis different from the former axis produces a Mossbauer Isotopic Resonance Absorption of Gamma Emission (MIRAGE) scintiscan. Due to attenuation of the exciting beam as a function of distance along the source axis, a correction algorithm has to be used to process the data to produce an image of the actual distribution of the Mossbauer isotope or isotopes in the tissue.

ARTHRITIS, AUTOIMMUNE, AND TRANSPLANTATION REJECTION DISEASE

A successful treatment for rheumatoid arthritis is the induction of necrosis of synovial cells of afflicted joints. For example, intra-articular radioactive synovectomy using the radionucleotide $^{165}$Dy coupled with the massive inert carrier, ferric hydroxide macroaggregate, has been shown by Sledge, et. al. (Sledge, Clement, B., Clinical Orthopedics and Related Research, No. 182, January–February 1984, pp. 37–40, incorporated by reference) to be an effective means of reducing inflamation, effusion and pain in patients with rheumatoid arthritis.

MIRAGE therapy provides selective cellular necrosis and intra-articular MIRAGE synovectomy can be substituted for intra-articular radioactive synovectomy to give the same therapeutic effect, and by substituting stable Mossbauer absorber isotopes for radioactive $^{165}$Dy in the synovectomy treatment, systemic radiation exposure from leakage is avoided.

Ferric hydroxide macroaggregate is massive in a recoil sense and it an other massive inert carriers of $10^8$ daltons or greater which were described previously would be effective in permitting the Mossbauer effect to occur. MIRAGE therapy is performed in this case with the previously mentioned massive inert carrier molecules containing stable Mossbauer atoms such as $^{161}$Dy, $^{163}$Dy, $^{57}$Fe and $^{119}$Sn in metallic, inorganic or organic form which are administered by intra-articular injection, and resonant Mossbauer radiation is administered to the joints.

Other diseases which can be cured by inducing necrosis of specific cell lines include autoimmune diseases and transplantation rejection disease which includes graft versus host and host versus graft. The cellular mediators for both of these diseases are lymphocytes. The responsible cell lines can be eradicated by synthesizing hybrid pharmaceuticals consisting of a protein and a MIRAGE pharmaceutical where the MIRAGE pharmaceutical includes one of those formed by derivatizing a DNA binding molecule of Table 6 with a Mossbauer absorber atom of Table 7 as described in the General Synthetic Pathways and Exemplary Materials Sections, and the protein includes a monoclonal antibody, the protein and MIRAGE pharmaceutical are attached by a covalent bond such as a disulfide, amide, ester, ether, amine, or carbon-carbon bond which is formed by using existing functional groups or by placing functional groups on the protein and MIRAGE pharmaceutical such as carboxyl, amino, sulfide, halogen, or carbonyl and condensing the two entities together by methods generally known to one skilled in the art. The protein binds to surface of the target cell in a highly specific manner. A monoclonal antibody to an antigen on the cell surface or a hormone which binds to a receptor on the cell surface could serve as the protein delivery molecule. The binding protein and the attached drug are internalized together and the protein is degraded releasing the MIRAGE drug which binds to a cellular target such as the cells' DNA. The tissue is irradiated at the resonant frequency of the pharmaceutical molecule bound to the cellular target. The subsequently released Auger electrons causes irreversible damage to the cell which is eliminated where the elimination serves a therapeutic function.

MIRAGE DRUG FOR ATHEROSCLEROTIC OCCLUDED ARTERIES

MIRAGE therapy can be used to eliminate the cells responsible for atheromas and involved in atherosclerosis.

The occlusion of arteries is the end result of the atherosclerotic process which involves the following stages 1) repeated injury which denudes the vessel of endothelium, 2) deposition of platelets, fibrin and lipids, 3) inward migration of smooth muscle cells and fibroblasts and 4) recanalization. The cycle repeats until vessel occlusion occurs. Recanalization at this point or lumen enlargement at a stage preceding occlusion requires removal of smooth muscle and fibroblast cells without damage to those cells of the same type which make up the vessel wall. This is possible, however, with MIRAGE drugs which can kill cells which have incorporated the drug by using levels of radiation which pose no threat to health. Selectivity in this case is based on selective uptake which is possible based on the fact that the smooth muscle cells and fibroblasts which must be removed interface the blood directly. A protein MIRAGE drug conjugate molecule which does not cross endothelium and binds to the surface of the smooth muscle and fibroblasts and not endothelial cells represents a selective drug because binding can only occur with those cells which interface blood directly. Specific binding proteins include monoclonal antibodies to Platelet Derived Growth Factor (PDGF) receptor. Binding is followed by internalization, degradation, and release of the drug which binds to a susceptible biological target such as DNA. Irradiation at the resonant Mossbauer absorption energy [frequency] of the bound drug then eliminates the occluding cells so that the vessel becomes patent.

MIRAGE AIDS DRUG

MIRAGE therapy can be made selective for the disease AIDS where infected T cells are eradicated as a therapeutic function.

Acquired immune deficiency syndrome (AIDS) has spread exponentially and is predicted to reach epidemic proportions. A conservative estimate of U.S. virus antibody positive individuals is $10^6$, and the U.S. death rate in the near future based on this figure is 54,000 deaths per year which compares with 30,000 deaths per year due to breast cancer. AIDS is a fatal disease with no specific treatment, and development of a vaccine presents a tremendous challenge for which there is no hope for success earlier than 1990. Furthermore, the development of experimental drugs for the treatment of AIDS has so far proceeded via a strategy comparable to that utilized to develop antiviral drugs for viruses such as Herpes. HIV, the causative agent of AIDS, behaves very differently from other human pathogenic viruses because it destroys the T cell segment of the immune system which normally is responsible for controlling the elimination of a viral challenge. In fact, HIV is unique as a retrovirus in that it is cytopathic. Also, the biology of the virus is such that it can elude the immune system during a latent phase and then activate to produce virus at a tremendous rate before the host cell dies. This life cycle is a consequence of a transactivating factor, tat III, and trs, a gene product unique to HIV. The later protein controls the differential splicing of the viral message at different points in the virus life cycle. The complex in vivo behavior of HIV, which is characterized by persistent infection in the human host, may depend on the regulatory control of viral RNA splicing and translation. With a capacity to express viral regulatory, but not structural proteins, HIV infected cells may avoid the host immune response but would be able to activate virion production quickly following additional viral or cellular signals. Indeed, one manifestation of latency seen in visna virus infection is characterized by viral RNA synthesis without subsequent virion assembly. Likewise, HIV infected but nonexpressing human T cells can be viably maintained in long term culture, only to die when virus production is induced by immunologic stimulation.

The cytopathic effect of HIV directly correlates with the amount of viral envelop protein synthesized in infected cells. Thus, efficient HIV production may require rapid viral protein synthesis and assembly in the race between virion release and cell death. The presence of large amounts of tat III at the time of a trs-mediated splicing pattern switch to the synthesis of genomic and envelop mRNAs may thus facilitate production of a very cytopathic virus. Antimetabolites and molecules which inhibit HIV enzymes can only slow the relentless progress of this disease which destroys the host's immune system by a T cell cytopathic life cycle. The viral message exists in the host DNA and is replicated with the host DNA. An infected cell represents a silent harbinger poised to release infectious viral particles following the proper cellular or viral signals. A reasonable approach to curing AIDS in an infected individual is to destroy all such cells before the host's immune system is inundated with virus and irreversibly compromised. MIRAGE drugs represent agents which can selectively discriminate and destroy HIV infected cells in the latent stage.

MIRAGE drug selectivity can derive from selective uptake, a unique isomer shift, hyperfine splitting, and/or activation to permit binding to a large target which permits the Mossbauer phenomenon to occur. The enzymes involved in the life cycle of the virus can be used to activate a drug only in cells harboring the virus. Activation results in the selective deposition of Mossbauer radiant energy in the HIV infected cells using one of the mentioned mechanisms. Based on the present knowledge of the biochemistry of HIV, the exploitation of the activation of a unique chemical shift is feasible. The mechanism is is explained in the Theoretical Section.

Activation which involves changes in the chemical environment at the Mossbauer atom of an intercalating MIRAGE drug can be exploited as a method to selectively eliminate HIV infected cells in the latent stage. Tat III is the only protein known to be expressed during HIV latency. This protein is both a cytoplasmic and a nuclear protein of about 14 kd. MIRAGE drugs to cure AIDS are those that intercalate and also bind tat III. The later interaction must change the electronic environment at the Mossbauer nucleus to create a unique chemical shift. Intravenous and intrathecal administration of such a drug followed by systemic irradiation at the frequency of the created isomer shift will selectively kill latent infected cells and interrupt the infectious process.

THEORETICAL SECTION PRINCIPLES OF RADIATION THERAPY

Ionizing radiation was found shortly after its discovery to be capable of reducing the growth of human tumors. Unfortunately the limitations of this modality were discovered as patients developed catastrophic late complications. The radiotherapist must perform treatment such that the balance of these opposing ends is in favor of tumor ablation. The total story of the cellular mechanisms involved remains elusive; however, many of the principles involved can be appreciated from survival curves and a basic understanding of the effect of radiation on cells and the cellular response to damage.

Radiation therapy involves particle and electromagnetic radiation which causes damage to both normal and cancer tissue. The goal is to ablate the tumor while preserving normal tissue. The principles involved are manifested in cell survival curves (See FIGS. 8 and 9). Cells exposed to radiation reach a treatment threshold and then are killed exponentially, the survival number versus radiation dose is an exponential curve where a constant fraction of the cells are killed per treatment. All tumors can be controlled as the dose goes to infinity; however, it is the limitation of tolerance of normal tissue not the ability to control the tumor which is the guide to treatment. Thus, it can be appreciated that a significant factor involved in a cure is the first order rate constant, α, and the initial burden $N_o$ which appear in the first order rate equation below:

$$N=N_{o}\,\epsilon^{-\alpha Dose} \quad (6)$$

Critical is a reduction of the tumor burden, N, to a level which is no longer overwhelming to the body's natural defenses. Treatment with radiation can lead to a cure even though this is a local modality which has no effect on distant micrometastases despite the shedding of malignant cells by tumors which are below the mass sufficient for diagnosis. Current data supports three explanations for this inconsistency.

(1) Only a fraction of the clonogenic cells in the primary retain their capacity to create metastases and nonclonogenic cells may not continue to grow and invade at a distant site.

(2) There is evidence that the host has the ability to kill a limited number of viable metastatic cells.

(3) The tumor mass influences its own metastatic potential. Radiation therapy by diminishing the mass reduces the source of clonogenic metastases and increases the host's ability to deal with residual micrometastases by eliminating the tumor's adverse effect on the host immune system.

The ideal in radiation therapy of malignant disease is achieved when the tumor is completely eradicated and the surrounding normal tissue of the treatment volume is structurally and functionally intact. The important factor in the successful treatment is the difference in the radiosensitivity of neoplastic and normal cells which is the slope, α, of equation 6. The difference depends on the differential susceptibility to DNA damage, differential repair capabilities, and differential tolerance to unrepaired damage as well as the ability of normal organs to continue to function well if they are only segmentally damaged. In general, if surrounding tissue can tolerate twice the radiation dose of a given tumor, then the tumor is radiosensitive. Alternately, a tumor which extensively involves both lungs, and may be cured with a dose of 3000 rads, cannot be treated effectively with radiation therapy because of the greater radiosensitivity of the surrounding lung tissue.

All tumors can be eradicated by treatment with sufficient radiation. But, damage to normal tissue is dose limiting due to the acute and late effects of radiation therapy. Acute effects include esophagitis, pneumonitis, and diarrhea. They occur shortly after treatment and limit the size of any given dose. Acute effects are usually reversible and independent of the treatment history. However, tissue has memory in that there is a threshold to the total dose accumulated over the patient's history above which unacceptable late effects occur. Late effects are total dose limiting in radiation. They often progress with time and are usually irreversible. These include fibrosis, necrosis, fistula formation, non-healing ulcerations, and damage to specific organs such as spinal cord transection or blindness. Normal tissues and organs differ in radiosensitivity. The risk of complications increases with dose, and if delivered by megavolt sources, in the usual fractions, occurs when doses exceed the following: both lungs 1500 rads; both kidneys 2400 rads; liver 1500 rads; heart 3500 rads; spinal cord 4000 rads; intestine 5500 rads; brain 6000 rads; bone 7500 rads. While the mechanisms of toxicity are not clear, they do not appear to depend primarily on the rapid proliferation of cell renewal tissue. Clinically they appear to depend much more on the total dose and the size of the dose fraction. Acute reactions may be misleading as a guide to long term effects. There are a number of examples in radiation therapy where the total dose has been increased, the size of the dose fraction increased or kept the same while the interfraction period protracted to reduce acute effects. Such maneuvers have resulted in unacceptable late complications.

There are two hypotheses for the mechanism of late radiation effects. One theory attributes late effects to the destruction of connective tissue stroma. The pathogenesis of liver cirrhosis is evidence that fibrosis can lead to organ destruction despite the renewal potential of the cells of the organ. A variation on this hypothesis is that the vasculo-connective issue is destroyed due to endothelial cell injury which ultimately produces the late effects. An alternate hypothesis suggests that both the acute and late effects of radiation are due to depletion of the stem cell pool. Acute effects depend on the balance between cell killing and compensatory replication of both the stem and proliferative compartments. The development of late effects requires that the stem cells have only a limited proliferative capacity. Compensation for extensive or repeated cell death may exhaust this capacity resulting in eventual organ failure. This phenomenon can be demonstrated for mouse hematopoietic lines. Stem cells can be passed a finite number of times into irradiated mice until they lose the ability to reconstitute the recipient's marrow.

Successful radiation therapy can be understood from the dynamics of cellular responses to radiation. From the dynamic point of view, the basic difference between a normal renewal tissue of the body and a tumor is that in normal tissue there is an effective balance between cell production and cell loss; whereas, in tumors, cell proliferation exceeds cell loss. The normal renewal tissue can be considered a hierarchy of three types of cells: Stem cells→Maturing cells Functioning cells.

The cell cycle of cancer cells are in general shorter than those of normal tissue. It is found in general that irradiation causes an elongation of the generation cycle of tumor cells while a corresponding shortening of the cell cycle of normal cells is the norm as the stem cells reconstitute the tissue. Dividing cells are more susceptible as they possess more DNA and repair is more difficult. Radiosensitivity of normal tissue may be partially explained based on the magnitude of the regenerative response, potentially lethal repair may not occur in rapidly dividing cells as occurs in regenerating tissue. Also, experimental data indicate that potentially lethal damage is repaired, and the fraction of cells surviving a given dose of X-ray is enhanced if post radiation conditions are suboptimal for growth. Both of these mechanisms favor tumor cells over normal cells.

Thus, a major factor leading to a cure and which underlies relative radiosensitivity is DNA repair capabilities. This phenomenon of repair which is evidenced in the magnitude of the survival curve shoulder accounts largely for the sparing effect on normal tissue of the multi-fraction dose regimens that are so commonly employed in clinical radiotherapy.

Figure 8:
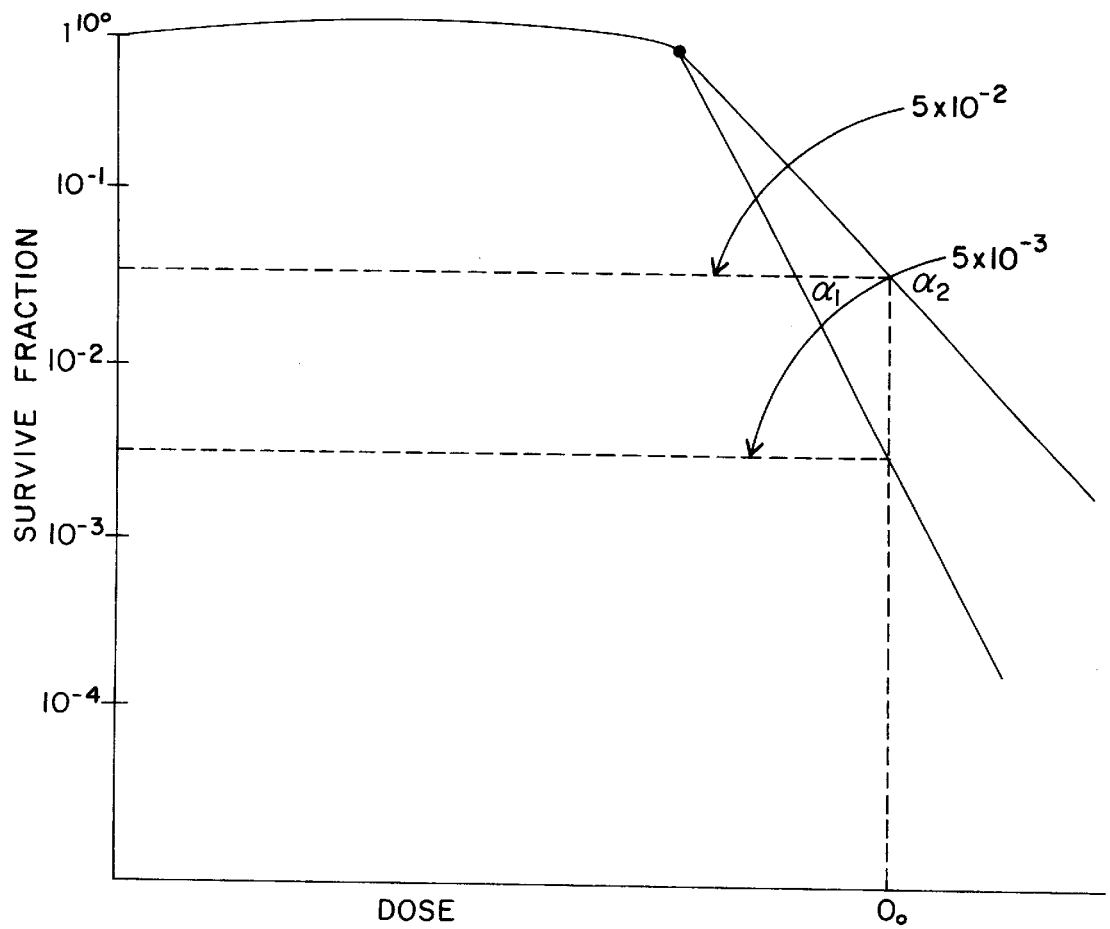
FIGS. 8 and 9 are graphical plots of data related to radiation therapy.
Figure 9:
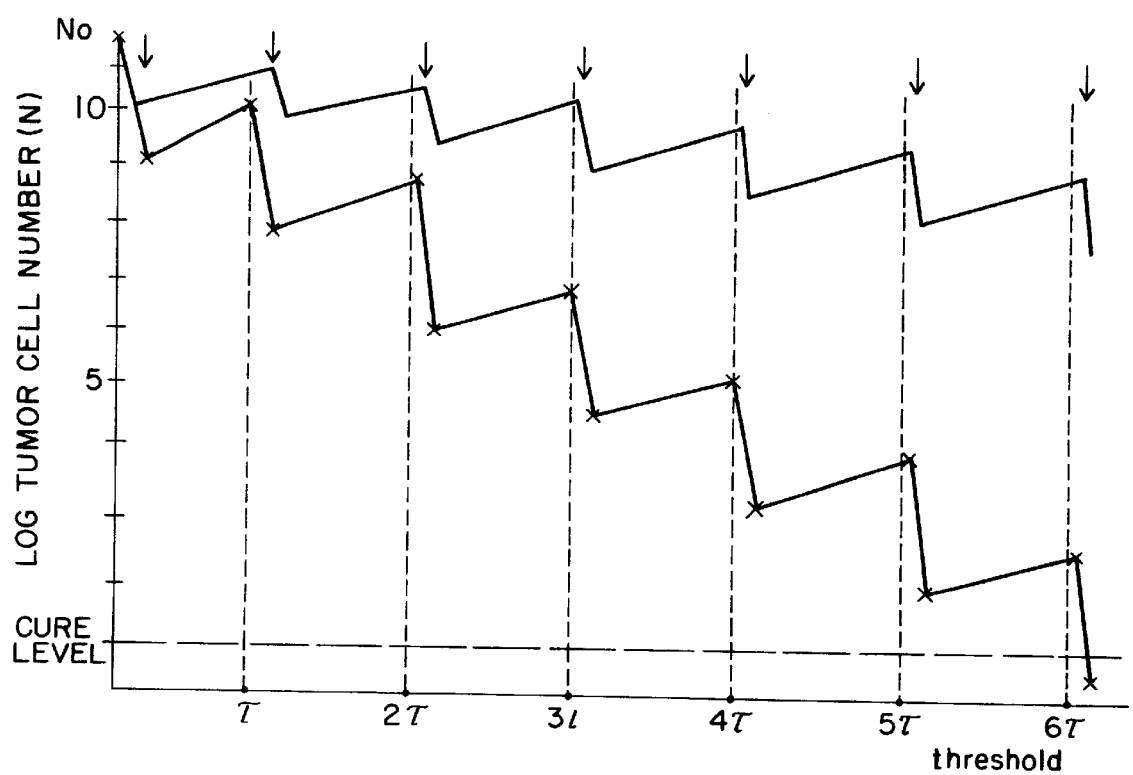

As with normal tissue, different tumors have a range of radiosensitivity some being responsive to a few hundred rads, and others incurable with as much as 10,000 rads, and this variation can even exist within a specific tumor type. Furthermore, radioresistance is selected for in the tumor population as normal tissue regenerative capability declines. Thus, it can be appreciated, from survival curves, as exemplified in FIGS. 8 and 9, that necessary but not sufficient conditions for a cure via radiation therapy are that the first order kinetics of cell kill must be such that enough cancer cells are killed and the tumor does not return to its original mass in the time interval necessary for normal tissue to regenerate. And, the tumor volume is reduced to a level which can be eliminated by the host's defenses before an accumulated dose is reached which will ultimately produce unacceptable late effects.

PHYSICS OF RADIATION THERAPY

Ionizing radiation exerts its effects on atoms primarily as a function of the number of electrons. Biological molecules are predominantly composed of atoms of less than atomic wt, 15, and there is not a large difference in the magnitude of ionizations of one element versus another. At a given dose, ionizing radiation reacts with a fraction of any given molecule in its path. Therefore, a fraction of proteins, and a fraction of DNA, etc, is damaged. Therefore, even though it may be argued that the number of ionizations in a cell may outnumber that of a critical species present at low concentrations, only a fraction of that species is damaged and the cell can survive if it can continue to produce proteins, replicate, and divide with extreme fidelity. Thus, it is evident from a theoretical point of view, and it is confirmed experimentally that the critical element for survival for a cell is to protect or reconstitute its genetic message. DNA has the ability to rapidly repair most damage but lacks the ability to repair double strand breaks which is the lethal event in radiation therapy.

The radiation effects on particular molecules such as DNA, are ascribed to two processes, direct and indirect action. By direct action is meant the effects of energy directly in the target molecule. By indirect action is meant effects of reactive species formed in the surroundings that diffuse to the target and react with it.

For DNA in dilute aqueous solution, the indirect effects of irradiation are caused by the products formed by the action of ionizing radiations on water which are the OH radical, the hydrated electron, $e^-$ aq, the H atom, $H_2O_2$, and $H_2$. The major effective species in oxygenated solution is the OH radical. This reacts chiefly with organic molecules either by adding to a double bond, or by extracting an H atom from a $C^-H$ bond to form $H_2O$ and a carbon radical. The OH radical reacts essentially at a diffusion controlled rate with DNA and DNA components.

Estimates of the extent of reaction indicates that of the 2.7 OH radicals produced per 100 ev of energy absorbed, at least 0.6 (20%) react with sugars to produce single strand breaks and less than 2.1 (80%) with bases to produce modified bases. Cells irradiated in the presence of radical scavengers have fewer single strand breaks. There are many measurements of single strand breaks in DNA from irradiated mammalian cells. Most fall in the range of 1 to $10 \times 10^{-12}$ strand breaks in alkali per rad per dalton. The direct and indirect effects being about equal. And, an effective diffusion radius for the OH radical has been calculated to be approximately 2.3 nm.

DNA double strand breaks could be produced by coincidence between two independent events, by attack on two sugars by two radicals formed in a single cluster by perhaps a high LET particle or as a consequence of ionization of an inner shell electron in the DNA molecule where it is estimated that perhaps 5% of the ionizations in irradiated DNA may be associated with inner shell excitations. Experimentally about one double strand break, a lethal event, is observed per 20–40 single strand breaks.

DNA LABELING AND MECHANISM OF MIRAGE THERAPY

The mechanism and biological effect of direct damage to DNA by particle or electromagnetic radiation can be assessed by labeling the constituent nucleotides with beta emitters and alpha emitters, respectively. The effects that arise from the decay of beta emitters incorporated into the genetic material are single and double strand breaks, base alterations, and inter-strand cross linking. Single strand breaks can be efficiently repaired by living cells, whereas double strand breaks are relatively inefficiently repaired and are potentially lethal. In labeling experiments, the predominant mechanism responsible for lethality appears to be double strand breaks caused by internal radiolysis by primary or secondary generated particles. For tritium labeled DNA the probability of producing a double strand break per decay is less than one, and the plot of cell survival versus decay demonstrates a shoulder. Contrarily, $^{125}I$ produces between 2 and 12 double strand breaks per decay event by a mechanism called an Auger cascade, described below. This involves ejection of valence electrons by an emitted gamma ray. The plot of cell survival vs. number of decays demonstrates no shoulder indicative of a one hit one target mechanism. Labeling experiments which label molecules other than nucleotides demonstrate that lethality can be explained by the proximity of the primary or secondary particle radiation to the cell nucleus which is consistent with the lethal event being nuclear damage. Lethality also involves probability as demonstrated by the inverse relationship between the number of decay events needed to kill a given cell type by a radioisotope and the number of radiated electrons which it produces. For example, Bradley, et al has demonstrated that $^{125}$I is sixteen times as lethal as tritium and Charleton and Booz calculated the electron spectrum following decay of $^{125}$I to determine in the mean 21 electrons of high linear energy transfer are emitted per decay via Auger cascade of electrons.

An Auger cascade is produced as part of a radioactive decay pathway involving internal conversion. Internal conversion results in ejection of inner shell electrons called conversion electrons. Outer shell electrons can fill the vacancies and release energy. The difference between the ionization energy of the inner shell electron and that of the outer shell can be released by transmission to another electron which is then ejected as an Auger electron to produce a new vacancy. The process continues shell by shell, until the valance shell is reached and thus leads to multiple ionizations of the atom. Such a valency cascade, for elements of low or medium atomic number, the Auger electrons have energies up to a few KeV with a relatively high linear energy transfer of 1 to 10 ev/nm. Since such electrons dissipate their energy in materials of unit density within a distance of the order of 10 to 100 nm they may efficiently damage molecules in the nearness of the decay event.

With regard to radiolabeling DNA, one decay event of a radioactive atom such as $^{125}$I of internal conversion, followed by an Auger cascade which cause radiolysis and double strand breakage is lethal to a cell. Radiation therapy is far less efficient requiring approximately $10^5$ photons absorption events per cell to produce the same lethal event. MIRAGE therapy accomplishes the same end point as these modalities without the use of radioactive atoms and with electromagnetic radiation doses one million times less than that of conventional radiation therapy. This is accomplished by utilizing phenomenon common to electromagnetic radiation therapy and radioactive atomic DNA labeling. MIRAGE therapy entails using Mossbauer atomic labeled pharmaceuticals which bind to the genetic material of the target cell and resonantly absorb gamma radiation to excite nuclear transitions. Nuclear excitation produces a radioactive atom from a stable atom, and the consequences are the same as for the case of $^{125}$I labeled DNA. Furthermore, this single event will kill the target cell which is in contrast to conventional radiation therapy where multiple improbable events must occur simultaneously to produce a double strand break. $10^5$ photons by conventional therapy versus one for MIRAGE therapy are necessary to eradicate the target cell. Also, much less photon flux is needed for MIRAGE therapy. The absorption cross-section for water the primary target of conventional radiation therapy is approximately $10^{-25}$ cm$^2$, whereas the resonant cross-section for Mossbauer absorption is $10^{-17}$ cm$^2$ which represents an eight order of magnitude improvement. This increased efficiency permits cell kill with radiation doses of one millionth that of conventional therapy.

PHYSICS AND CHEMISTRY OF MIRAGE THERAPY WITH 12/29/W AS AN EXAMPLE.

The primary decay of the majority of radioactive nuclides produces a daughter nucleus which is in a highly excited state. The latter then de-excites by emitting a series of gamma ray photons until it reaches a stable ground state. The Mossbauer effect occurs when the gamma ray emitted during a transition to a nuclear state is used to excite a second stable nucleus of the same isotope; thus, giving rise to resonant nuclear absorption. This is an extremely monochromatic event. The degree of monochromaticity can easily be shown from the Heisenberg uncertainty principle. The ground state of the nucleus has an infinite lifetime, and, therefore, there is no uncertainty in its energy. The uncertainty in the lifetime of the excited state is given by its mean life, τ, and the uncertainty in its energy is given by the width of the statistical energy distribution at half height, Γ. They are related by $$\Gamma \tau \geq \zeta \quad (7)$$

is related to the more familiar half-life of the state by $\tau = \ln 2 \times t_{1/2}$. If Γ is given in electron volts and $t_{1/2}$ is in seconds, then $$\Gamma = 4.562 \times 10^{-10}/t_{1/2} \quad (8)$$

For a typical nuclear excited-state half-life of $t_{1/2}=10^{-7}$ seconds, Γ=4.562×10$^{-9}$eV. If the energy of the excited state is 45.62 KeV, the emitted gamma ray will have an intrinsic resolution of one part in $10^{13}$. For comparison, the maximum resolution obtained in atomic line spectra is only about one in $10^8$. In fact, the line width is so narrow that its energy can be Doppler shifted by driving the source at moderate velocities or side bands in the emission energy can be created by driving a stationary source at ultrasonic frequencies where the energy of the side bands is continuously tunable by varying the ultrasonic driving frequency. It is the capability of shifting the energy of the source to cause resonant absorption in an absorber atom incorporated as part of a pharmaceutical molecule that permits the use of this phenomenon to selectively treat disease such as cancer.

The Mossbauer effect is degraded by recoil energy of the emitted and absorbed photon. This limitation can be circumvented by binding the Mossbauer source and absorber atoms into a massive lattice or molecular structure. The recoil energy is given as follows:

$$E_R = \frac{E_r^2}{2Mc^2} \quad (9)$$

This equation indicates that as the mass of the structure into which the Mossbauer atom is incorporated goes to infinity the recoil energy goes to zero. To accomplish this the source atoms are incorporated into a lattice or metal and the absorber is incorporated into a pharmaceutical which binds to a massive molecule or is incorporated into a biological lattice. Examples include DNA and bone matrix, respectively. For the former case, the Mossbauer atom is bound to a pharmaceutical by covalent, chelation, or coordinate bonds and the pharmaceutical molecule binds to DNA by hydrogen or covalent bonding, electrostatic interactions, or intercalation.

Structures which bind to DNA to form extremely stable complexes with duplex DNA by hydrogen bonding and electrostatic interactions and which could be used as part of a MIRAGE drug include netropsin, distamycin A, and anthramycin. And intercalating structures which could be used to produce a MIRAGE drug include ellipticinium, quinacrine, actinomycin, mithramycin, ethinium, adriamycin, acridine orange, nogalamycin, propidium, anthracyclines, psoralen, duanarubicin, bithiazole, olivomycin, chromomycin A$_3$, acridine, chloroquine, quinine, 8 amino-quinolines, quinacrine, proflavin, bleomycins, phleomycins, mefloquine, mitoxantrone, and others which represent modification of the mentioned basic molecular structures.

See Table 6 for the structure of DNA binding molecules and see FIG. 10 for a diagram of MIRAGE drug 12/29/W and its mechanism of intercalation.

Degradation of the Mossbauer effect via recoil of the entire atom can be prevented by bonding it to a massive object; however, nuclear recoil energies are of the order of magnitude of lattice-vibration phonon energies and the Mossbauer effect can be degraded if the recoil energy excites one of the quantized vibrational levels. The probability that one emission or absorption event will occur without vibrational degradation is given by the parameter f which is known as the recoilless or recoil-free fraction. To increase the relative strength of the recoilless resonant process, it is important that f be as large as possible. The recoilless fraction f can be related to the vibrational properties of the crystal lattice by $$f = \left(-\frac{E_r^2 \langle x^2 \rangle}{(\hbar c)^2}\right) \qquad (10)$$

where $\langle x^2 \rangle$ is the mean-square vibrational amplitude of the nucleus in the direction of the gamma ray. From the form of the exponential, f will only be large for a tightly bound atom with a small mean-square displacement and for a small value of the gamma ray energy, $E_\gamma$. F can be increased for the source by cryostatically cooling it, and f can be increased for the absorber atom which is part of a pharmaceutical by increasing the bond strength of the atom with the remainder of the pharmaceutical molecule.

As described previously, Auger cascades in DNA binding pharmaceuticals cause DNA radiolysis and concomitant death of the cells in the target tissue. The equation which relates the number of internal conversion events with concomitant Auger cascade to nuclear parameters is given as follows:

$$B = \theta_o f n \phi \qquad (11)$$

where B is the number of internal conversion events, $\theta_o$ is the Auger cross-section, f is the recoilless fraction, n is the number of Mossbauer atoms, and $\phi$ is the photon flux. $\theta_o$ is entirely determined by nuclear parameters and is given by the following equation:

$$\sigma_o = 2\pi\left(\frac{\hbar c}{E_r}\right)^2 \frac{2Ie+1}{2Ig+1} \frac{\alpha}{1+\alpha} \qquad (12)$$

$$\sigma(E) = \sigma_o \frac{\left(\frac{\Gamma}{2}\right)^2}{(E-E_r)^2 + \left(\frac{\Gamma}{2}\right)^2} \qquad (13)$$

where equation 12 gives the maximum cross-section, $\theta_o$, at $E=E_o$, and equation 13 is the cross-section for resonant absorption. Ie and Ig are the nuclear spin quantum numbers of the excited and ground states, $\Gamma$ is the line width, and $\alpha$ is the internal conversion coefficient which is the ratio of the number of conversion electrons to the number of gamma ray photons emitted. To generate an effective MIRAGE drug, a Mossbauer atom with a large Auger cross-section which emits multiple Auger electrons of high linear energy transfer of the range 1–10 ev/nm is used. Examples of isotopes with large Auger cross-sections are given in Table 8 where the value for $^{57}$Fe is given as $2.2 \times 10^{-17}$ cm$^2$.

The number of targets, n, is dependent on the binding constant of the drug with DNA. The bithiazale group of Bleomycin has a Kd of the $10^6$ which results in one Bleomycin molecule bound per eight nucleotides. This represents at least $10^9$ target atoms per cell. Intercalating drugs such as biacridines have Kd's of the order of $10^{11}$; thus n can be made even larger. And, drugs which use different modes of binding can be used in combination. For example, the DNA molecule can become saturated with intercalated drugs but retain the ability to bind a drug which binds by a mode different than intercalation. An example is Netropsin which binds externally to the DNA molecule by electrostatic interactions. N can be increased by using a combination of drugs such as acridine and Netropsin analogues where binding is by intercalation and electrostatic interactions, respectively.

TABLE 8

Representative Mossbauer Isotopes with Parameters Favorable for Cancer Therapy

| Isotope | Half Life of Ground State (yr)/ Mode of Decay | Isotope Abundance (%) | Gamma Ray Energy (keV) | Half Life of Excited State (NS) | /Auger (Cross-Section) ($10^{-20}$ cm$^2$) | Mossbauer Line Width (mm/sec) | Recoil Energy ($10^{-3}$ ev) | Recoil Free Fraction of Crystal Absorber T = 300° $\sigma_d$ = 200 (%) |
|---|---|---|---|---|---|---|---|---|
| Potassium 40 | $1.28 \times 10^9$B | .012 | 29.5 | 4.25 | 6.6/196 | 2.177 | 11.7 | .6 |
| Iron 57 | | 2.14 | 14.4 | 97.8 | 8.21/2218 | .194 | 1.956 | 44 |
| Tin 119 | | 8.58 | 23.87 | 17.75 | 5.12/716 | .6456 | 2.57 | 33 |
| Antimony 121 | | 57.25 | 37.15 | 3.5 | 11.1/217 | 2.104 | 6.12 | 7 |
| Tellurium 125 | | 6.99 | 35.46 | 1.48 | 13.5/361 | 5.209 | 5.39 | 10 |
| Iodine 127 | | 100. | 57.6 | 1.91 | 3.78/77.5 | 2.486 | 14.0229 | .2 |
| Iodine 129 | $1.7 \times 10^7$B | 0. | 27.77 | 16.80 | 5.1/199 | .586 | 3.2089 | 25 |
| Xenon | | 26.44 | 39.58 | 1.01 | 12.3/288 | 6.84 | 6.5187 | 6 |
| Samarium 149 | $4 \times 10^{14}\alpha$ | 13.83 | 22.4940 | 7.12 | 50./372 | 1.708 | 1.8 | 45 |
| Europium 151 | | 47.82 | 21.53 | 9.7 | 30./658 | 1.3 | 1.648 | 46 |
| Gadolinium 155 | | 14.73 | 60.01 | .134 | 8./90.66 | 34.02 | 12.47 | .5 |
| Gadolinium 157 | | 15.68 | 54.54 | .187 | 11.87/114 | 26.82 | 10.17 | 1.2 |
| Gadolinium 157 | | 15.68 | 64.0 | 460. | .7/37 | .009 | 14.004 | .5 |
| Terbium 159 | | 100.0 | 57.955 | .10 | 9.36/98.5 | 44.9 | 11.355 | .8 |
| Dysprosium 161 | | 18.880 | 25.655 | 28.2 | 2.9/275 | .378 | 2.1944 | 38 |
| Dysprosium 161 | | 18.880 | 43.83 | .78 | 4.32/137 | 3.00 | 6.4040 | 5 |

TABLE 8-continued

Representative Mossbauer Isotopes with Parameters Favorable for Cancer Therapy

| Isotope | Half Life of Ground State (yr)/ Mode of Decay | Isotope Abundance (%) | Gamma Ray Energy (keV) | Half Life of Excited State (NS) | /Auger (Cross-Section) ($10^{-20}$ cm$^2$) | Mossbauer Line Width (mm/sec) | Recoil Energy ($10^{-3}$ ev) | Recoil Free Fraction of Crystal Absorber T = 300° $\sigma_d$ = 200 (%) |
|---|---|---|---|---|---|---|---|---|
| Dysprosium 163 | | | 26. | | | | | 39 |
| Ytterbium 171 | | 14.31 | 66.72 | .87 | 11.2/100.6 | 4.7127 | 13.97 | .2 |
| Tungsten 183 | | 14.40 | 46.4837 | .184 | 40./220 | 31.98 | 6.3379 | 6.54 |
| Osmium 189 | | 16.1 | 36.22 | .500 | 80./92 | 15.105 | 3.7259 | 20.2 |
| Mercury 201 | | 13.22 | 32.19 | .200 | 60./117 | 42.49 | 2.7672 | 30.4 |
| Thorium 232 | $1.41 \times 10^{10} \alpha$ | 0. | 49.369 | .345 | 300./507 | 16.06 | 5.639 | 9 |
| Uranium 238 | $4.5 \times 10^9 \alpha$ | 99.27 | 44.915 | .2250 | 660./602 | 27.069 | 4.5499 | 14.3 |
| Neptuniun 237 | $2.14 \times 10^8 \alpha$ | 0.00 | 59.5370 | 68.3 | 1.12/36 | .0672 | 8.0283 | 3.1 |

$\alpha$ = alpha
B = beta

MIRAGE drugs must be designed such that they have a high recoilless fraction which is a function of the vibrational energy of the bond linking the Mossbauer atom to the pharmaceutical. The energy of molecular vibrations has a range of 5–50 KJ; whereas lattice vibrational energies range between 0.5 to 5 KJ. As a comparison, the vibrational energy of Fe metal at room temperature is 1 KJ. To achieve a high recoilless fraction the vibrational energy should be an order of magnitude greater than the recoil energy which is 0.1 KJ for $^{57}$Fe. For example, the vibrational energy of Fe metal is an order of magnitude greater than the recoil energy, and f for $^{57}$Fe metal at room temperature is 0.7. F should be higher for $^{57}$Fe/Bleomycin because KD for the coordination of iron with Bleomycin is $10^9$ which gives a AG of approximately –50 KJ and a vibrational energy of approximately 5 KJ by thermodynamic calculations.

Since covalent bonding yields higher vibrational energies, the Mossbauer atom should be covalently bound to the intercalating function. Many of the Mossbauer isotopes form covalent bonds with organic molecules. Examples include Mossbauer isotopes of tin, antimony, tellurium, iodine, germanium, and mercury. Lanthanide Mossbauer isotopes such as gadolinium, dysprosium, samarium, and europium form chelation compounds with $K_D$'s of the order of $10^{23}$. Mossbauer isotopes can also be involved in organometallic bounding such as occurs between iron and cyclopentadiene and between osmium and cyclopentadiene in ferrocene and osmocene, respectively. Vibrational energies for these compounds is approximately one tenth the bonding energies which are of the order of 300 KJ/mole. Thus, the recoilless fraction for pharmaceuticals involving this bonding would be high. Examples of MIRAGE pharmaceuticals are given in the Exemplary Material Section.

Using the previously described nuclear and thermodynamic parameters, a calculation of the dose necessary to achieve therapeutic efficacy can be calculated for 12/29/w and compared to the actual experimental effect which appears in the Experimental Section. For $^{57}$Fe the Auger cross-section is 2.2×10$^{17}$ cm$^2$ where $\alpha$=10 and internal conversion occurs greater than 90% of the time. Greater than 10 conversion electrons and Auger electrons are emitted on average per transition as appeared in FIG. 11. The binding constant of Bleomycin to DNA is $10^6$ which corresponds to the number of targets, n, equal to $10^9$. The free energy of binding of iron to Bleomycin is 50 KJ which predicts a recoilless fraction, f, of approximately one. One nuclear excitation event followed by internal conversion produces a lethal hit. The necessary photon flux to effect this event is calculated using equation 11 as follows:

$$\frac{1}{(10^9)(1)(2.2 \times 10^{-17})} = \phi = \frac{4.5 \times 10^7 \text{ photons}}{\text{cm}^2}$$

The dose due to this photon flux is calculated as follows for the 14.4 KeV gamma ray of a $^{57}$Co source using the equation from FIG. 12 where 70% of the energy is absorbed in 1 cm:

$$\text{Dose} = (.7)\frac{(4.5 \times 10^7 \text{photons})}{(\text{cm}^2)} \frac{(14.4 \times 10^3 ev)}{(\text{photon})} \frac{(1.6 \times 10^{-19} J)}{(ev)} \frac{(10^7 \text{erg})}{(1J)} \times$$

$$\frac{\frac{k\text{rad}}{100\text{erg}}}{g}$$

$$= 7 \text{ m rad}$$

This can be compared with the m rad levels of Mossbauer radiation which were found to be effective in the experiments indicated in the Experimental Section.

ADDITIONAL PHARMACEUTICALS

Exploitation of the Mossbauer effect permits drugs which will eradicate target cells using levels of radiation which are comparable to background levels and well below levels that are necessary to cause acute or late effects of radiation therapy. Furthermore, MIRAGE therapy is a modality whereby the side effects of chemotherapy can be eliminated. MIRAGE drugs are designed such that they bind to targets such as DNA and the therapy is conducted in such a manner that the Mossbauer effect will be caused to occur in the space occupied by the target cells, but not to a significant extent in the nontarget cell locations by mechanisms to be described below. The binding can be nontoxic. Representative nontoxic structures are psoralens used for the treatment or psoriasis, quinacrine and acridine drugs used for parasitic diseases, quinoline drugs used for the treatment of malaria, thioxanthenone drugs used for the treatment of Schistosomiasis, and Tilorone, an antiviral drug, (see Table 6 for structures).

The parameters involved in fabricating a pharmaceutical using other Mossbauer isotopes are the same as those discussed for $^{57}$Fe. For example $^{119}$Sn, $^{121}$Sb, and $^{125}$Te can be covalently linked to intercalating molecules. The bond energies are typically 400–500 KJ/mole which implies vibrational energies of 40–50 KJ/mole. This is well above an order of magnitude the recoil energies which are 0.25 KJ/mole, 0.59 JK/mole, and 0.52 KJ/mole, respectively. Thus, a recoilless fraction, f, of approximately one is predicted. The Auger cross-sections from Table 8 are $7.16 \times 10^{-18}$ cm$^2$, $2.17 \times 10$ cm$^{-18}$ cm$^2$ and $3.61 \times 10^{-18}$ cm$^2$, respectively. $^{119}$Sn, $^{121}$Sb, and $^{125}$Te are approximately the same atomic number as $^{125}$I where the latter radioactive isotope ejects 21 electrons during an Auger cascade involving the K shell. These former Mossbauer isotopes are predicted to eject the same number of electrons because internal conversion involves K and L shells as demonstrated in FIGS. 13, 14, and Synthetic pathways for exemplary MIRAGE drugs incorporating the Mossbauer isotopes $^{119}$Sn, $^{121}$Sb, and $^{125}$Te and other isotopes from Table 7 appear in the Exemplary Material Section.

SELECTIVITY

Selective killing of selected cells with sparing of nonselected cells can be achieved by several mechanisms:

1. The use of pharmaceuticals where their chemical and physical properties exploit biological phenomena.
2. The use of pharmaceuticals which have a different isomer shift, quadrapole hyperfine splitting, or magnetic hyperfine splitting in selected cells versus nonselected cells.
3. Applying magnetic or electric fields in the space occupied by the selected tissue so that a hyperfine line is created for the selected tissue which is absent for the nonselected tissue.
4. Polarization of the incident gamma rays with resonant polarization of the absorbers in the selected tissue and not in the nonselected tissue.
5. Applying a collinated or focused ultrasonic beam along a line path that intersects the administered gamma rays at the selected tissue site where the former beam excites a component of ultrasonic motion of the Mossbauer absorber nuclei in the direction of the latter beam to produce absorption side bands and where the gamma rays of the second beam are of energy resonant with the side bands.

For case 1

MIRAGE therapy can achieve selectivity in the case of cancer therapy in animals including humans via exploiting known selective uptake by cancer cells of compounds such as Bleomycin, cationic lipophilic dyes such as Rhodanine, hematoporphryins, and monoclonal antibodies. In these cases, a Mossbauer isotope or MIRAGE pharmaceutical is bound to the compound known to be selectively taken up by the cancer. In contrast to chemotherapy, the selectivity need only be relative to other cell types in the Mossbauer radiation field.

The MIRAGE pharmaceutical includes those formed by derivatizing a DNA binding molecule of Table 6 with a Mossbauer absorber atom of Table 7 as described in the General Synthetic Pathways and Exemplary Materials Sections. The carrier and MIRAGE pharmaceutical are attached by a covalent bond such as a disulfide, amide, ester, ether, amine, or carbon-carbon bond which is formed by using existing functional groups or by placing functional groups on the carrier and MIRAGE pharmaceutical such as carboxyl, amino, sulfide, halogen, or carbonyl and condensing the two entities together by methods generally known to one skilled in the art.

Colloids such as those of gallium are known to be concentrated by certain types of cancer cells and the same phenomenon is predicted for certain colloids of Mossbauer isotopes comprising massive inert carriers such as those described in the Macromolecular MIRAGE Pharmaceutical Section. Carriers of $10^8$ daltons or greater are expected to be effective in permitting the Mossbauer effect to occur. Also, many Mossbauer isotopes including metallic and inorganic forms are capable of being incorporated into biological matrices including bone which is useful for the treatment of metastatic bone cancer. Examples include $^{40}$K, $^{153}$Gd, $^{161}$Dy, $^{163}$Dy, $^{149}$Sm, $^{151}$Eu, $^{155}$Gd, and $^{157}$Gd compounds described previously in the Macromolecular MIRAGE Pharmaceutical Section. And, as further described in the mentioned section, Mossbauer isotopes can be incorporated into other biological molecules. For example, Mossbauer isotopes $^{127}$I and $^{129}$I can be incorporated into thyroid hormones and the precursor molecules of thyroid hormones. All can serve as targets for treatment of thyroid cancer with MIRAGE therapy. And $^{57}$Fe can be incorporated into heme proteins and red blood cells. The latter target can be irradiated at the frequency of deoxyhemoglobin which differs from that of oxyhemoglobin to exploit the relative hypoxia of tumors where hypoxia results in a greater concentration of deoxyhemoglobin. Furthermore, damage to the red blood cells in the tumor leads to coagulation followed by thrombosis of the blood supply to the tumor and concomitant tumor death.

For case 2

The energies of the nuclear states are weakly influenced by the chemical environment. The energies of these perturbations relative to the energy of the nuclear transitions in the absence of effects from the environment are of the order of $10^{-10}$. However, the line width of the Mossbauer effect is extremely narrow with monochromaticity of the order of one part in $10^{13}$. This permits selective absorption in a spatial region containing selected cells where these extremely small effects differ from those of the background value of nonselected tissue.

There are three principle interactions, the chemical isomer shift, the magnetic hyperfine interaction, and the quadrapole hyperfine interaction.

CHEMICAL ISOMER SHIFT

The nucleus which is charged interacts with the oppositely charged S electron density which penetrates to the nucleus. For example, the integrated coulombic energy for an electron of charge $-e$ moving in the field of a point nucleus of charge $+Ze$ is given by:

$$E_o = \frac{2e^2}{4\pi\varepsilon_o} \int_o^\infty \varphi^2 \frac{d\tau}{r} \tag{14}$$

where $\epsilon_o$ is the permittivity of a vacuum, r is the radial distance, and $-e\psi^2$ is the charge density of the electron in volume element $d\tau$. When the nucleus undergoes a transition, the size of the nucleus changes which results in a change in the electric monopole or coulombic interaction between the electronic and nuclear charges.

The energy of radiation which produces resonant absorption is a function of the effective electron density at the absorbing nucleus; thus, it shifts as a consequence of a change in the nuclear S electron density. This is seen as a shift of the absorption line away from zero velocity and is variously known as the chemical isomer shift, or centre shift, and is designated by the symbol $\delta$. The Mossbauer experiment compares the difference in energy between the nuclear transitions in the source and absorber, so that the chemical isomer shift as observed is given by $$\delta = \frac{1}{5\varepsilon_o} Ze^2 R^2 \frac{\delta R}{R} (|\varphi_s(o)_{absorber}|^2 - |\varphi_s(o)_{source}|^2) \quad (15)$$

where R is the nuclear radius, e is the charge of an electron, and Z is the atomic number and $|\psi_s(o)|^2$ the non-relativistic Schrodinger wave function at r=0. This can be related to the measured Doppler velocity units, v, by v=(c/Ec)δ.

In equation 15, $|\psi_s(o)|^2$ is the s electron density at the nucleus, and not the s electron occupation in the formal chemical sense. If δR/R is positive, a positive value of the chemical isomer shift, δ, implies the s electron density at the nucleus in the absorber is greater than that in the source. $|\psi_s(o)|^2$ includes contributions from all the occupied s electron orbitals in the atom, but is naturally more sensitive to changes which take place in the outer valance shells. Although the values of $|\psi_s(o)|^2$ for p, d, and f electrons are zero, these orbitals nevertheless do have a significant indirect interaction with the nucleus via interpenetration shielding of the s electrons. For example, a $3d^54s^1$ configuration will have a larger value of $|\psi_s(o)|^2$ than $3d^64s^1$ because in the latter case the extra d electron shields the 4s electron from the nucleus.

MAGNETIC HYPERFINE INTERACTIONS

Figure 16:
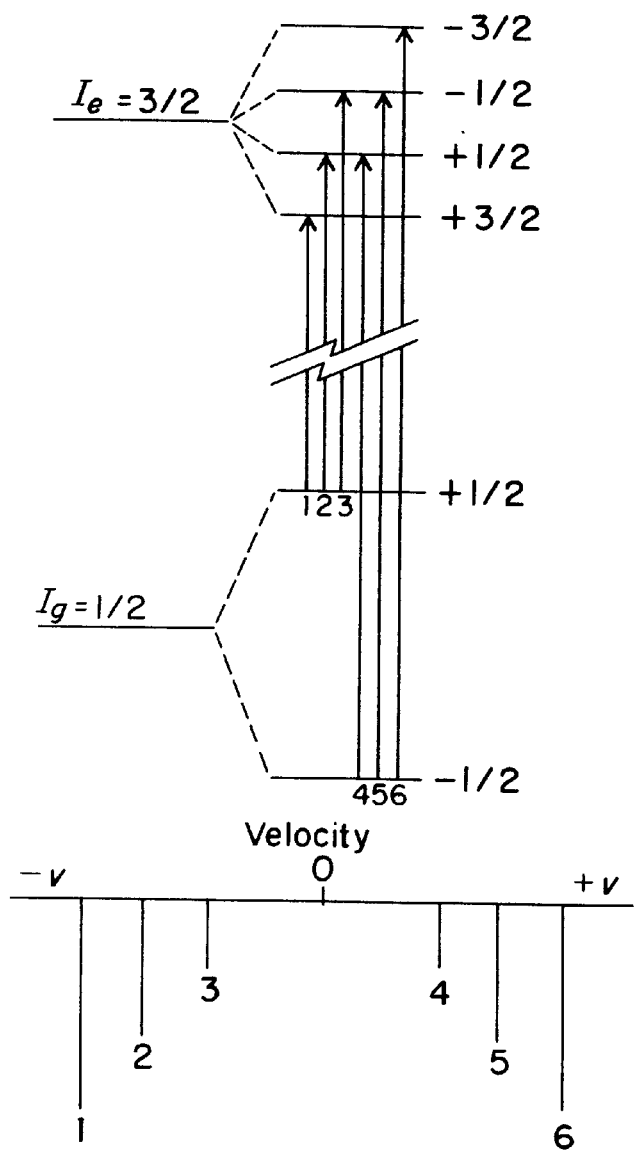
FIG. 16 is the energy level scheme and resultant spectrum for magnetic hyperfine splitting of an $Ig=\frac{1}{2} \rightarrow Ie=\frac{3}{2}$ transition.

The nucleus has a magnetic moment, μ, when the spin quantum number, I, is greater than zero. Its energy is then affected by the presence of a magnetic field, and the interaction of μ with a magnetic flux density of β is formally expressed by the Hamiltonian $$H = -\mu \cdot \beta = -g\mu_N I \cdot B \quad (17)$$

where $\mu_N$ is the nuclear magneton (eh/4 mp=5.049×10⁻²⁷Am² or J/T) and g is the nuclear g-factor [g=u/(I $\mu_N$)]. Solving for this Hamiltonian gives the energy levels of the nucleus in the field to be $$E_m = \frac{-\mu B}{I} m_z = -g\mu_N B_z m_z \quad (18)$$

where $m_z$ is the magnetic quantum number and can take the values I, I-1, . . . -I. In effect, the magnetic field splits the energy level into 2I+1 non-degenerate equi-spaced sublevels with a separation of μB/I. For a Mossbauer nucleus, there may be a transition from a ground state with a spin quantum number Ig and a magnetic moment μg to an excited state with spin Ie and magnetic moment μe. In a magnetic field, both states will be split according to equations 17 and 18. In NMR, radio frequency transitions occur within nondegenerate levels of the ground state; whereas, for the Mossbauer effect gamma ray transitions take place between nondegenerate magnetic sublevels of the ground and excited nuclear states provided that the selection rule $\Delta m_z=o$, ±1 is obeyed [this is called a magnetic dipole (M1) transition which is the predominant transition]. As the result of the presence of an internal magnetic field which can be generated by an unpaired electron in the atomic environment that can induce an imbalance in electron spin density at the nucleus or by an externally applied field, the degeneracy of the ground and excited nuclear level is lifted. The resultant Mossbauer spectrum contains a number of resonance lines, but is nevertheless symmetrical about the centroid. A typical example of magnetic hyperfine splitting is illustrated in FIG. 16 which is drawn to a scale appropriate to $^{119}$Sn. For this isotope I g=½, $I_e$=3/2, $\mu g$=−1.041 μN and $\mu_e$=⁺0.67 μN. The change in sign of the magnetic moment results in a relative inversion of the multiplets. The six lines are the allowed $\Delta m_z$=0,±1 transitions, and the resultant spectrum is indicated in the stick diagram. The lines are not of equal intensity, but the 3:2:1: 1:2:3 ratio shown here is often found for example in the $^{57}$Fe and $^{119}$Sn resonances in randomly oriented polycrystalline samples. A more detailed account of the relative intensities is given in the discussion of polarization of gamma rays.

QUADRAPOLE HYPERFINE INTERACTIONS

Mossbauer nuclei with nuclear states with I>½ have a nuclear quadrapole moment. An electric quadrapole interaction between the nuclear quadrapole moment and the local electric field gradient tensor at the nucleus produces a multiline spectrum as was the case for magnetic hyperfine splitting. The electric quadrapole interaction in Mossbauer spectroscopy is very similar to that in nuclear quadrapole resonance spectroscopy. The main difference is that the latter is concerned with radio frequency transitions within a hyperfine multiplet of a ground state nucleus, whereas, the former is a gamma ray transition between the hyperfine multiplets of the nucleus in its ground and excited states. The electric field gradient is determined by the electronic occupancy of atomic orbitals and is influenced by the bonding to other atoms. Also, in some compounds, the Mossbauer atom has an intrinsically high symmetry (e.g. $Fe^{3+}$ $d^5$ ion has a half filled shell and is a spherical s-state ion) but may still show a quadrapole splitting. The latter originates from charges external to the atom, such as other ions, which polarize the spherical core and can induce a very large electric field gradient at the nucleus.

Selectivity in the eradication of selected cells while sparing nonselected cells can be achieved where a change in the isomer shift, magnetic hyperfine, or quadrapole hyperfine interaction is realized in the selected cells which is different from that of nonselected cells. For example, cancer cells are known to have differences in ion concentrations and ph from normal cells. Binding of an ion or molecule such as a proton (in the case where the MIRAGE pharmaceutical is a weak acid or weak bse with a pKa or pKb, respectively, which is approximately equal to the pH of the organic media at the selected tissue site or the nonselected tissue along the ray path of the administered gamma rays) could result in a change in the electronic interaction at the Mossbauer nucleus and result in a distinct spectrum. Also, the presence of a protein in the target cell which binds to the drug to affect the spectrum could also provide discrimination. This mechanism is discussed in more detail under MIRAGE AIDS Drug.

For case 3

The nuclear spin moments of Mossbauer isotopes become aligned in an imposed magnetic field. The presence of the field lifts the degeneracy of the quantum states and the nucleus must occupy one of these quantum states. Transitions between magnetic sublevels of nuclear states during resonant absorption results in a multiline spectrum. The energy of the transitions, and thus the positions of the lines, are directly proportional to the magnetic field strength. Therefore, by manipulating the external magnetic field strength a transition between magnetic sublevels of the ground and excited nuclear states can be created in the spatial region of the selected tissue such that the energy to achieve resonance is distinctly different from that which achieves resonance in the surrounding nonselected tissue. This is achieved when the resonant energy of the selected tissue is shifted by one line width from that of nonselected tissue. The energies and the dimensions involved are calculated for $^{110}$Sn as follows: The line width for $^{119}$Sn is $2.57 \times 10^{-8}$ ev, the magnetic moment is $-1.046\ \mu_N$ which resonates at 32 MHz for a 2T field. This represents an energy of $1.32 \times 10^{-7}$ ev. This energy is directly proportional to the magnetic flux density, and a realistic flux density gradient is 2000 guass/cm or 10% of the flux density per cm. Since the line width is 20% of the magnetic energy, a 20% change in the flux density is necessary to shift the resonant energy by one line width. This relationship gives 2 cm as the spatial displacement for which the nonselected surrounding tissue becomes transparent with respect to the Mossbauer effect to the radiation which is resonantly absorbed by the selected tissue.

For case 4

Selective absorption in a predetermined region of space can be accomplished by polarizing the source gamma rays and by aligning the spin moments of the selected absorber nuclei with an external magnetic field in a vector orientation relative to the incident polarized gamma ray to permit a nuclear transition between magnetic sublevels which is quantum mechanically allowed only for the proper spin moment alignment. Polarized gamma rays can be obtained by three methods, magnetized ferromagnetic sources, quadrapole split sources, or filter techniques as shown by U. Gonser and H. Fischer, *Current Topics in the Physics of Mossbauer Spectroscopy, The Exotic Side of the Method:* Resonance Gamma Ray Polarimetry, 99–135; incorporated by reference.

Selectivity via polarization of the source and absorber nuclei is possible due to the polarization and angular dependence of transitions between hyperfine quantum sublevels. The intensity of the emitted or absorbed radiation and its dependence on orientation are determined by conservation of angular momentum in the system of nucleus plus gamma ray (quantum selection rules) where the quantum-mechanical treatment of electromagnetic radiation leads to the introduction of photons which are bosons of vanishing rest mass and quantized angular momentum. The intensity of a particular hyperfine transition between quantized sublevels is determined by the coupling of the two nuclear angular momentum states. It can be expressed as the product of two terms which are angular-dependent and angular-independent, respectively.

The former averages to unity for the case of the emission from a source or absorption by the absorber nuclei when all orientations of the magnetic axes of the nuclei are equally possible. Such a case exists for a randomly oriented polycrystalline powder sample where an internal field exists. The intensity in this instance is given by the square of the appropriate Clebsch-Gordan coefficient:

$$\text{intensity } \alpha <I, J-M, M/I_2 M_2>^2 \qquad (19)$$

where the two nuclear spin states $I_1$ and $I_2$ have $I_z$ values of $m_1$ and $m_2$ and their coupling obeys the vector sum $J = I_1 + I_2$ and $m = m_1 - m_2$. J is referred to as the multipolarity of the transition, and the intensity is greater if J is small: if $J=1$, it is referred to as a dipole transition, while with $J=2$ it is a quadrapole transition. Most of the Mossbauer transitions take place without a change in parity, so that the radiation is classified as a magnetic dipole (M1) or electric quadrapole (E2) transition. The selection rule for an M1 or E1 transition is $\Delta m_z = 0, \pm 1$, and for an E2 transition is $\Delta m_z 0, \pm 1, \pm 2$.

The most frequently used coefficients are those for the $\frac{1}{2} \rightarrow 3/2$ M1 transition, and these are given in Table $I_1$, may be either the ground or excited state spin. Although there are nominally eight transitions, the $^{+3/2} \rightarrow^{-1/2}$ and $-3/2 \rightarrow^{+1/2}$ transitions, have a zero probability (forbidden). The six finite coefficients, $C^2$, which express the angular-independent intensity have a total probability of unit intensity and give directly the 3:2:1:1:2:3 intensity ratios for a magnetic hyperfine splitting, shown in FIG. 16. The corresponding terms for a quadrapole spectrum are obtained by summation and give a 1:1 ratio.

TABLE 9

The Relative Probabilities for a 1/2, 3/2 Transition

Magnetic spectra (M1)

| $m_2$ | $-m_1$ | m | C (1) | $C^2$ (2) | $\Theta(J, m)$ (2) |
|---|---|---|---|---|---|
| $+\frac{3}{2}$ | $+\frac{1}{2}$ | +1 | 1 | $\frac{1}{4}$ | $\frac{3}{4}(1+\cos^2\theta)$ |
| $+\frac{1}{2}$ | $+\frac{1}{2}$ | 0 | $\sqrt{\frac{2}{3}}$ | $\frac{1}{6}$ | $\frac{3}{2}\sin^2\theta$ |
| $-\frac{1}{2}$ | $+\frac{1}{2}$ | $-1$ | $\sqrt{\frac{1}{3}}$ | $\frac{1}{12}$ | $\frac{3}{4}(1+\cos^2\theta)$ |
| $-\frac{3}{2}$ | $+\frac{1}{2}$ | $-2$ | 0 | 0 | — |
| $+\frac{3}{2}$ | $-\frac{1}{2}$ | $+2$ | 0 | 0 | — |
| $+\frac{1}{2}$ | $-\frac{1}{2}$ | $+1$ | $\sqrt{\frac{1}{3}}$ | $\frac{1}{12}$ | $\frac{3}{4}(1+\cos^2\theta)$ |
| $-\frac{1}{2}$ | $-\frac{1}{2}$ | 0 | $\sqrt{\frac{2}{3}}$ | $\frac{1}{6}$ | $\frac{3}{2}\sin^2\theta$ |
| $-\frac{3}{2}$ | $-\frac{1}{2}$ | $-1$ | 1 | $\frac{1}{4}$ | $\frac{3}{4}(1+\cos^2\theta)$ |

Quadrupole spectra (M1) when $\eta = 0$

| Transition | $C^2$ (2) | $\Theta(J, m)$ (2) |
|---|---|---|
| $\pm\frac{1}{2}, \pm\frac{1}{2}$ | $\frac{1}{2}$ | $\frac{1}{2}+\frac{3}{4}\sin^2\theta$ |
| $\pm\frac{3}{2}, \pm\frac{1}{2}$ | $\frac{1}{2}$ | $\frac{3}{4}(1+\cos^2\theta)$ |

(1) The Clebsch-Gordan coefficient $\left(\frac{1}{2}\bigg|-m_1 m\bigg|\frac{3}{2}m_2\right)$ (2) $C^2$ and $\Theta(J, m)$ are the angular-independent and angular-dependent terms normalized to a total radiation probability of $$\sum_{m_1 m_2} C^2 \Theta(J, m) = 1$$

The angular dependent terms, $\sigma(J,M)$, are expressed as the radiation probability in a direction at an angle a to the quantization axis (i.e. the magnetic field axis or the principle electric field axis: note that the values in the latter case are only correct if the electric field gradient about the principle axis is symmetric). The intensity for a polycrystalline sample is obtained by integration over all a to obtain a (J,M) as follows:

$$\frac{3}{2}\overline{\sin^2\sigma} = \frac{1}{4\pi}\int_o^{2\pi}\frac{3}{2}\sin^2\sigma\sin\sigma d\sigma d\phi = 1 \quad (20)$$

and the total of emitted radiation is independent of σ and normalized to unity, i.e.

$$\sum_{m_1 m_2}\frac{1}{4}\langle I, J-m_1m/I_2m_2\rangle^2 \overline{\sigma(J,M)} = 1 \quad (21)$$

Figure 17:
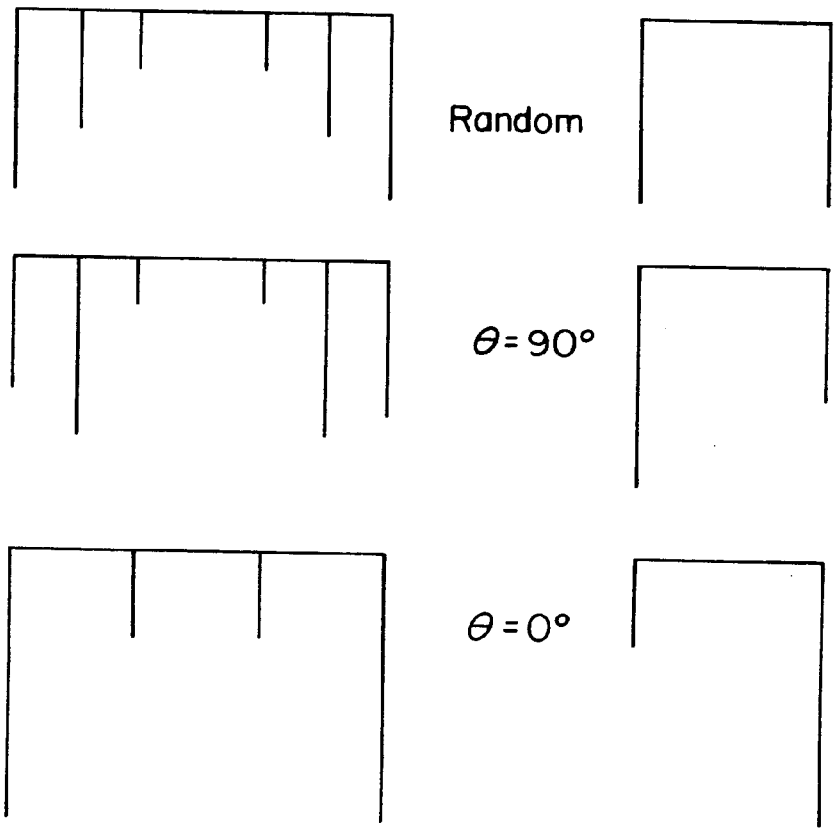
FIG. 17 is the effect of orientation upon the relative line intensities of a magnetic hyperfine splitting and a quadrapole splitting of a $\frac{3}{2} \rightarrow \frac{1}{2}$ transition in an oriented absorber with a unique principle axis system.

Coefficients such as those in Table 9 are necessary to interpret the angular dependence of the spectrum from a single crystal or oriented absorber. For example, a magnetically ordered metal alloy or oxide absorber may often be polarized by magnetizing in a small external magnetic field to give a unique direction of the internal field. The expected line intensities can then be predicted from Table 9 to be in the ratios 3:x:1:1:x:3 where x=4 $\sin^2\sigma/(1+\cos^2\sigma)$; in particular, the Δm=o transitions have a zero intensity when observed along the direction of the field (σ=0°) and a maximum intensity perpendicular to the field (σ=90°). This is illustrated schematically in FIG. 17.

The equivalent behavior in the quadrapole spectrum is a 1:3 ratio for the gamma ray axis parallel to the direction of the principle electric field gradient axis and 5:3 ratio perpendicular to the principle axis.

The angular dependence of the polarization absorption phenomenon is demonstrated experimentally as summarized in FIG. 18a, b. The spectra in FIG. 18 were obtained with a single crystal of α-Fe$_2$O$_3$ (hematite). The crystal was cut parallel to the basal plane and measured (a) at 80° K. and (b) at room temperature. The change in the relative line intensities indicates a reorientation of the spins (Morin transition). Below the Morin temperature ($T_m$=260° K.), the spins are oriented perpendicular to the basal plane of the rhombohedral structure and are parallel and antiparallel to the gamma ray direction. Thus, the Δm=0 lines disappear. Above the Morin temperature the spins flip and align into the basal plane and the Δm=0 lines become strong.

Selective eradication of a selected cell line such as cancer tissue can be achieved by polarizing the cancer tissue with an orientation different from surrounding normal tissue and by irradiating with radiation which excites the corresponding transition. For example, referring to FIG. 18, the nuclei of the MIRAGE pharmaceutical present in the cancer tissue can be aligned perpendicularly to the propagation direction of the gamma ray; whereas, the Mossbauer nuclei present in normal tissue are aligned parallel to the gamma ray propagation direction where alignment in both cases is achieved with an external magnetic field. By irradiation with gamma rays which are resonant with the Δm=0 transition, only the cancer tissue will absorb the radiation.

For Case 5

The line shape for either an absorption or emission Mossbauer line is given by $$W(w) = \frac{\pi}{4}\int_{-\infty}^{\infty}\overline{Q(t)}e^{-\frac{\Gamma}{2}(t/-jwt)}dt \quad (22)$$

where the correlation function $$Q(t) = \langle m/e^{-k\cdot x(t)}e^{iK\cdot x(o)}/m\rangle \quad (23)$$

where Xo is the displacement of the nucleus from its equilibrium position; ζ·k is the momentum of the gamma ray; and the bar devotes a thermal average;

ζw=E-E$_t$, where $E_t$ is the difference in energy between the initial and final nuclear states, Γ is the natural line width of the nuclear excited state; and |m> represents the phonon states of the absorber or source. For the case of harmonic phonon states, the factor $\overline{Q(t)}$ predicts a broad background to the Mossbauer line due to the distribution of thermal phonons in the source or absorber. However, if the source or absorber is excited ultrasonically at a single frequency $\omega_o$, the behavior of Q(t), and hence the line shape is altered drastically. The line shape of an ideal crystal of harmonic phonon states for the two cases in which the phonon relaxation time; the time it takes the initially monochromatic ultrasonic beam to spread into a wave packet characterized by kT, is either very long or very short is given respectively as follows.

$$W(w) = e^{\zeta}\frac{\pi}{4}\sum_{-\infty}^{\infty}\frac{e^{-\zeta_o}I_n(\zeta_o)}{(w-w_n)^2+(\frac{\pi}{4})^2} \quad (24)$$

where In is the modifified Bessel function of the first kind; $e^{-\zeta}$ is the Deby-Waller factor; $\zeta_o = \langle (k\cdot x_o)/^2\rangle$ where Xo is the displacement of the nucleus from equilibrium in the oth normal mode.

$$W(w) = e^{-\zeta}\frac{\pi}{4}\sum_{n=-\infty}^{\infty}\frac{J_n^2\left(\frac{1}{2}\sqrt{\zeta_o}\right)}{(w-nw_o)^2+(\frac{\pi}{4})^2} \quad (25)$$

where Jn is the unmodified Bessel function of the first kind.

For the first case, a short phonon relaxation time results in a Boltzman distribution of ultrasonic phonon states which produces the Mossbauer line shape of Equation 24 where the original single line at frequency $w_t$=E+/ζ has been partially split up into an infinite number of side bands, each of relative intensity $e^{31}$ $^\zeta$In(ζ), spaced at intervals of nwo, integer multiples of the ultrasonic frequency, from the central, unshifted line.

For the second case of a long phonon relaxation time, the lattice phonons are in thermal equilibrium, but the ultrasonic phonons are unable to interact with the thermal phonons; thus, an ultrasonic mode is superimposed to produce the Mossbauer line shape of Equation 25 where, again as for Equation 24, the spectrum splits into an infinite number of side bands, in this case of relative intensity J(½Γζ) spaced as for the former case at intervals of nwo, integer multiples of the ultrasonic frequency from the central, unshifted line.

Selective Mossbauer absorption in a predetermined region of space can be accomplished by simultaneously administering a focused or collinated ultrasonic beam and a gamma ray beam in such a fashion that the beams intersect at the site of the target tissue. The former beam excites a component of ultrasonic motion of the Mossbauer absorber nuclei in the direction of the latter beam to create absorption sidebands spaced at integer multiples of the ultrasonic frequency from the central, unshifted line as described by J. Mishory and D. I. Bolef, *Mossbauer Effect Methodology*, Irwin J. Gruverman, Editor, Vol. 4, (1968) pp. 13–35, incorporated by reference. The administered gamma rays are resonant with a sideband of energy which is not resonant with any of the Mossbauer absorber nuclei in the nonselected tissue along the gamma ray path; thus, selectivity is achieved.

ENERGY SELECTIVE THERAPY

The cross-section for absorption of resonant radiation by Mossbauer nuclei are $10^8$ times that of water; however, nonspecific scattering and absorption occurs for all gamma radiation. The predominant mechanism is the photoelectric effect and Compton scattering.

The photoelectric and Compton cross-sections are summarized in Table 10 which contains the mass energy absorption coefficients in the absence of the Mossbauer effects. The equation for determining the total dose from gamma ray treatment and the depth of penetration of the photons appears in FIG. 12. FIG. 12 and Table 10 demonstrate the relationship that photons of higher energy penetrate deeper into tissue. Since the different Mossbauer sources demonstrate a wide range of photon energies, therapies can be designed to exploit this phenomenon to deliver the energy of the radiation to a selected depth. Mossbauer sources of low energy gamma rays which do not penetrate deeply can be used to deliver therapy superficially and spare deep tissue. For example, $^{57}$Co is the source of a 14.4 KeV Mossbauer gamma ray with a mass energy tissue absorption coefficient of 1.32 cm$^2$/gm and would be suitable for intraoperative radiation and endoscopic radiation using a miniturized source and mass drive or ultrasonic drive. Breast, bowel, and pancreatic cancer are candidates for the former; and lung cancer is a candidate for the latter. Mossbauer sources of high energy gamma rays which penetrate deeply can be used to treat tumors that are not located superficially. $^{155}$Gd is the source of a 60 KeV Mossbauer gamma ray with a mass energy bone absorption coefficient of 0.03 cm$^2$/gm and represents a suitable source for the treatment of primary and metastatic bone cancer and deep solid tumors.

Modifications and substitutions of the compounds, pharmaceuticals, apparatus, methods, systems, and process steps made by one skilled in the art is within the scope of the present invention. Moreover, although Mossbauer absorption includes the absorption of gamma rays, the scope of the present invention includes in the term Mossbauer absorption the absorption of electromagnetic energy at narrow absorption lines or regions by selected materials. Furthermore, the terms wavelength, energy and frequency used herein according to the present invention provide characteristics related according to the formula $$E = h\nu = hc/\lambda$$

Thus the scope of the present invention is not limited except according to the claims which follow.

What is claimed is:

1. A pharmaceutical composition comprising:
   a) a pharmaceutically acceptable solvent, excipient or diluent; and
   b) a Mossbauer absorber atom that is excitable with resonant radiation and that is attached to a chemical which binds to DNA, wherein said chemical which binds to DNA comprises at least one DNA binding, modified form of a compound selected from the group consisting of Phenosafranine, Triostin A, Mithramycin, Chromomycin A$_3$, Phenoxazone Antibiotics, Acridine, Acridinylmethanesulphonanilide, Diacridine, Proflavine, Rhodanine, Acriflavine, 8-Aminoquinoline, Chloroquine, 2-Hydroxyethanethiolato-(2,2',2"-terpyridine)-platinum (II), Naphtholthiophene-ethanolamine, Phenathridine (Ethidium Bromide), Phenanothroline, Ellipticene, 2-Methyl-9-

TABLE 10

MASS ENERGY ABSORPTION COEFFICIENTS

| Mu | A | K | C$_{10}$ | Water | M | Dune | Muuh | MASS ENERGY ABSORPTION COEFFICIENTS ($\mu_{en}$) [cm$^2$/gm] |
|---|---|---|---|---|---|---|---|---|
| 0.010 | 62.0 | 77.0 | 80.8 | 1.80 | 4.66 | 19.0 | 4.96 | |
| .013 | 19.1 | 24.6 | 28.9 | 1.32 | 1.29 | 5.89 | 1.36 | |
| .020 | 8.31 | 10.5 | 12.5 | 0.523 | 0.516 | 2.51 | 0.511 | |
| .030 | 2.16 | 3.12 | 3.75 | 0.117 | 0.117 | 0.713 | 0.151 | |
| .040 | 0.074 | 1.25 | 1.52 | 0.0617 | 0.6110 | 0.305 | 0.0677 | |
| .050 | 0.181 | 0.626 | 0.761 | 0.0391 | 0.6381 | 0.158 | 0.0109 | |
| .060 | 0.281 | 0.367 | 0.413 | 0.0301 | 0.0202 | 0.0970 | 0.0312 | |
| .000 | 0.127 | 0.100 | 0.191 | 0.0253 | 0.0230 | 0.0320 | 0.0255 | |
| .10 | 0.0129 | 0.000 | 0.111 | 0.0252 | 0.0231 | 0.0356 | 0.0252 | |
| .15 | 0.0368 | 0.0133 | 0.0188 | 0.0278 | 0.0251 | 0.0301 | 0.0276 | |
| .20 | 0.0302 | 0.0339 | 0.0367 | 0.0300 | 0.0268 | 0.0302 | 0.0297 | |
| .30 | 0.0278 | 0.0301 | 0.0319 | 0.0320 | 0.0288 | 0.0311 | 0.0317 | |
| .40 | 0.0271 | 0.0200 | 0.0308 | 0.0329 | 0.0296 | 0.0116 | 0.0325 | |
| .50 | 0.0271 | 0.0291 | 0.0301 | 0.0330 | 0.0297 | 0.0316 | 0.0327 | |
| .60 | 0.0270 | 0.0291 | 0.0301 | 0.0320 | 0.0296 | 0.0315 | 0.0326 | |
| .80 | 0.0261 | 0.0282 | 0.0290 | 0.0321 | 0.0289 | 0.0306 | 0.0318 | |
| 1.0 | 0.0252 | 0.0272 | 0.0279 | 0.0311 | 0.0280 | 0.0297 | 0.0308 | |
| 1.5 | 0.0228 | 0.0217 | 0.0253 | 0.0283 | 0.0255 | 0.0270 | 0.0281 | |
| 2.0 | 0.0212 | 0.0228 | 0.0231 | 0.0260 | 0.0231 | 0.0213 | 0.0257 | |
| 3.0 | 0.0193 | 0.0208 | 0.0213 | 0.0227 | 0.0205 | 0.0219 | 0.0225 | |
| 4.0 | 0.0182 | 0.0199 | 0.0201 | 0.0205 | 0.0166 | 0.0199 | 0.0203 | |
| 5.0 | 0.0176 | 0.0193 | 0.0200 | 0.0190 | 0.0173 | 0.0186 | 0.0188 | |
| 6.0 | 0.0175 | 0.0190 | 0.0193 | 0.0180 | 0.0163 | 0.0173 | 0.0178 | |
| 8.0 | 0.0172 | 0.0190 | 0.0197 | 0.0163 | 0.0150 | 0.0165 | 0.0163 | |
| 9.0 | 0.0173 | 0.0191 | 0.0201 | 0.0155 | 0.0141 | 0.0159 | 0.0151 | | hydroxyellipticine, Tilorone, Thioxanthenone, Psoralen, Distamycin A, Netrospin, Hydroxystilbamide, Berenil, DAPI, Hoechst 33258, Irehydiamine A, Dipyradium, Letheoskyrin, Kanchanomycin, Pyrrolo-(1,4)-benzodiazepine Antibiotics, Sibiromycin, Ethylenimine (Triethylene Thiophosphoramide), N-2-Acethylaminofluorene, Benzopyrene, cis-Diamminedichloroplatinum (II), Hedamycin, Rubiflavin, Stretonigrin and Neocarzinostatin.

2. The composition of matter of claim 1, wherein said compound is one of a weak acid and a weak base, and includes an additional proton.

3. The composition of matter of claim 1, wherein said Mossbauer absorber atom has a magnetic moment characteristic.

4. The composition of matter of claim 3, wherein said Mossbauer atom magnetic moment is responsive to an externally imposed magnetic field.

5. The composition of matter of claim 1 wherein said Mossbauer absorbere atom undergoes internal conversion upon absorption of gamma rays, followed by an Auger cascade.

6. The composition of matter of claim 1, wherein said Mossbauer absorber atom undergoes fluorescence upon absorption of gamma rays.

7. The composition of matter of claim 1, wherein the Mossbauer absorber atom has a resonant absorption energy and a resonant frequency in combination with said compound.

8. The composition of matter of claim 7, wherein the Mossbauer absorber is one of $^{40}$K; $^{153}$Gd; $^{155}$Gd; $^{157}$Gd; $^{161}$Dy; $^{163}$Dy and $^{149}$Sm.

9. The composition of matter of claim 1, wherein said Mossbauer absorber atom is selected from the group consisting of $^{176}$Yb, $^{159}$Tb, $^{165}$Ho, $^{231}$Pa, $^{157}$Gd, $^{164}$Er, $^{168}$Er, $^{99}$Tc, $^{156}$Gd, $^{154}$Gd, $^{167}$Er, $^{170}$Er, $^{152}$Sm, $^{176}$Hf, $^{169}$Tm, $^{238}$U, $^{151}$Sm, $^{153}$Sm, $^{154}$Sm, $^{141}$Pr, $^{186}$Os, $^{188}$Os, 177Hf, $^{175}$Lu, $^{160}$Gd, $^{178}$Hf, $^{158}$Gd, $^{166}$Er, $^{133}$Cs, $^{174}$Yb, $^{67}$Zn, $^{172}$Yb, 171Yb, 170Yb, $^{131}$Xe, $^{186}$W, $^{184}$W, $^{183}$W, $^{182}$W, $^{180}$W, $^{232}$Th, $^{236}$U, $^{181}$Ta, $^{125}$Te, $^{147}$Pm, $^{149}$Sm, $^{101}$Ru, $^{99}$Ru, $^{195}$Pt, $^{147}$Pm, $^{189}$Os, $^{237}$Np, $^{61}$Ni, 83Kr, $^{193}$Ir, $^{191}$Ir, $^{201}$Hg, $^{180}$Hf, $^{139}$La, $^{187}$Re, $^{234}$U, $^{239}$Pu, $^{190}$Os, $^{197}$Au, $^{160}$Dy, $^{155}$Gd, $^{73}$Ge, $^{40}$K, $^{243}$Am, $^{145}$Nd, $^{153}$Eu, $^{129,}$ $^{119}$Sn, $^{57}$Fe, $^{151}$Eu, $^{129}$Xe, $^{164}$Dy, $^{161}$Dy, $^{162}$Dy, $^{117}$Sn, $^{121}$Sb, 127I, $^{129}$I, $^{133}$Ba, $^{145}$Pm, and $^{147}$Sm.

* * * * *